United States Patent
Chen et al.

(10) Patent No.: US 11,503,828 B2
(45) Date of Patent: Nov. 22, 2022

(54) ANTIBACTERIAL HYDROPHILIC COMPOUND AND USE THEREOF

(71) Applicant: SHENZHEN UNIVERSITY, Guangdong (CN)

(72) Inventors: Shiguo Chen, Shenzhen (CN); Shaobo Zhang, Shenzhen (CN); Xiaohua Cai, Shenzhen (CN); Zaochuan Ge, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 0 days.

(21) Appl. No.: 16/699,192

(22) Filed: Nov. 29, 2019

(65) Prior Publication Data

US 2020/0093124 A1 Mar. 26, 2020

Related U.S. Application Data

(63) Continuation-in-part of application No. PCT/CN2018/088269, filed on May 24, 2018.

(30) Foreign Application Priority Data

May 31, 2017 (CN) .......................... 201710400759.2

(51) Int. Cl.
| | | |
|---|---|---|
| *A01N 25/34* | (2006.01) | |
| *A01N 33/08* | (2006.01) | |
| *A01N 33/12* | (2006.01) | |
| *A01N 43/18* | (2006.01) | |
| *A01N 43/50* | (2006.01) | |
| *A01N 43/647* | (2006.01) | |

(52) U.S. Cl.
CPC ............. *A01N 25/34* (2013.01); *A01N 33/08* (2013.01); *A01N 33/12* (2013.01); *A01N 43/18* (2013.01); *A01N 43/50* (2013.01); *A01N 43/647* (2013.01)

(58) Field of Classification Search
None
See application file for complete search history.

(56) References Cited

U.S. PATENT DOCUMENTS

2017/0339960 A1 11/2017 Chen et al.
2019/0133123 A1 5/2019 Chen et al.

FOREIGN PATENT DOCUMENTS

CN 105531258 A 4/2016

OTHER PUBLICATIONS

COHEN et al., Journal of the American Chemical Society (1967), 89(23), pp. 5845-5850.*
MANN et al., Journal of the Chemical Society (1951), pp. 747-756.*
International Search Report in PCT/CN2018/088269 dated Aug. 31, 2018, 5 Pages.
Written Opinion in PCT/CN2018/088269 dated Aug. 31, 2018, 8 Pages.
M.F. Saettone et al., Substantivity of Sunscreens-Preparation and Evalution of Some Quaternary Ammonium Benzophenone Derivatives, International Journal of Cosmetic Science, 10(3): 99-109, 1988.
Jing Gao et al., Surface Grafted Antimicrobial Polymer Networks with High Abrasion Resistance, ACS Biomaterials Science & Engineering, 2(7): 1169-1179, 2016.
Cecilia Anselmi et al., Comparative Conformational arid Dynamical Study of Some N-quaternarized UV Filters: Structure-Activity Relationships, J. Chem. Soc. , Perkin Trans 2, 7:1517-1524, 1996.
Lei Qian et al., Durable and Regenerable Antimicrobial Textiles: Synthesis and Applications of 3-methylol-2,2,5,5-tetramethyl-imidazolidin-4-one (MTMIO), Journal Applied Polymer Science, 89(9): 2418-2425, 2003.
Jie Liang et al., Fabric Treated with Antimicrobial N-Halamine Epoxides, Ind. Eng. Chem. Res., 46: 6425-6429, 2007.
Chen, Shiguo et al., Insight into multifunctional polyester fabrics finished by one-step ecofriendly strategy, Chemical Engineering Journal, 358: 634-642, 2019.

* cited by examiner

*Primary Examiner* — Brian J Davis
(74) *Attorney, Agent, or Firm* — Metis IP LLC

(57) ABSTRACT

The present disclosure provides an antibacterial hydrophilic compound. The antibacterial hydrophilic compound may react, induced by light through a hydrogen abstraction group in the structural formula thereof, with a C—H group and thus bind to a surface of a material having the C—H group (for example, chemical fibers such as polyester, chinlon, and the like; plastics, rubbers, and other similar materials), which can impart a durable antibacterial activity and hydrophilicity to the material. The antibacterial hydrophilic compound has a relatively strong binding force to the surface of the material without damaging the mechanical properties of the raw material. The present disclosure also provides a modified material that is modified by the antibacterial hydrophilic compound.

15 Claims, 4 Drawing Sheets

ANTIBACTERIAL HYDROPHILIC COMPOUND AND USE THEREOF

CROSS-REFERENCE TO RELATED APPLICATIONS

This application is a continuation-in-part of International Application No. PCT/CN2018/088269, filed on May 24, 2018, which claims priority to Chinese Application No. 201710400759.2, entitled "Antibacterial Hydrophilic Compound And Use Thereof", filed on May 31, 2017, the entire contents of each of which are incorporated herein by reference.

TECHNICAL FIELD

The present disclosure relates to the field of material surface modification, and in particular, to an antibacterial hydrophilic compound and use thereof.

BACKGROUND

Chemical fibers (such as polyesters, nylons, acrylics, vinylon, etc.) are widely used in the preparation of fabrics, where the polyester is a material that is commonly used with a relatively simple preparation process. The polyester (i.e., the polyester fiber, polyethylene terephthalate (PET)) has characteristics such as good wear resistance, deformation resistance, corrosion resistance, insulation, easy washing and quick drying, which makes the polyester popular. Chemical fibers usually have characteristics such as poor perspiration absorption abilities (hydrophilicity) and difficulties in dyeing. Clothes made of chemical fibers are sultry to wear and easily brings static electricity. Stain or dust easily adhere to such clothes, which affects the aesthetic appearance and comfort. Therefore, hydrophilic modification for chemical fibers becomes a key to improving the wearing comfort of chemical fiber products such as PET. It is difficult for bacteria to breed in original hydrophobic chemical fibers. However, after a hydrophilic treatment, the chemical fibers may easy adsorb human metabolites such as sweat and sebum, which makes microorganisms rapidly multiply on the surface, thereby affecting the aesthetic appearance of the fabric and the health of the wearer. Therefore, it is especially desired to carry out an antibacterial treatment on the chemical fiber surface.

The surface modification of the chemical fibers can be achieved by modifying the compound on its surface. At present, one of the most commonly used processing techniques for textile modification at home and abroad is a finishing process. The finishing process is relatively simple and easy to be scalable for production. The finishing process of the chemical fibers mainly uses alkaline hydrolysis, ammonia hydrolysis, alcoholysis, plasma bombardment, high-energy γ-ray treatment, and other approaches to destroy ester groups of molecular chains in the chemical fibers to produce active groups such as the carboxyl group, the hydroxyl group, and the amino group. Then physical and chemical approaches for modifying these active groups may be carried out to obtain durable hydrophilicity, antibacterial properties, etc.

However, using these approaches has certain negative effects. For example, some processing approaches (such as an atom transfer radical polymerization approach) are very complicated and difficult to scale and industrialize. Some hydrophilic antibacterial agents have a low chemical activity, are easily eluted from fabrics, and lack durable antibacterial properties. As another example, after damaging the ester group of the PET molecular chain, it will reduce the mechanical properties of the textile and affect service life of the textiles.

Therefore, it is desired to provide an antibacterial hydrophilic compound having a durable antibacterial effect that can be stably fixed onto the surface of a material such as fabrics without significant negative effects on the mechanical properties of the material.

SUMMARY

In view of this, some embodiments of the present disclosure provides an antibacterial hydrophilic compound. The antibacterial hydrophilic compound may be firmly bonded to the material by a photo-induced reaction between hydrogen abstraction group (carbonyl group attached between two benzene rings) and —CH— on the surface of natural fibers, artificial fibers (such as polyester, nylon, spandex, polypropylene, vinylon, etc.), and other polymer materials (such as plastics, rubber, etc.). Durable antibacterial activity and hydrophilicity may be achieved, and mechanical properties of the original material may hardly be negatively affected.

The first aspect of the present disclosure provides an antibacterial hydrophilic compound. The general structural formula of the antibacterial hydrophilic compound may be represented by L-D-Q. At least one end of the group L may be connected to the group Q through the linking group D; the group L may have a structure represented by the following formulas ($L_1$), ($L_2$), ($L_3$), ($L_4$) or ($L_5$); the group D may be a single bond or a divalent $C_{1-18}$ hydrocarbyl group that is unsubstituted/substituted, where the divalent $C_{1-18}$ hydrocarbyl group includes or does not include a linking group including heteroatom(s), the heteroatom(s) being at least one of O, S, N, Si, or P atoms; the group Q may be selected from a biguanidine compound residue or a polyamino compound residue represented by a formula ($C_1$), a group represented by the following formulas ($D_1$) or ($D_2$), and a halamine group represented by the following formulas ($B_1$), ($B_2$), ($B_3$), or ($B_4$), where the polyamino compound residue may refer to a residual portion of the polyamino compound excluding —$NH_2$ groups or —OH groups:

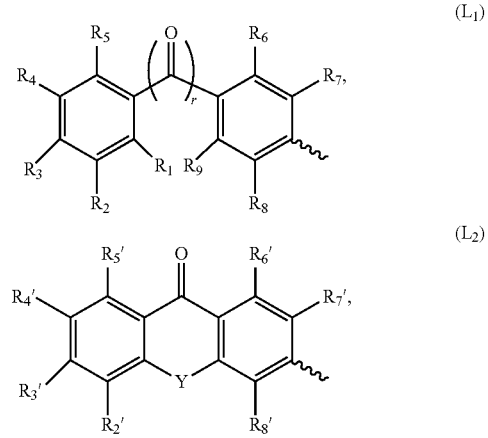

-continued

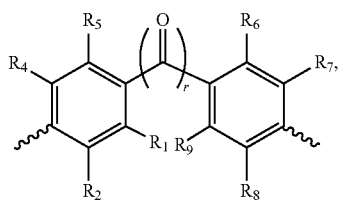
(L₃)

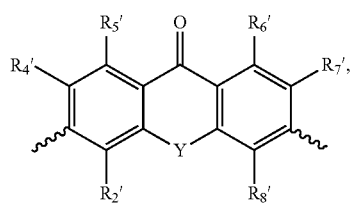
(L₄)

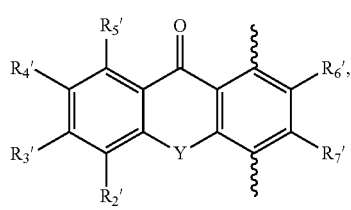
(L₅)

where when L is $L_1$, r may be 1; when L is $L_3$, r may be 1 or 2; Y may be one of a single bond, oxygen atom, sulfur atom, selenium atom, —C(O)— group, —SO₂— group, —NH— group, and $C_{1-3}$ alkylene; $R_1$-$R_9$ and $R_2'$-$R_8'$ may be independently selected from hydrogen atom, halogen atom, monovalent polar group, and a monovalent substituted/unsubstituted $C_{1-18}$ hydrocarbyl group;

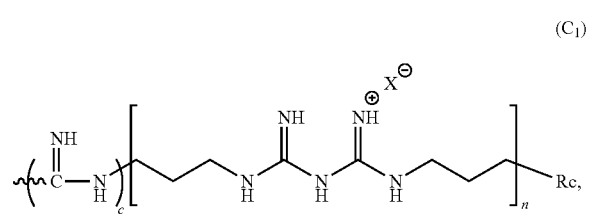
(C₁)

where c may be an integer from 0 to 2, n may be a positive integer from 1 to 100, $R_c$ may be selected from a monovalent unsubstituted/substituted $C_{1-18}$ hydrocarbyl group, and X may be selected from the halogen atom;

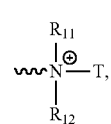
(D₁)

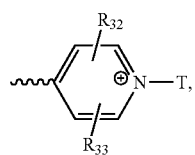
(D₂)

where T may be $R_{13}$ or —$R_{23}$-$A^\ominus$, $R_{11}$-$R_{13}$ may be independently selected from a monovalent $C_{1-18}$ hydrocarbyl group that is unsubstituted/substituted, and $R_{23}$ may be selected from a divalent unsubstituted/substituted $C_{1-18}$ hydrocarbyl group; $R_{32}$-$R_{33}$ may be independently selected from hydrogen atom, halogen atom, monovalent polar group, and a monovalent substituted/unsubstituted $C_{1-18}$ hydrocarbyl group; A may be selected from —COO, —SO₃, and —OPO₂ORe, and Re may be a monovalent $C_{1-6}$ alkyl, cycloalkyl, or aryl group;

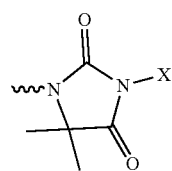
(B₁)

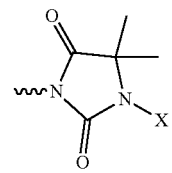
(B₂)

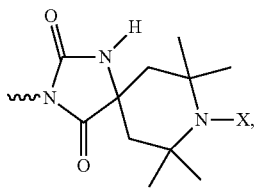
(B₃)

where X may be selected from halogen atom; an end of the group Q with "～～" may be connected to the linking group D.

Preferably, Y may be oxygen atom, sulfur atom, or —C(O)— group.

Preferably, when the group Q is the biguanidine compound residue or the polyamino compound residue represented by the formula (C₁), D may have the following group Z, where Z is —NH—* group, —NH—C(S)—NH—* group, —NH—C(O)—NH—* group, —CO—NH—* group, —SO₂—NH—* group, —CH(OH)—NH—* group, or —CH(OH)CH₂—NH—* group, and an end of the group Z with "*" may be connected to a side of group Q.

Preferably, the polyamino compound may be selected from chitosan, polyethyleneimine, polyamide-amine dendrimer and its derivatives, diethylenetriamine, tetraethylenepentamine, tris(4-aminophenyl)amine, tris(2-aminoethyl)amine, or N'N-bis(3-aminopropyl)methylamine.

Preferably, in the formula (D₁) or (D₂), the $R_{23}$ may be selected from an alkylene group having 1 to 18 carbon atoms; $R_{32}$-$R_{33}$ may be independently selected from hydrogen atom, halogen atom, —CN group, —SCN group, —NO₂ group, —NO group, and a unsubstituted/substituted monovalent $C_{1-7}$ alkyl, cycloalkyl, or aryl group.

Preferably, when the group Q is a structure represented by the formula (D₁), D may be —(CH₂)$_s$—* group, —O—(CH₂)$_t$—* group, —OCO-Ph-(CH₂)$_b$—* group, —NH—COOCH₂—CH₂—* group, —CH₂—NH—COO—CH₂—CH₂—* group, or —O—CH₂—CH(OH)—CH₂—NH—CH₂—* group, and an end of the group D with "*" may be connected to the side of group Q; where s may be an integer from 0 to 10, t may be an integer from 1 to 6, and b may be an integer from 0 to 6.

Preferably, when the group Q is a structure represented by the formula (D₂), the group D may have the following group Z, where Z is —NH—C(O)—NH—* group, —NH—C(S)—NH—* group, —NH—C(S)—O—* group, —NHCOO*— group, and an end of the group Z with "*" may be connected to a side of group Q.

Preferably, when the group Q is a structural formula represented by the formula (D₁) and T is $R_{13}$, the antibacterial hydrophilic compound may be obtained by a nucleophilic addition reaction of a compound with a tertiary amino group represented by the following structural formulas $L_1'$ or $L_2'$ and a halogenated alkane $R_{13}$—X; or obtained by a nucleophilic addition reaction of the compound with a halogenated alkyl group represented by the following structural formulas $L_1'$ or $L_2'$ with a tertiary amine compound

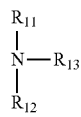

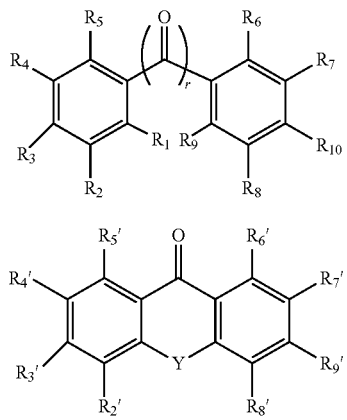

where r may be 1 or 2; Y may be one of single bond, oxygen atom, sulfur atom, selenium atom, —C(O)— group, —SO₂— group, —NH— group, and $C_{1-3}$ alkylene group; $R_1$-$R_{10}$ and $R_2'$-$R_9'$ may be independently selected from hydrogen atom, halogen atom, monovalent polar group, and substituted monovalent $C_{1-18}$ hydrocarbyl group, and at least one of $R_1$-$R_{10}$ or $R_2'$-$R_9'$ is a -D-N($R_{11}$)($R_{12}$) group, or -D-X group. X is halogen atom.

Preferably, when the group Q is a structure represented by the formula (D₁), and T is —$R_{23}$-A$^⊖$, the antibacterial hydrophilic compound may be obtained by reacting the compound $L_1'$ or $L_2'$ represented by the following structural formulas with a tertiary amino group with a compound E:

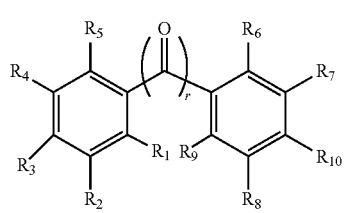

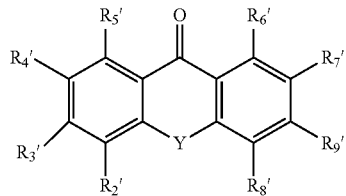

where r may be 1 or 2; Y may be one of single bond, oxygen atom, sulfur atom, e selenium atom, —C(O)— group, —SO₂— group, —NH— group, and $C_{1-3}$ alkylene group; $R_1$-$R_{10}$ and $R_2'$-$R_9'$ may be independently selected from hydrogen atom, halogen atom, monovalent polar group, and a substituted monovalent $C_{1-18}$ hydrocarbyl group, and at least one of $R_1$-$R_{10}$ or $R_2'$-$R_9'$ may be -D-N($R_{11}$)($R_{12}$) group.

The compound E may be selected from sultone, a carboxylic acid lactone, $X(CH_2)_wCOO^-M_t^+$, $X(CH_2)_wSO_3^-M_t^+$, and cyclic phosphate; where X may be selected from Br atom, Cl atom, and I atom, w may be an integer not less than 1, and $M_t^+$ may be selected from Li⁺ ion, Na⁺ ion, K⁺ ion, NH₄⁺ ion, Ag⁺ ion, ½ Mg²⁺ ion, and ½ Ca²⁺ ion; the cyclic phosphate may have a structure represented by the following formula:

where Re may be selected from a monovalent unsubstituted/substituted $C_{1-6}$ alkyl, cycloalkyl, or aryl group, and $R_{23}$ may be selected from a divalent unsubstituted/substituted $C_{1-18}$ hydrocarbyl group.

Preferably, when the group Q is a structure represented by formula (D₂), and T is —$R_{23}$-A$^⊖$, the antibacterial hydrophilic compound may be zwitterionic, which may be prepared by the following method:

(1) reacting the compound $L_1'$ or $L_2$ represented by the following structural formulas with pyridine having the general formula (I) to obtain a mixture,

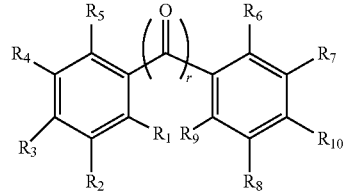

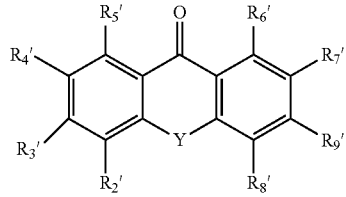

where r may be 1 or 2; Y may be one of single bond, oxygen atom, sulfur atom, selenium atom, —C(O)— group, —SO$_2$— group, —NH— group, and C$_{1-3}$ alkylene group; R$_1$-R$_{10}$ and R$_2$'-R$_9$' may be independently selected from hydrogen atom, halogen atom, monovalent polar group, and a substituted monovalent C$_{1-18}$ hydrocarbyl group, and at least one of R$_1$-R$_{10}$ or R$_2$'-R$_9$' may have —NCO groups or —NCS groups;

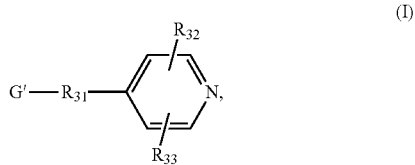
(I)

where G' may be selected from OH group, NH$_2$ group, or —SH group, R$_{31}$ may be selected from a divalent unsubstituted/substituted C$_{1-18}$ hydrocarbyl group, and R$_{32}$-R$_{33}$ may be independently selected from hydrogen atom, halogen atom, monovalent polar group, and a substituted monovalent C$_{1-18}$ hydrocarbyl group;

(2) reacting the mixture with the compound E to obtain a zwitterionic type of antibacterial hydrophilic compound, where the compound E may be selected from sultone, carboxylic acid lactone, X(CH$_2$)$_w$COO$^-$M$_t^+$, X(CH$_2$)$_w$SO$_3^-$ M$_t^+$, and cyclic phosphate; X may be selected from Br atom, Cl atom, and I atom; w may be an integer no less than 1; M$_t^+$ may be selected from Li$^+$ ion, Na$^+$ ion, K$^+$ ion, NH$_4^+$ ion, Ag$^+$ ion, ½ Mg$^{2+}$ ion, and ½ Ca$^{2+}$ ion. The cyclic phosphate may have a structure represented by the following formula:

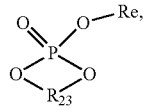

where Re may be selected from a monovalent unsubstituted/substituted C$_{1-6}$ alkyl, cycloalkyl, or aryl group, and R$_{23}$ may be selected from a divalent unsubstituted/substituted C$_{1-18}$ hydrocarbyl group.

Preferably, the structural formula of the carboxylic acid lactone may be

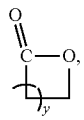

y may be an integer from 1 to 6; the structural formula of the sultone may be

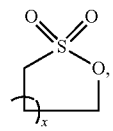

and x may be an integer from 1 to 6.

Preferably, when the group Q is a halamine group represented by the formula (B$_1$), (B$_2$) or (B$_3$), D may be a divalent C$_{1-18}$ hydrocarbyl group that is unsubstituted or substituted, which includes or does not include a linking group including heteroatom(s).

Preferably, when the group Q is a halamine group represented by the formula (B$_1$), (B$_2$) or (B$_3$), the group D is an alkylene having 1 to 10 carbon atoms.

Preferably, when the group Q is a halamine group represented by the formula (B$_1$), (B$_2$) or (B$_3$), the group D may have the following group Z, where Z may be —NH—C(O)—O—CH$_2$—* group, —NH—CH$_2$—CH(OH)—(CH$_2$)$_q$—* group, —S—CH$_2$—CH(OH)—(CH$_2$)$_q$—* group, or —O—CH$_2$—CH(OH)—(CH$_2$)$_q$—* group, where q may be an integer from 1 to 6, and an end of the group Z with "*" may be connected to a side of the group Q.

Preferably, when the group Q is a halamine group represented by the formula (B$_1$), (B$_2$) or (B$_3$), the group D may have the following group Z, where the group Z may be —NH—C(S)—O—CH$_2$—* group, —C(O)—O—CH$_2$—* group, —SO$_2$—O—CH$_2$—* group, —O—CH$_2$—* group, or —CH(OH)CH$_2$—O—CH$_2$—* group, and an end with "*" may be connected to a side of the halamine group.

The antibacterial hydrophilic compound provided by the present disclosure may not be washed off during a washing process after being linked to a material surface having C—H group on the surface, such as a PET fabric. The antibacterial hydrophilic compound may impart durable and effective antibacterial, anti-mold, and hydrophilic properties to the fabrics, and increase the wearing comfort of the fabrics without damaging the breaking force and elongation of the fabrics. The antibacterial hydrophilic compound may be applied to fields including but not be limited to the textile field, coating, medicines, food packaging, etc. For example, it is possible to form chemical bonds by reacting a photoreactive hydrogen abstraction group with most of the macromolecules such as plastics and rubbers to obtain a stable antibacterial plastic, a stable antibacterial rubber, or a stable antibacterial coating. The antibacterial hydrophilic compound may be chemically bonded to material surfaces of medical infusion tubes and medical packaging to prepare antibacterial medicine products, or chemically combined with material surfaces of food packaging or food preservation to prepare antibacterial packaging materials.

The second aspect of the present disclosure provides a use of the antibacterial hydrophilic compound in material modification. The antibacterial hydrophilic compound is described in the first aspect of the present disclosure.

The third aspect of the present disclosure provides a material surface processing method including the following operations:

(1) providing a modification agent containing the antibacterial hydrophilic compound of the first aspect of the present disclosure; and (2) spraying or brushing the modification agent on a material surface containing C—H groups and treating the surface with ultraviolet light to cause the antibacterial hydrophilic compound to covalently bind the surface to obtain a processed material.

Preferably, the material containing the C—H group may be, but not limited to be, selected from natural fibers, synthetic fibers, rubbers, plastics, coatings (in automotive coating or furniture coating, the polymer matrix of the coating may contain the C—H group). The material containing the C—H group may exist independently or may be bonded to a surface of a metal structure, a glass structure, or an oxide structure.

The modification agent may be present in the form of, for example, granules, powder, micellas, solution, suspension, emulsion, or the like, or any combination thereof. In some embodiments, the modification agent may be transported and/or stored in an intermediate formulation. For example, the intermediate formulation may be powder or granules, and the modification agent may be dissolved in an appropriate solvent before usage. As another example, the intermediate formulation may be a liquid with a relatively high concentration (e.g., 80%, 90%) of the compound. The product may be diluted using an appropriate solvent before usage.

Specifically, the synthetic fiber may include polyester (polyethylene terephthalate, also referred to as "PET"), polytrimethylene terephthalate (PTT), polypropylene, acrylic, nylon (nylon 66, nylon 6, nylon 1010), vinylon, spandex (polyurethane), etc.

Preferably, the modification agent may be a finishing liquid. The finishing liquid may contain a polar solvent. Specifically, the polar solvent may include an alkyl alcohol having a 1 to 5 carbon atoms (e.g., methanol, ethanol, n-propanol, isopropanol, n-butanol, 2-butanol, isobutanol (2-methyl-1-propanol), n-pentanol, isoamyl alcohol (3-methyl-1-butanol)), a ketone solvent (acetone, butanone, methyl ethyl ketone, methyl isobutyl ketone, methyl butanone, cyclohexanone, toluene cyclohexanone), an ether solvent (ether, anisole, tributyl methyl ether, petroleum ether), an acid solvent (such as formic acid, acetic acid, trifluoroacetic acid, etc.), an ester solvent (such as butyl acetate, isopropyl tributylacetate, ethyl acetate, ethyl formate, isobutyl acetate, methyl acetate, propyl acetate, etc.), and other common polar solvents (1,2-dichloroethylene, chloroform, dichloroethane, tetrahydrofuran, dimethyl sulfoxide, formamide, N,N-dimethylformamide, N,N-dimethylacetamide, acetonitrile, pyridine, triethanolamine). The polar solvent is not limited to the above mentioned solvents.

The antibacterial finishing liquid may only include the antibacterial hydrophilic compound and solvent; alternatively, in addition to the antibacterial hydrophilic compound and solvent, other additives (such as softeners, antistatic agents, anti-UV additives, etc.) may be added.

Preferably, the ultraviolet light treatment time may be 5 to 10000 s, and more preferably 10 to 600 s.

The fourth aspect of the present disclosure provides a modified material, the modified material including a surface. The surface of the modified material may be covalently bonded with the antibacterial hydrophilic compound described in the first aspect of the present disclosure, where the modified material may have an antibacterial effect.

In some embodiments, at least one mechanical property of the modified material may be improved by the antibacterial hydrophilic compound. The at least one mechanical property may include tearing force (or tearing strength). Alternatively or additionally, the at least one mechanical property may include elongation at break.

The advantages of some embodiments of the present disclosure will be partially explained in the following description. A part of the advantages may be apparent from the description or may be known by the implementation of the some embodiments of the present disclosure.

DETAILED DESCRIPTION

Figure 1:
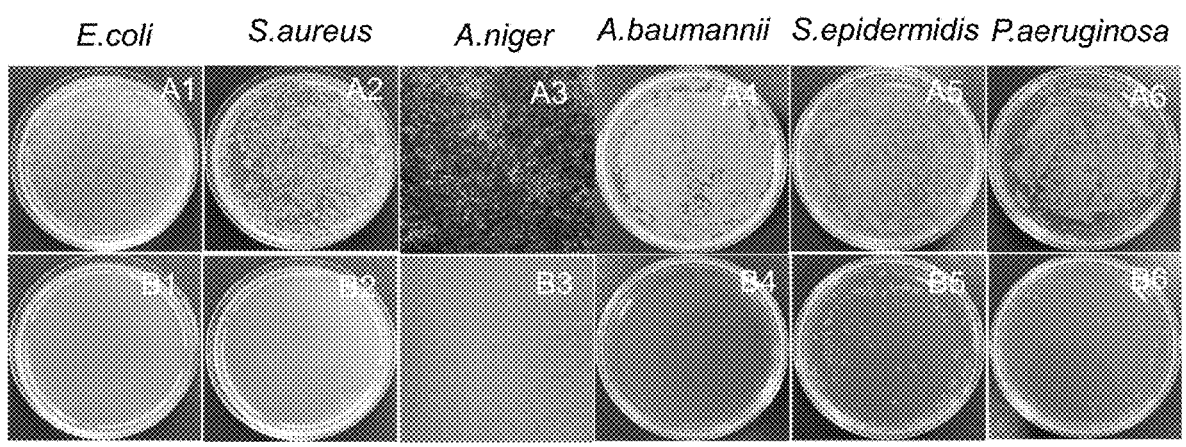
FIG. 1 is a group of photographs illustrating an antibacterial and antifungal effect of PET cloth treated or untreated by an antibacterial hydrophilic compound according to Example 11 of the present disclosure.

The technical solutions in the present disclosure are described clearly and completely in the following with reference to the accompanying drawings and embodiments. It is obvious that the described embodiments are only a portion of the embodiments of the present disclosure, but not all embodiments. All other embodiments obtained by a person skill in the art based on the embodiments of the present invention without creative efforts shall fall within the protection scope of the present invention. It should be noted that the specific embodiments described herein are merely illustrative of the present disclosure and are not intended to limit the present disclosure.

The "halogen atom, monovalent polar group, and substituted monovalent $C_{1-18}$ hydrocarbyl" are explained below.

As for the halogen atom, for example, the halogen atom may be chlorine atom, bromine atom, or iodine atom.

The monovalent polar group may refer that only one bond is linked to another group, and examples thereof may include hydroxyl group (—OH), carboxyl group (—COOH), aldehyde group (—CHO) nitro group (—NO$_2$), nitroso (—NO), primary amino group (—NH$_2$), tertiary amine group (also known as alkylamino group, —NHR), tertiary amine group (or called dialkylamino group, —NR$_1$R$_2$), azido group (—N$_3$), cyano group (—CN), isocyano group (—NC), thiocyano group (—SCN), isothiocyanato group (—NCS), isocyanate group (—NCO), sulfonic acid group (—SO$_3$H), triorganosiloxane group, triorganoalkyl group, and alkoxysilane group, etc.

Hydrocarbyl group (i.e., $C_{1-18}$ hydrocarbyl group) having a count of carbon atoms of 1-18 may include aromatic hydrocarbyl group (pure aryl group, heterocyclic aryl group) and aliphatic hydrocarbyl group (alkyl group, cycloalkyl group, alkenyl group, alkynyl group). These may include, but may not be limited to, straight, branched or ring shaped groups. Alkyl group, a saturated hydrocarbyl, may be a hydrocarbyl formed by removal of a hydrogen atom from an alkane molecule, for example, the alkyl group such as methyl group, methylene group, ethyl group, and isopropyl group (either linear or branched); or alkylene group such as ethylene group, propylidene group. Cycloalkyl group may refer to a general term for hydrocarbyl group formed by removing a hydrogen atom from a saturated hydrocarbon containing an alicyclic structure (such as a monocyclic alicyclic hydrocarbon and a fused ring alicyclic hydrocarbon), such as cyclobutyl group, cyclopentyl group, cyclohexyl group, etc. Aryl group may refer to a general term for a group formed by removing a hydrogen atom from the aromatic nucleus or other carbon atom of any aromatic hydrocarbon molecule, for example, aromatic group such as phenyl group, o-tolyl group, 1-naphthyl group, 2-naphthyl group (or β-naphthyl group), phenmethyl group (benzyl group), phenethyl group, fluorenyl group, biphenyl group, a fluorenyl group, etc., that belong to this class. It may also be an aromatic system containing heteroatom(s), such as pyridine, furan, and thiophene.

The monovalent hydrocarbyl group may refer to a group formed by removing a hydrogen atom bound to a carbon atom in these hydrocarbons, such as methyl group (—$CH_3$), ethyl group (—$CH_2CH_3$), phenyl group (—$C_6H_5$), or the like. The divalent hydrocarbyl may refer to a group formed by removing two hydrogen atoms bound to carbon atom(s) in these hydrocarbons. For example, p-phenylene group (-p-$C_6H_4$—). As another example, $C_{1-3}$ alkylene group that may include methylene group (—$CH_2$—), ethylene group (—$CH_2CH_2$), propylene group (—$CH_2CH_2CH_2$), etc.

These $C_{1-18}$ hydrocarbyl groups may be unsubstituted or may be substituted. The hydrogen atom bound to the carbon atom in these hydrocarbyl groups may be optionally replaced by one or more halogen atoms such as chlorine, bromine, or iodine, may be replaced by the monovalent polar group, may be replaced by one or more linking groups containing a heteroatom (such as alkoxy group, alkanoyl group, decyloxy group, etc.), or may be a group formed by two or more combinations (for example, —COO-Ph-N($CH_3$)($CH_3$)).

Specifically, as the linking group containing heteroatom(s) (O, S, N, Si, or P atoms), for example, ether bond (—O—), thioether bond (—S—), carbonyl group (—CO—), acyloxy group (—COO—), oxycarbonyl group (—OCO—), amide bond (—NHCO—), sulfonyl group (—$SO_2$—), ulfonyloxy group (—$SO_2$—O—), oxysulfonyl group (—O—$SO_2$—), imino group (—NH—), —CH(OH)—NH group, —CH(OH)—$CH_2$—NH group, azo group (—N=N—), siloxane bond,

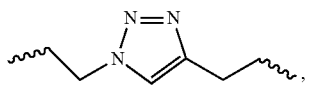

etc. It may also be a group in which the above two or more combinations are connected.

The substituted or unsubstituted $C_{1-18}$ hydrocarbyl group may be directly linked (equivalent to a single bond, i.e., the $C_{1-18}$ hydrocarbyl group may be an unsubstituted hydrocarbyl group or a substituted hydrocarbyl group having no heteroatom linking group), or may also be linked to a benzene ring structure represented by the formula ($L_1$) and/or the formula ($L_2$) by a linking group. As the linking group, an alkylene group having a count of carbon atoms of 1-10 may be listed, and one or more of the linking groups containing O, S, N, Si or P atoms may also be listed. Further, when the substituted or unsubstituted monovalent $C_{1-18}$ hydrocarbyl group is cycloalkyl or aromatic group, the linking group may also be understood as a divalent hydrocarbyl group having a count of carbon atoms of 1-10 (for example, $C_{1-10}$ alkylene group). Groups such as alkoxy group (—OR), alkylthio group (—SR), aryloxy group (—OAr), arylthio group (—SAr) may be understood as the hydrocarbyl group containing ether bond (—O—), thioether bond (—S—) linking group, or hydrocarbyl group substituted by —O, —S—). Groups like ester (—COOR), carbamate (—NHCOOR) may be understood as the hydrocarbyl group with —COO—, —NH—NHCOO-linking group.

The halogen atom and monovalent polar group may be directly linked to a phenyl ring (equivalent to link by single bond), and may be linked to the phenyl ring by substituting an atom of $C_{1-18}$ hydrocarbyl group, for example, —$CH_2NH_2$, —$CH_2Br$, —$CH_2$—N($CH_3$)($CH_3$), —COO-Ph-N($CH_3$)($CH_3$), etc.

"D is a single bond or divalent $C_{1-18}$ hydrocarbyl group that is unsubstituted or substituted, where the divalent $C_{1-18}$ hydrocarbyl group includes or does not include a linking group including heteroatom(s)" is explained below in the present disclosure. The linking group D may be a single bond; may be an unsubstituted divalent $C_{1-18}$ hydrocarbyl group such as -alkylene-($CH_2$)$_s$— (s may be an integer from 1 to 10), phenylene group -Ph-; may be a divalent substituted $C_{1-18}$ hydrocarbyl group containing a heteroatom linking group (this may be understood as "a divalent $C_{1-18}$ hydrocarbyl group substituted with a heteroatom linking group"), for example,

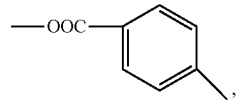

—$CH_2$—CO—NH—, —$CH_2$—CH(OH)—NH—, —O—$CH_2$—CH(OH)—$CH_2$—NH—, etc.; or may also be a divalent substituted C1-18 hydrocarbyl group having no heteroatom linking group, such as —$CH_2$—CH(OH)—$CH_2$—, —$CH_2$—CHBr—,

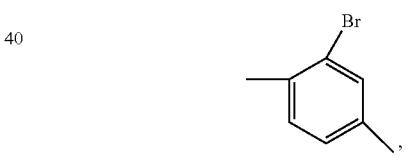

or the like. The divalent $C_{1-18}$ hydrocarbyl group that is unsubstituted or substituted, which includes or does not include a linking group including heteroatom(s) may include an unsubstituted divalent $C_{1-18}$ hydrocarbyl group or a substituted divalent $C_{1-18}$ hydrocarbyl group that includes a linking group including heteroatom(s).

Biguanide Antibacterial Compound: From the Perspective of the General Formula of Final Product In some embodiments of the present disclosure, an antibacterial hydrophilic compound is provided. A general structural formula of the antibacterial hydrophilic compound may be represented by L-D-Q, where at least one end of the group L may be connected to the group Q through the linking group D; the group L may have a structure represented by the following formulas ($L_1$), ($L_2$), ($L_3$), ($L_4$) or ($L_5$); D may be a divalent $C_{1-18}$ hydrocarbyl group that is unsubstituted or substituted, which includes or does not include a linking group including heteroatom(s), and the heteroatom(s) may be at least one of O, S, N, Si, or P atoms; the group Q may be selected from a biguanide compound residue represented by the formula ($C_1$):

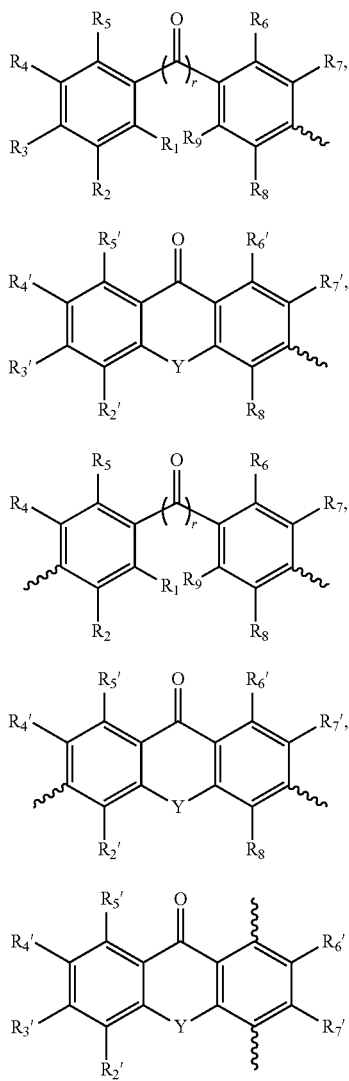

(L₁)

(L₂)

(L₃)

(L₄)

(L₅)

where when L is $L_1$, r may be 2; when L is $L_3$, r may be 1 or 2; Y may be one of single bond, oxygen atom, sulfur atom, selenium atom, —C(O)— group, —SO₂— group, —NH— group, and $C_{1-3}$ alkylene group; $R_1$-$R_9$ and $R_2'$-$R_8'$ may be independently selected from hydrogen atom, halogen atom, monovalent polar group, and a monovalent substituted/unsubstituted $C_{1-18}$ hydrocarbyl group;

(C₁)

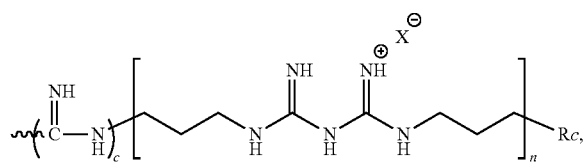

where c may be an integer from 0 to 2, n may be a positive integer from 1 to 100, $R_c$ may be selected from a monovalent unsubstituted/substituted $C_{1-18}$ hydrocarbyl group, and X may be selected from chlorine, bromine or iodine atom.

Preferably, when the group Q is the biguanidine compound residue represented by the formula ($C_1$), the group D may be a divalent $C_{1-18}$ hydrocarbyl group that is unsubstituted or substituted, which includes or does not include a linking group including heteroatom(s).

Preferably, the group D has the following group Z, and the group Z is —NH—* group, —NH—C(S)—NH—* group, —NH—C(O)—NH—* group, —CO—NH—* group, —SO₂—NH—* group, —CH(OH)—NH—* group, or —CH(OH)CH₂—NH—* group, and an end of the group Z with "*" may be connected to a side of structure shown in ($C_1$).

The "group D with the following group Z" may be understood that the group D equals to the group Z (the other side of the group Z is directly connected to the group L), or the group D is —R'—Z, where R' may be a substituted divalent $C_{1-18}$ hydrocarbyl group.

Further, the group D may be —R'—Z, where R' may be —(CH₂)$_a$— or —O—CH₂—, and a may be an integer of 0-10. Similarly, the group Z may be —NH—* group, —NH—C(S)—NH—* group, —NH—C(O)—NH—* group, —CO—NH—* group, —SO₂—NH—* group, —CH(OH)—NH—* group, or —CH(OH)CH₂—NH—* group, and an end of the group Z with "*" may be connected to a side of the structure shown in ($C_1$).

Specifically, the group D may be —CH₂—NH—C(S)—NH—* group, —CH₂—CO—NH—* group, —CH₂—CH(OH)—NH—* group, —O—CH₂—CH(OH)CH₂—NH—* group, or —CH₂—NH—C(S)—NH—* group, etc.

Biguanide Antibacterial Compound: From the Perspective of Reaction Raw Materials When the group Q is selected from the biguanidine compound residue represented by the formula ($C_1$), the antibacterial hydrophilic compound may be obtained by reacting active group $Z^1$ in the compound $L_1'$ or $L_2'$ shown by the following structural formula with —NH₂ group on the biguanidine compound represented by the formula ($C_1'$):

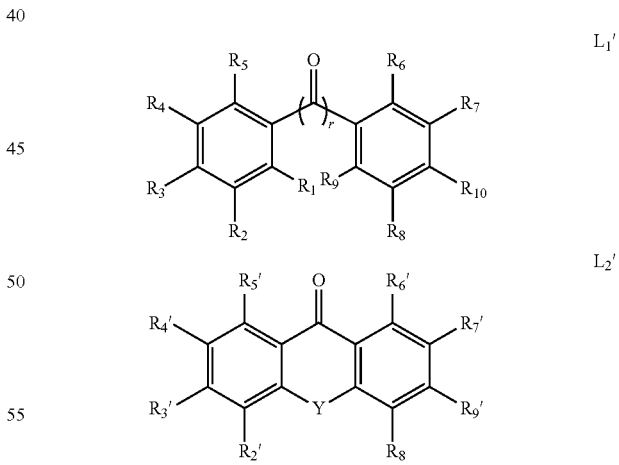

where r may be 1 or 2; Y may be one of single bond, oxygen atom, sulfur atom, selenium atom, —C(O)— group, —SO₂— group, —NH— group, and $C_{1-3}$ alkylene group; $R_1$-$R_{10}$ and $R_2'$-$R_9'$ are independently selected from hydrogen atom, halogen atom, monovalent polar group, and a substituted or unsubstituted monovalent $C_{1-18}$ hydrocarbyl group, and at least one of the $R_1$-$R_{10}$ or the $R_2'$-$R_9'$ may be linked to the biguanidine compound represented by the formula ($C_1'$), at least one of the $R_1$-$R_{10}$ or the $R_2'$-$R_9'$ may include the following active group $Z^1$, and $Z^1$ may be —X, —NCS group, —NCO group, —COOH group,

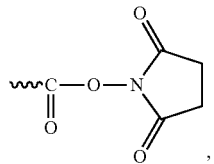

—COX group, —SO$_2$X group, —CHO group, or —CH(O)CH$_2$ group, where X may be —Cl, —Br, or —I group;

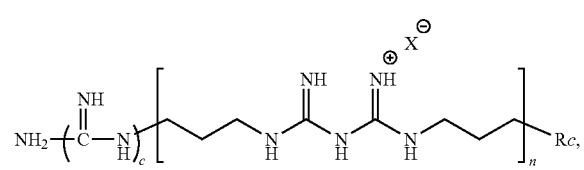

(C$_1$')

in the formula (C$_1$'), c may be an integer of 0-2, n may be a positive integer of 1-100, R$_c$ may be selected from a monovalent unsubstituted/substituted C$_{1-18}$ hydrocarbyl group, and X may be selected from chlorine, bromine or iodine atom.

Preferably, in the formula (C$_1$'), n may be a positive integer of 1-20.

Preferably, at least one of the R$_1$-R$_{10}$ or the R$_2$'-R$_9$' may be —R'—Z$^1$, and R' may be a substituted/unsubstituted divalent C$_{1-18}$ hydrocarbyl group.

Further preferably, at least one of the R$_1$-R$_{10}$ or the R$_2$'-R$_9$' may be —(CH$_2$)$_a$—Z$^1$, where a may be an integer from 0-10.

Further preferably, when Z$^1$ is —X group (—Cl, —Br, or —I group), a may be an integer from 1 to 10.

In the present disclosure, any one of the R$_1$-R$_{10}$ or the R$_2$'-R$_9$' may be linked to the antibacterial group Q. In view of the ease of the organic reaction, preferably, at least one of the R$_3$ or R$_{10}$ may be linked to the antibacterial group Q; at least one of the R$_3$' or R$_9$' may be linked to the antibacterial group Q. When one of the R$_3$ or R$_{10}$, or one of the R$_3$' or R$_9$' is linked to the antibacterial group Q, an L-Q type structure may be formed; when both the R$_3$ and R$_{10}$ are linked to the antibacterial group Q, or both R$_3$' and R$_9$' are linked to the antibacterial group Q, a Q-L-Q type structure may be formed.

In some embodiments, the antibacterial hydrophilic compound may be obtained by reacting the active group Z$^1$ in the compound L$_1$' or L$_2$' with —NH$_2$ group on the biguanidine compound represented by the formula (C$_1$'). Specifically, the active group Z$^1$ may react with —NH$_2$ to form the group Z, where when the Z$^1$ group is X (—Cl, —Br or —I group), the group Z formed by reacting with —NH$_2$ group may be —NH—* group; when the Z$^1$ group is —NCS group, the group Z formed by reacting with —NH$_2$ group may be —NH—C(S)—NH—* group; when the Z$^1$ group is —NCO group, the group Z formed by reacting with —NH$_2$ group may be —NH—C(O)—NH—* group; when the Z$^1$ group is —COOH group or —COX group, the group Z formed by reacting with —NH$_2$ group may be —CO—NH—* group; when the Z$^1$ group is —SO$_2$X group, the group Z formed by reacting with —NH$_2$ group may be —SO$_2$—NH—* group;

when Z$^1$ is —CHO group, the group Z formed by reacting with —NH$_2$ group may be —CH(OH)—NH—* group; When Z$^1$ is —CH(O)CH$_2$ group, the group Z formed by reacting with —NH$_2$ group may be —CH(OH)CH$_2$—NH*— group. The end of the group Z with "*" may be connected to a side of the structure shown in (C$_1$) (i.e., the group Q).

Polyamino Antibacterial Compound

In some embodiments of the present disclosure, an antibacterial hydrophilic compound is provided. The structural formula of the antibacterial hydrophilic compound may be represented by L-D-Q, where at least one end of the group L may be connected to the group Q through the linking group D; the group L may have a structure represented by the following formulas (L$_1$), (L$_2$), (L$_3$), (L$_4$) or (L$_5$); the group D may be a divalent C$_{1-18}$ hydrocarbyl group that is unsubstituted or substituted, which includes or does not include a linking group including heteroatom(s), and the heteroatom may be at least one of O, S, N, Si, and P atoms; the group Q may be selected from a polyamino compounds residue, which may refer to a portion of the polyamino compound excluding —NH$_2$ groups or —OH groups:

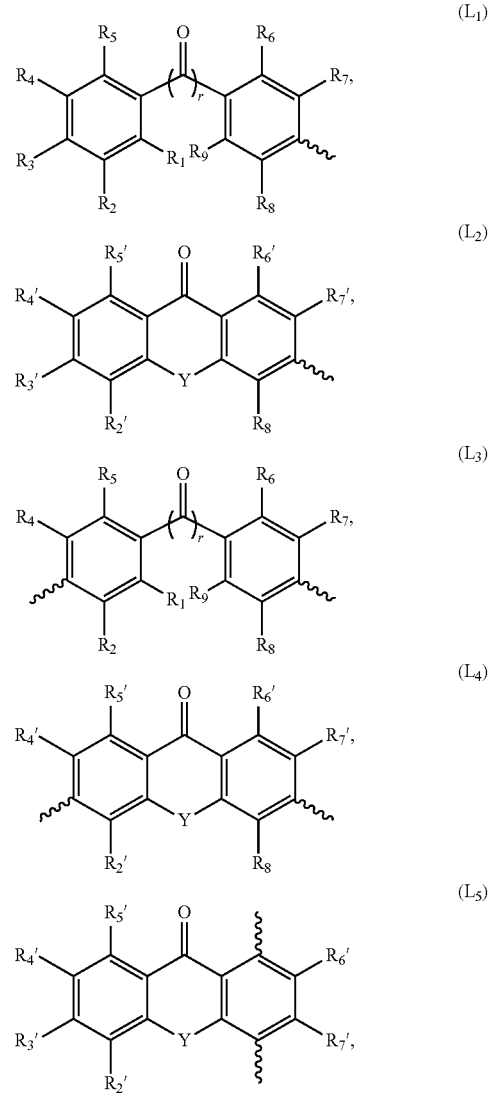

where $R_1$-$R_9$ and $R_2'$-$R_8'$ may be independently selected from hydrogen atom, halogen atom, monovalent polar group, and a monovalent substituted/unsubstituted $C_{1-18}$ hydrocarbyl group.

When Q is a polyamino compound residue (in this case, the polyamino compound residue is the residual portion of the polyamino compound excluding at least one —$NH_2$ group), it may be similar to the case where Q is a biguanidine compound residue. At this time, the group D may be a divalent $C_{1-18}$ hydrocarbyl group that is unsubstituted or substituted, which includes or does not include a linking group including heteroatom(s).

Specifically, when the group Q is the polyamino compound residue (after the polyamino compound excludes at least one —$NH_2$ group), the antibacterial hydrophilic compound may be obtained by reacting the active group $Z^1$ in the compound L1' or L2' shown by the following structural formula with —$NH_2$ group on the polyamino compound:

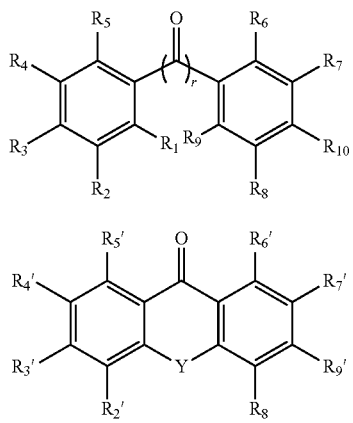

where r may be 1 or 2; Y may be one of single bond, oxygen atom, sulfur atom, selenium atom, —C(O)— group, —$SO_2$— group, —NH— group, and $C_{1-3}$ alkylene group; $R_1$-$R_{10}$ and $R_2'$-$R_9'$ are independently selected from hydrogen atom, halogen atom, monovalent polar group, and a substituted or unsubstituted monovalent $C_{1-18}$ hydrocarbyl group, and at least one of the $R_1$-$R_{10}$ or the $R_2'$-$R_9'$ may be linked to the polyamino compound, at least one of the $R_1$-$R_{10}$ or the $R_2'$-$R_9'$ may include the following active group $Z^1$, and $Z^1$ may be —X, —NCS group, —NCO group, —COOH group,

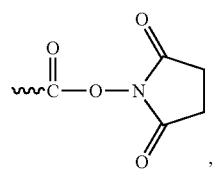

—COX group, —$SO_2$X group, —CHO group, or —CH(O)$CH_2$ group, where X may be —Cl, —Br, or —I group.

In the present disclosure, the polyamino compound is a compound having two or more amino groups. The polyamino compounds may include, but be not limited to, chitosan, polyethyleneimine (PEI), polyamide-amine (PAMAM) dendrimers and derivatives thereof, diethylenetriamine, tetraethylene pentamine, tris(4-aminophenyl)amine, tris(2-aminoethyl)amine, N'N-bis(3-aminopropyl)methylamine. Where the molecular formula of diethylenetriamine may be $H_2NCH_2CH_2NHCH_2CH_2NH_2$; the molecular formula of tetraethylene pentamine may be $H_2N(CH_2CH_2NH)_3CH_2CH_2NH_2$; the formula of tris(4-aminophenyl)amine, tris(2-aminoethyl)amine may be $N(CH_2CH_2NH_2)_3$, and the formula of N'N-bis(3-aminopropyl)methylamine may be $H_2NCH_2CH_2CH_2N(CH_3)CH_2CH_2NH_2$.

The structural formulas of PEI and PAMAM may be presented as the following formulas (F1) and (F2):

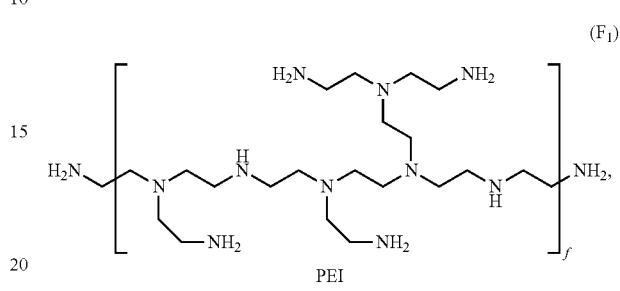

f may be an integer from 1 to 100.

(F2)

When Q is a polyamino compound residue (such as chitosan, PEI, PAMAM), in addition to imparting antibacterial and hydrophilicity to the material surface, it may also impart antistatic property to the material. If the antibacterial hydrophilicity compound is used in the treatment of textiles, it may contribute to anionic dyeing.

In particular, for a polyamino compound containing both amino group and —OH group, it may react with the compound $L_1'$ or $L_2'$ either by —$NH_2$ group in its structure or by the active group —OH in its structural formula. For example, chitosan, except for the reaction of the amino group at the C2 position with the active group on the compound $L_1'$ or $L_2'$ (as shown in the following formula ($A_1$)), the chitosan may also react with —$CH_2OH$ group at the C6 position (shown by formula ($A_2$) below) or by —OH group at the $C_3$ position with the active group on the compound $L_1'$ or $L_2'$ (the following formula ($A_3$)):

(A₁)

-continued

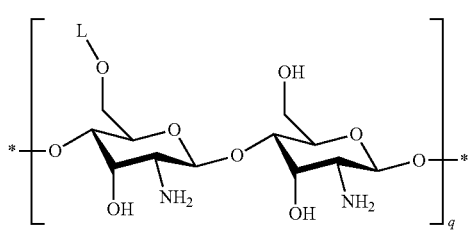
(A₂)

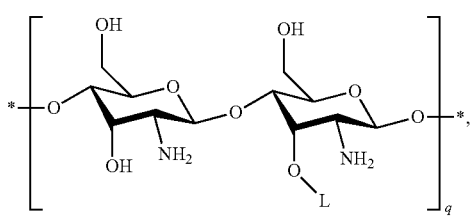
(A₃)

where q may be an integer from 1 to 1000.

Quaternary Ammonium Salt Type or Zwitterionic Type of Antibacterial Compound:

In some embodiments of the present disclosure, an antibacterial hydrophilic compound is provided. The structural formula of the antibacterial hydrophilic compound may be represented by L-D-Q, where at least one end of the group L may be linked to the group Q through the linking group D; the group L may have a structure represented by the following formulas ($L_1$), ($L_2$), ($L_3$), ($L_4$) or ($L_5$); D may be single bond or divalent $C_{1-18}$ hydrocarbyl group that is unsubstituted or substituted, which includes or does not include a linking group including heteroatom(s). The heteroatom(s) include at least one of O, S, N, Si, and P atoms; the group Q may be selected from the group represented by the following formula ($D_1$) or ($D_2$):

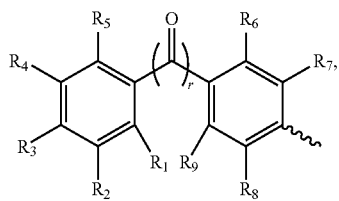
($L_1$)

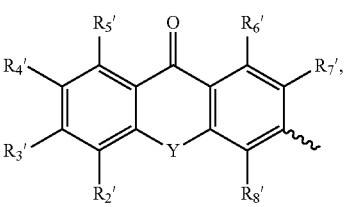
($L_2$)

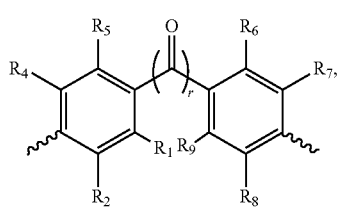
($L_3$)

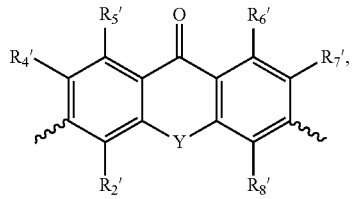
($L_4$)

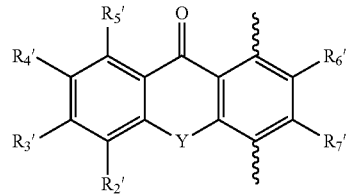
($L_5$)

where $R_1$-$R_9$ and $R_2'$-$R_8'$ may be independently selected from hydrogen atom, halogen atom, monovalent polar group, and a monovalent substituted/unsubstituted $C_{1-18}$ hydrocarbyl group;

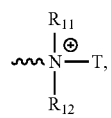
($D_1$)

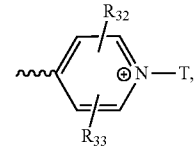
($D_2$)

where T may be $R_{13}$ or —$R_{23}$-$A^\ominus$, $R_{11}$-$R_{13}$ may be independently selected from a monovalent unsubstituted/substituted $C_{1-18}$ hydrocarbyl group, and $R_{23}$ may be selected from a divalent unsubstituted/substituted $C_{1-18}$ hydrocarbyl group; $R_{32}$-$R_{33}$ may be independently selected from hydrogen atom, halogen atom, monovalent polar group, and a monovalent substituted/unsubstituted $C_{1-18}$ hydrocarbyl group; A may be selected from —COO, —$SO_3$ and —$OPO_2ORe$, and Re may be a monovalent unsubstituted/substituted $C_{1-6}$ alkyl, cycloalkyl, or aryl group;

where when D is single bond, at least one end of the group L may be directly connected to the group Q represented by the formula ($D_1$) or ($D_2$).

Preferably, the $R_{11}$-$R_{13}$ may be independently selected from unsubstituted $C_{1-18}$ straight or branched alkyl group.

Further preferably, the $R_{11}$ and $R_{12}$ may be a methyl group. The $R_{13}$ may be an unsubstituted $C_{10-16}$ alkyl group.

Preferably, the $R_{23}$ may be selected from alkylene group having a count of carbon atoms of 1-18 (i.e., —$(CH_2)_m$— group, m being an integer from 1 to 18). Further preferably, the $R_{23}$ may be selected from alkylene group having a count of carbon atom of 1-10.

Preferably, the $R_{32}$-$R_{33}$ may be independently selected from hydrogen atom, halogen atom, —CN group, —SCN group, —$NO_2$ group, —NO group, and a monovalent unsubstituted/substituted $C_{1-7}$ alkyl, cycloalkyl, or aryl group.

Further preferably, the $R_{32}$-$R_{33}$ may be independently selected from hydrogen atom, halogen atom, —$NO_2$ group, methyl group, and ethyl group.

Preferably, the Re may be a monovalent unsubstituted $C_{1-6}$ alkyl group.

In the present disclosure, when the group Q is a structure represented by the formula ($D_1$) or ($D_2$) and T is $R_{13}$ ($R_{11}$, $R_{12}$, and $R_{13}$ are all fluorine-free substituents), the antibacterial hydrophilic compound may be a quaternary ammonium salt type compound. At this time, in addition to imparting the hydrophilic, antibacterial, and anti-mildew functions to the textile or material, the group Q may also impart an antistatic and easy dyeing function; when the group Q is a structural formula represented by the formula ($D_1$) or ($D_2$) (T is —$R_{23}$-$A^\ominus$), the antibacterial hydrophilic compound may be a zwitterionic compound; at this time, in addition to imparting the durable hydrophilic and antibacterial function to the surface of the textile or material, the group Q may also impart an antistatic function, and may not adhere to bacteria, and may have antifouling effect.

Further, when the group Q is a structure represented by the formula ($D_1$) and T is $R_{13}$, the antibacterial hydrophilic compound may be obtained by a nucleophilic addition reaction of the compound L1' or L2' having a tertiary amino group (for example, containing -D-N($R_{11}$)($R_{12}$)) with a halogenated alkane $R_{13}$—X; alternatively, obtained by the nucleophilic addition reaction of the compound L' represented by the formula ($L_1$') or $L_2$' having a halogenated alkyl group (-D-X, X may be chlorine, bromine, or iodine) with a tertiary amine compound

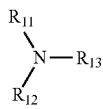

(preferably obtained in the manner of the former).

Similarly, when Q is a structural formula shown as the formula ($D_2$) (and T is $R_{13}$), the antibacterial hydrophilic compound may be obtained by a nucleophilic addition reaction of compound L with group

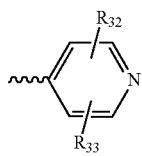

with a halogenated alkane $R_{13}$—X.

Preferably, when the group Q is a structure represented by the formula ($D_1$), (T is $R_{13}$ or T is —$R_{23}$-$A^\ominus$), the linking group D in the antibacterial hydrophilic compound may be —$(CH_2)_s$—* group, —O—$(CH_2)_t$—* group, —OCO-Ph-$(CH_2)_b$—* group, —NH—COOCH$_2$—CH$_2$—* group, —CH$_2$—NH—COO—CH$_2$—CH$_2$—* group, or —O—CH$_2$—CH(OH)—CH$_2$—NH—CH$_2$—* group (but not limited thereto). The end of the group D with "*" may be connected to a side of group Q shown by the formula ($D_1$) or ($D_2$); where s may be an integer from 0 to 10, t may be an integer from 1 to 6, and b may be an integer from 0 to 6.

Further preferably, the s may be an integer from 0 to 4, t may be 1 or 2, and b may be an integer from 0 to 3.

Specifically, the group D may be —CH$_2$— group, —O—CH$_2$—CH$_2$—* group, —O—CO-Ph-* group, —NH—COOCH$_2$—CH$_2$—* group, —CH$_2$—NH—COO—CH$_2$—CH$_2$—* group, —O—CH$_2$—CH(OH)—CH$_2$—NH—CH$_2$—* group, etc.

Further, when the group Q is a structure (T is —$R_{23}$-$A^\ominus$) represented by the formula ($D_1$), the antibacterial hydrophilic compound may be obtained by reacting the compound L1' or L2' represented by the following structural formulas with tertiary amino group (for example, containing —N($R_{11}$)($R_{12}$) group) with a compound E to obtain the zwitterionic type of the antibacterial hydrophilic compound:

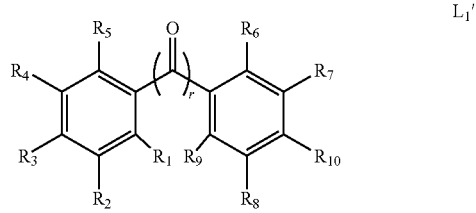

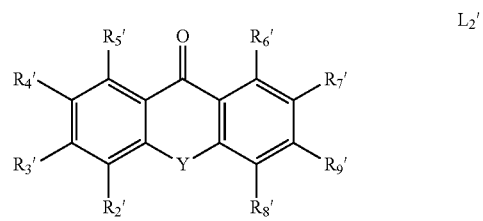

where r may be 1 or 2; Y may be one of single bond, oxygen atom, sulfur atom, selenium atom, —C(O)— group, —SO$_2$— group, —NH— group, and $C_{1-3}$ alkylene group; $R_1$-$R_{10}$ and $R_2$'-$R_9$' may be independently selected from hydrogen atom, halogen atom, monovalent polar group, and a substituted monovalent $C_{1-18}$ hydrocarbyl group, and at least one of the $R_1$-$R_{10}$ or the $R_2$'-$R_9$' may be -D-N($R_{11}$)($R_{12}$) group;

The compound E may be selected from sultone, carboxylic acid lactone, $X(CH_2)_wCOO^-M_t^+$, $X(CH_2)_wSO_3^-M_t^+$, and cyclic phosphate; X may be selected from Br atom, Cl atom, and I atom, w may be an integer not less than 1, and $M_t^+$ ion may be selected from Li$^+$ ion, Na$^+$ ion, K$^+$ ion, NH$_4^+$ ion, Ag$^+$ ion, ½ Mg$^{2+}$ ion, and ½ Ca$^{2+}$ ion; the cyclic phosphate may have a structure represented by the following formula:

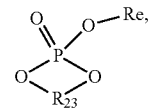

Re may be selected from a monovalent unsubstituted/substituted $C_{1-6}$ alkyl, cycloalkyl, or aryl group, and $R_{23}$ may be selected from a divalent unsubstituted/substituted $C_{1-18}$ hydrocarbyl group.

Preferably, the $R_{23}$ may be an alkylene group having a count of carbon atoms of 1-18 (i.e., —$(CH_2)_m$—, m may be an integer from 1 to 18). Further preferably, the $R_{23}$ may be selected from an alkylene group having a count of carbon atoms of 1-10. More preferably, the alkylene group may have a count of carbon atoms of 1-16.

Preferably, Re may be selected from a monovalent unsubstituted/substituted $C_{1-6}$ alkyl, cycloalkyl, or aryl group.

Preferably, w may be an integer from 1 to 6.

Preferably, the structural formula of the sultone may be

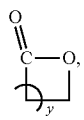

and x may be an integer from 1 to 6. Preferably, the sultone may also be propylene-1,3-sulfonate

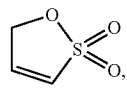

2,4-butane sultone

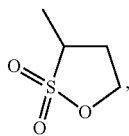

or the like.

Preferably, the structural formula of the carboxylic acid lactone may be

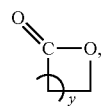

y may be an integer from 1 to 6. Further preferably, it may be an integer of 1-3.

For example, taking the compound $L_1'$ or $L_2'$ having a tertiary amino group —$CH_2$—$N(CH_3)(CH_3)$ as an example, the zwitterionic type of the antibacterial hydrophilic compound may be obtained by the following reaction route:

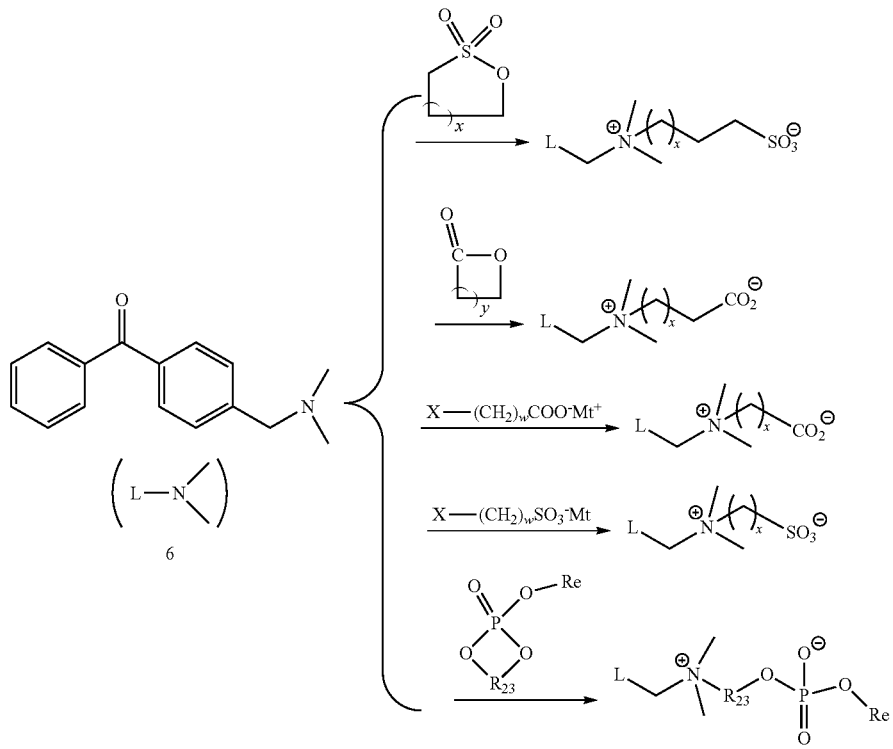

In the reactant E, since the carbon atom linked to the oxygen atom in the sultone is easily subjected to attack by a nucleophile, a nucleophilic tertiary nitrogen atom may be present in the mixture obtained in the first step reaction. Therefore, a ring-opening reaction may occur between the reactant E and the mixture obtained by the first step reaction to form a C—N bond. The tertiary nitrogen atom on the tertiary amine thus may add a linking group, forming a quaternary ammonium group, which together with the sulfonic acid group may constitute a zwitterionic compound. Similar to sultone, the carbon atom linked to the oxygen atom in the cyclic phosphate may undergo a ring-opening reaction by accepting attack of a tertiary nitrogen atom, thereby causing the tertiary nitrogen atom to become a quaternary ammonium group, and constitute a zwitterionic compound together with the phosphoric acid group. The ring of the acid lactone compound such as propionate or butyrolactone may be relatively easy to open the ring due to the small count of atoms and the large ring tension. Therefore, in the presence of a nucleophilic tertiary nitrogen atom, a ring opening reaction may also occur to form a quaternary ammonium group, and a carboxyl group is formed simultaneously to form a zwitterionic compound. Among compounds such as $X(CH_2)_wCOO^-M_t^+$ and $X(CH_2)_wSO_3^-M_t^+$, the halogen atom such as Cl atom, Br atom, and I atom may have a large electronegativity, the bond formed with the carbon atom may be weak and easily leave, and the carbon atom connected to it may also be vulnerable to nucleophiles. Therefore, under the attack of a tertiary nitrogen atom, a C—N bond may be formed to form a quaternary ammonium group, and a zwitterionic compound may be formed with a carboxyl group or a sulfonic acid group. Similarly, carboxylic acid metal salts substituted by other leaving groups may undergo a similar nucleophilic substitution reaction, and other leaving groups may include, but not be limited to, p-toluenesulfonyl (-OTs), methylsulfonyl (-OMs), and trifluoromethanesulfonyl (-OTf).

Solvents for the preparation of antibacterial compound may include but not be limited to organic solvents such as ethers, ketones, aromatics, nitriles, esters, and amides. The solvent itself may also be a mixture of several solvent components, such as a mixture of two or more of the above solvents, or the like. Solvent selection may be affected by the solubility of the reactants, the reaction temperature, and the chemical reactivity of the solvent itself. In general, solvents which are easily reacted with —N=C=O group, such as water, alcohols, amines, and carboxylic acids, may not cooperate as a solvent for the reaction. Therefore, the solvent used in some embodiments may require pre-dehydration or alcohol removal.

Further preferably, the ether solvent may be tetrahydrofuran (THF), 1,4-epoxycyclohexane, ethylene glycol dimethyl ether, tetrahydropyran, or the like; the ketone solvent may be acetone, methyl ethyl ketone, cyclohexanone, acetophenone, phorone, or the like; the aromatic compound may be toluene, pyridine, imidazole, or the like; the ester solvent may be ethyl acetate, n-propyl acetate, n-butyl acetate, methyl formate, ethyl formate, or the like; the nitriles may be acetonitrile, propionitrile, benzonitrile, or the like; the amides may be N-methylpyrrolidone, N,N-dimethylformamide, N,N-dimethylacetamide, or the like.

The above are merely examples of common solvents that can be used in the present reaction, and are not intended to limit the range of reaction solvents. In fact, any aprotic solvent that may dissolve the reaction raw material may be used as a reaction solvent, for example, ethylene carbonate, trimethylene carbonate, or the like.

The stirring method used in the process for preparing the antibacterial hydrophilic compound may be mechanical agitation or magnetic stirring, etc., which may achieve sufficient contact of the reactants. The addition of the reactant solution may be by manual addition or by dripping with a mechanical drip machine. The drop rate may be constant or may change continuously as the reaction progresses. The separation of the final product may be carried out by different separation methods for different product forms. If the crew product obtain from the reaction is a non-precipitate, it may be purified by extraction or distillation; if it is precipitated, it may be purified by centrifugation or filtration.

When the group Q is a structure represented by the formula $(D_2)$, and T is $—R_{23}-A^\ominus$, the antibacterial hydrophilic compound may be prepared by the following method:

(1) reacting the compound $L_1'$ or $L_2'$ represented by the following structural formulas with pyridine having the general formula (I) to obtain a mixture;

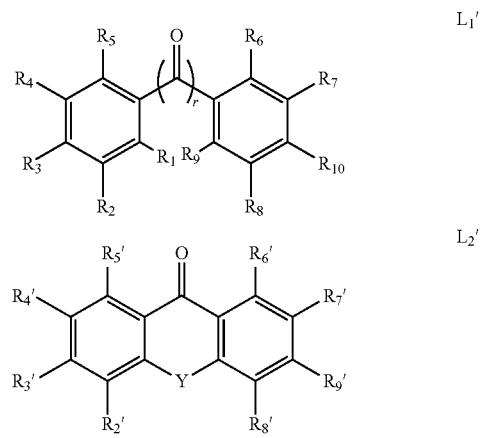

where r may be 1 or 2; Y may be one of single bond, oxygen atom, sulfur atom, selenium atom, —C(O)— group, —SO₂— group, —NH— group, and $C_{1-3}$ alkylene group; $R_1$-$R_{10}$ and $R_2'$-$R_9'$ may be independently selected from hydrogen atom, halogen atom, monovalent polar group, and a substituted monovalent $C_{1-18}$ hydrocarbyl group, and at least one of $R_1$-$R_{10}$ or $R_2'$-$R_9'$ may carry —NCO groups or —NCS groups;

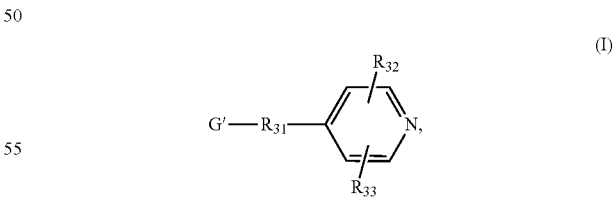

where G' may be selected from —OH group, NH₂ group, or —SH group, $R_{31}$ may be selected from a divalent unsubstituted/substituted $C_{1-18}$ hydrocarbyl group, and $R_{32}$-$R_{33}$ may be independently selected from hydrogen atom, halogen atom, monovalent polar group, and a substituted monovalent $C_{1-18}$ hydrocarbyl group;

(2) reacting the mixture and a compound with the compound E to obtain a zwitterionic type of the antibacterial hydrophilic compound:

the compound E may be selected from sultone, carboxylic acid lactone, $X(CH_2)_wCOO^-M_t^+$, $X(CH_2)_wSO_3^-M_t^+$, and cyclic phosphate; where X may be selected from Br atom, Cl atom, and I atom, w may be an integer not less than 1, $M_t^+$ ion may be selected from $Li^+$ ion, $Na^+$ ion, $K^+$ ion, $NH_4^+$ ion, $Ag^+$ ion, ½ $Mg^{2+}$ ion, and ½ $Ca^{2+}$ ion; and cyclic phosphate may have a structure represented by the following formula:

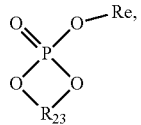

where Re may be selected from a monovalent unsubstituted/substituted $C_{1-6}$ alkyl, cycloalkyl, or aryl group, and $R_{23}$ may be selected from a divalent unsubstituted/substituted $C_{1-18}$ hydrocarbyl group.

In the first step of the reaction, the nitrogen atom in the pyridine compound of the formula (I) may not participate in the reaction, and the function of the pyridine compound of the structure of the general formula (I) may provide a nucleophilic functional group G' (—OH group, $NH_2$ group, or —SH group). The atoms with higher electronegativity (O atom, S atom, N atom) in the group G' may have lone pair electrons and have nucleophilicity. The carbon atom(s) on the functional group —NCO or —NCS of the compound $L_1$' or $L_2$' may be particularly susceptible to occur an addition reaction with the nucleophilic group due to high electron deficient, resulting in —NH—C(O)—NH—* group, —NH—C(S)—NH—* group, —NH—C(S)—O—* group, —NHCOO*-(urethane) group, —NHCOS-(thiocarbamate) group, etc. The nitrogen atom in the pyridine compound of the structure of the general formula (I) may be a precursor of the quaternary ammonium salt structural unit in the final antibacterial hydrophilic compound. In the second step reaction, the pyridine nitrogen atom may become a quaternary nitrogen atom due to the formation of a new C—N bond, that is, a pyridine quaternary ammonium salt structure.

That is, when the group Q is a structure represented by the formula ($D_2$), and T is —$R_{23}$-$A^\ominus$, the group D may have the following group Z, where the group Z may be —NH—C(O)—NH—* group, —NH—C(S)—NH—* group, —NH—C(S)—O—* group, —NHCOO*— group, and an end of the group Z with "*" may be connected to a side of the group Q. Further, the group D may be —R'—Z, and R' may be a substituted/unsubstituted divalent $C_{1-18}$ hydrocarbyl group.

Specifically, the group D may be —$CH_2$—NH—C(S)—O—$CH_2$— group or —$CH_2$—NH—C(S)—NH—* group.

Exemplary pyridines may include, but not be limited to, 4-hydroxymethylpyridine, 4-aminopyridine, 4-mercaptopyridine, 2,6-dimethyl-4-aminopyridine, or the like. The hydrogen atom on the pyridine ring may be replaced by halogen atom (—F, —Cl, —Br, —I atoms) or pseudohalogen (—CN group, —SCN group, —OCN group, etc.), alkoxy group (—$OCH_3$ group, —$OCH_2CH_3$ group, —OPr group, etc.), a group such as —NO group and —$NO_2$ group, or an $C_{1-7}$ alkyl or aryl group. The count of substituents may be at most 7.

In the presence of alkaline reagents (such as tertiary amines, phosphines), the hydrogen atom in the functional group G' may also be removed as a hydrogen ion, and the formed negative ions may further enhance the nucleophilicity of atoms such as O atom, S atom, and N atom in the functional group G', and thus may be utilized as a catalyst. In the presence of a Lewis acid, such as a metal ion or an organometallic compound, the oxygen atom in the isocyanate group may form a coordinate bond with the Lewis acid, and a portion of the electron may be transferred from the oxygen atom to the metal atom, thereby further increasing the electropositivity of the isocyanate group carbon atom, which is beneficial to the attack of the nucleophile, so this type of Lewis acid may also be used as a catalyst.

In some cases, it may be possible to directly cause the reactant E to react with the pyridine substituted by a terminal amino group, a terminal hydroxyl group, or a terminal thiol group without adding a catalyst.

The reaction of the pyridine of the formula (I) with the compound $L_1$' or $L_2$' may be carried out in the presence of a catalyst; preferably, the catalyst may be one or more of an organic amine compound, a phosphine compound, and a metal-containing catalyst.

The organic amines may be divided into several categories: aliphatic amines, such as N,N-dimethylcyclohexylamine, bis(2-dimethylaminoethyl)ether, N,N,N',N'-tetramethylalkylene diamine, triethylamine, N,N-dimethylbenzylamine, etc.; alicyclic amines, including triethylenediamine (fixed amine, DABCO), N-ethylmorpholine, N-methylmorpholine, N,N'-diethylpiperazine, and dimethylaminocyclohexane; aromatic amines, including N,N-dimethylaniline, pyridine, 4-dimethylaminopyridine (N,N-lutidine), etc. The commonality of these amine compounds may be that they are all basic and may accelerate the progress of the reaction. At the same time, they all contain a tertiary nitrogen atom or a pyridine nitrogen atom, so they may not contain an active N—H bond or an O—H bond and may not react with isocyanate.

The phosphine compound, similar to the amine compound, may also act as a base to accelerate the reaction. The Phosphine compounds may include, but not be limited to, various tertiary phosphines, where the three organic groups replacing the three hydrogen atoms may be identical or may not be identical. The tertiary phosphine substituted by three identical organic groups may include but not be limited to, triphenylphosphine, trimethylphosphine, triethylphosphine, tri-n-propylphosphine, triisopropylphosphine, tri-n-butylphosphine, tri-tert-butylphosphine, etc. The tertiary phosphine substituted by the different organic groups may include but not be limited to, dimethylphenylphosphine, methyl diphenylphosphine, diethylphenylphosphine, ethyl diphenylphosphine, etc.

Since metal ions typically may form complexes with oxygen atoms in the isocyanate group, the metal-containing catalysts may result in the electrons on the oxygen atom transferring to the metal atom, increasing the electrical polarity of the carbon atom connected to it, making it easier to accept the attack of the nucleophile. The metal-containing catalysts may include, but not be limited to, inorganic salts, carboxylates, phenates, metal alkyl compounds, or the like containing metals, where the carboxylate may be further divided into a linear or branched alkanoate and a cyclic naphthenate. The metal elements contained may mainly include alkali metals (lithium, sodium, potassium, rubidium, cesium, etc.), alkaline earth metals (magnesium, calcium, strontium, barium), transition metals (uranium, thorium, titanium, zirconium, vanadium, chromium, molybdenum, manganese, iron, cobalt, nickel, copper, zinc, cadmium, mercury, etc.), aluminum, gallium, indium, antimony, tin, lead, antimony, antimony, etc., but not limited to these.

Commonly used metal-containing catalysts may include, but not be limited to, lithium acetate, lithium octoate, lithium naphthenate, sodium trichlorophenolate, sodium stearate, potassium acetate, potassium octoate, calcium acetate, calcium octoate, bismuth naphthenate, cerium acetate, uranyl nitrate, cerium nitrate, titanium tetrachloride, dibutyl titanium dichloride, tetrabutyl titanium, butoxy titanium trichloride, zirconium naphthenate, zirconium octoate, vanadium trichloride, chromium naphthenate, molybdenum hexacarbonyl, manganese octoate, iron trichloride, iron octoate, iron triacetylacetonate, ferrocene, cobalt octoate, cobalt naphthenate, ruthenium oleoreate, cobalt benzoate, nickel pentoxide, nickel octoate, nickel naphthenate, copper acetate, copper octoate, copper naphthenate, zinc octoate, zinc naphthenate, cadmium nitrate, cadmium naphthenate, diphenylmercury, mercury naphthenate, triphenylaluminum, aluminum stearate, gallium acetate, indium naphthenate, bismuth octoate, tin tetrachloride, tetrabutyltin, tributyltin chloride, butyltin dichloride, butyltin trichloride, tributyltin cyanide, dibutyltin dilaurate, dibutyltin diacetate, dibutyltin dioctoate, tributyltin octoate, diphenyltin dioctoate, dibutyltin dibutoxide, dibutyltin diacetylacetonate, di(isooctyl maleic acid) dibutyltin, tin dioctoate, dibutyltin sulfide, stannous octoate, stannous oleate, stannous tartrate, lead benzoate, lead octoate, lead oleate, lead naphthenate, antimony trichloride, antimony pentachloride, triphenylsulfonium dichloride, triphenylsulfonium, phosphonium naphthenate, diethylhydrazine acetate, etc.

Preferably, the catalyst may be a metal containing catalyst. Further preferably, the metal-containing catalyst may be at least one selected from tin tetrachloride, tetrabutyltin, tributyltin chloride, butyltin dichloride, butyltin trichloride, tributyltin cyanide, and dibutyltin diacetate, dibutyltin dioctoate, tributyltin octoate, diphenyltin dioctoate, dibutyltin dibutoxide, dibutyltin diacetylacetonate, dibutyltin di(isooctylmaleate), tin oxide dicaprylate, dibutyltin sulfide, stannous oleate, stannous tartrate, dibutyltin dilaurate, stannous octoate, and naphthenic acid metal salts. Still further preferably, the metal-containing catalyst may be a metal naphthenate. Still more preferably, the metal naphthenate may be at least one selected from copper naphthenate, zinc naphthenate, lead naphthenate, lithium naphthenate, cobalt naphthenate, nickel naphthenate, cadmium naphthenate, mercury salt of naphthenate, indium naphthenate, and bismuth naphthenate.

Similarly, when the group Q is a structure represented by the formula (D1) and T is $R_{13}$, the compound $L_1'$ or $L_2'$ having a tertiary amine group (for example, containing -D-N($R_{11}$)($R_{12}$) (at least one of $R_1$-$R_{10}$ or $R_2'$-$R_9'$ is -D-N($R_{11}$)($R_{12}$)), or may also be obtained by reacting the compound L' with —NCO groups or —NCS groups with a quaternary ammonium salt

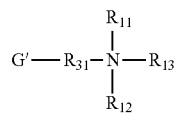

having an active group G', where G' may be —OH group, —SH group, or —NH$_2$ group.

At this time, the group D may have the following group Z, where Z may be —NH—C(O)—NH—* group, —NH—C(S)—NH—* group, —NH—C(S)—O—* group, —NHCOO*— group, and an end of the group Z with "*" may be connected to a side of the group Q.

Halogen-Type Antibacterial Compound

In some embodiments of the present disclosure, an antibacterial compound is provided, where the structural formula of the antibacterial hydrophilic compound may be represented by L-D-Q, where at least one end of the group L is linked to the group Q through the linking group D, where the group L may have a structure represented by the following formula ($L_1$), ($L_2$), ($L_3$), or ($L_4$), the is a divalent $C_{1-18}$ hydrocarbyl group that is unsubstituted or substituted, which includes or does not include a linking group including heteroatom(s); the heteroatom(s) may be at least one of O, S, N, Si, and P atoms; the group Q may be selected from a halamine group represented by the following formula ($B_1$), ($B_2$), ($B_3$), or ($B_4$):

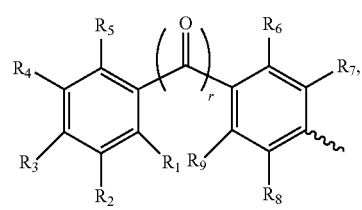

(L$_1$)

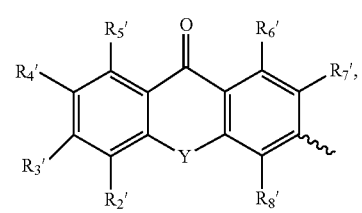

(L$_2$)

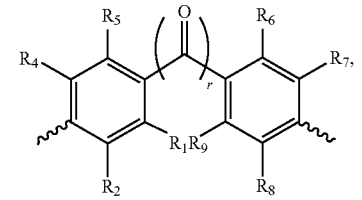

(L$_3$)

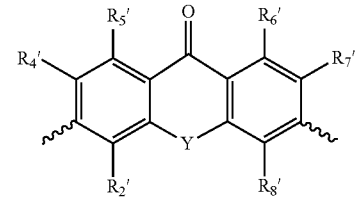

(L$_4$)

where r may be 1 or 2; Y may be one of single bond, oxygen atom, sulfur atom, selenium atom, —C(O)— group, —SO$_2$— group, —NH— group, and C$_{1-3}$ alkylene group; $R_1$-$R_9$ and $R_2'$-$R_8'$ are independently selected from hydrogen atom, halogen atom, monovalent polar group, and a monovalent substituted/unsubstituted $C_{1-18}$ hydrocarbyl group;

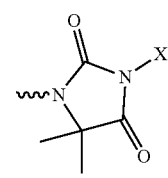

(B$_1$)

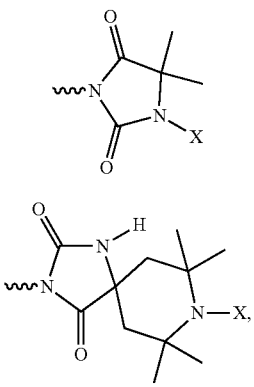

where X may be selected from chlorine, bromine, or iodine, and an end of the group Q with "〰" may be connected to the linking group D.

When the group Q is the halamine group, the obtained antibacterial compound may be a haloamine type, and the antibacterial hydrophilic compound may be imparted with an antibacterial function. In the process of killing harmful microorganisms in the antibacterial antibiotic system, the oxidized halogen atom in the molecule may be consumed, causing the N—X bond in the haloamine molecule to be converted into N—H bond and losing the antibacterial activity, but after a simple rinsing with a very dilute bleaching solution (the active ingredient is a hypohalite), the N—H bond may be oxidized to N—X to regain the bactericidal function. That is, the antibacterial hydrophilic compound may have the characteristics of reproducible antibacterial properties.

In some embodiments, the group D may be a substituted divalent $C_{1-18}$ hydrocarbyl group that includes a linking group including heteroatom(s), a substituted divalent $C_{1-18}$ hydrocarbyl group that does not include a linking group including heteroatom(s), or an unsubstituted divalent $C_{1-18}$ hydrocarbyl group.

Preferably, the group D may be an alkylene having a count of carbon atoms number of 1-10 (i.e., the group D is $—(CH_2)_p—$, and p is an integer of 1-10).

Preferably, the group D may have the following group Z, where Z may be $—NH—C(O)—O—CH_2—*$ group, $—NH—CH_2—CH(OH)—(CH_2)_q—*$ group, $—S—CH_2—CH(OH)—(CH_2)_q—*$ group, or $—O—CH_2—CH(OH)—(CH_2)_q—*$ group, where q may be an integer from 1 to 6, and an end of the group Z with "*" may be connected to a side of the halamine group.

Preferably, the group D may have the following group Z, where Z may be $—NH—C(S)—O—CH_2—*$ group, $—C(O)—O—CH_2—*$ group, $—SO_2—O—CH_2—*$ group, $—O—CH_2—*$ group, or $—CH(OH)CH_2—O—CH_2—*$ group, and an end with "*" is connected to a side of the halamine group.

The "group D with the following group Z" may be understood as the group D may equal to Z (the other side of Z is directly connected to L), or the group D may be $—R'—Z$ and R' may be a substituted/unsubstituted divalent $C_{1-18}$ hydrocarbyl group. Preferably, R' may be $—(CH_2)_p—$ group or $—O—CH_2—$ group, and p may be an integer from 1 to 10.

For example:

Reaction formula (1)

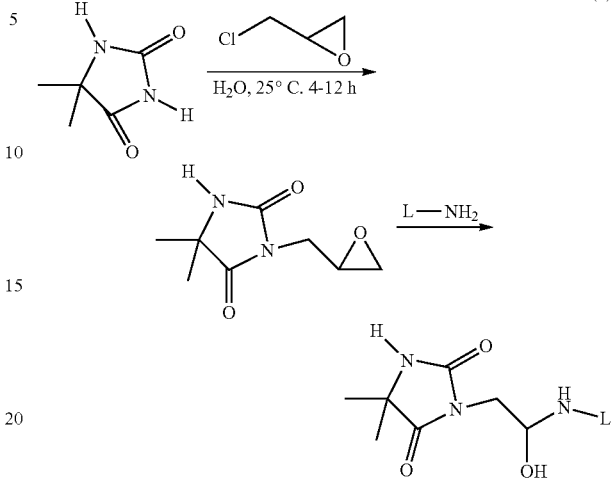

The reaction product of the reaction formula (1) may correspond to the structural form of L-D-B$_2$, and the second step of the reaction formula (6) may be a reaction of a halogen amine compound having a terminal epoxy group $—CH(O)CH_2$ with the compound $L_1'$ or $L_2'$ having an active group $Z^2$ ($Z^2$ may be $—NH_2$ group, or may also be other active group ($—OH$ group, $—SH$ group, etc.) reacting with epoxy groups). Correspondingly, the group Z in the group D may be $—NH—CH_2—CH(OH)—(CH_2)_q—*$ group, $—S—CH_2—CH(OH)—(CH_2)_q—*$ group, or $—O—CH_2—CH(OH)—(CH_2)_q—*$ group.

Similarly, the reaction product of the following reaction formula (2) may also correspond to the structural form of L-D-B$_2$.

Reaction formula (2)

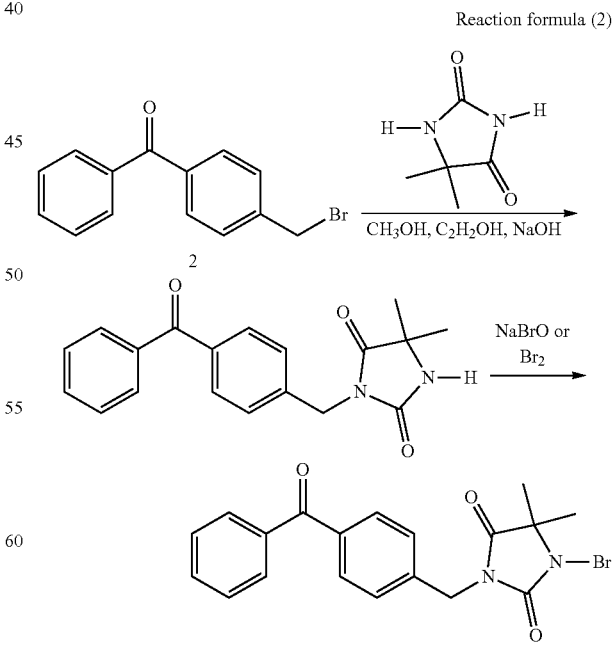

As another example, the reaction formula may be represented as the following reaction formula (3), Reaction formula (3)

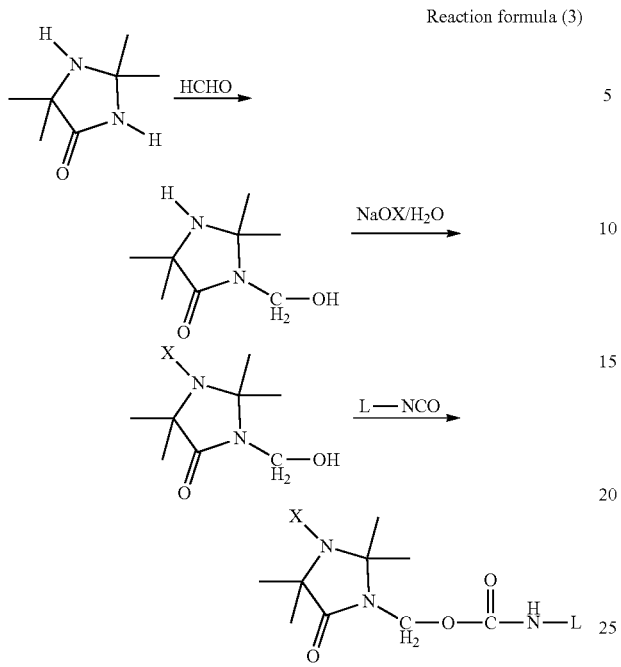

Reaction formula (4)

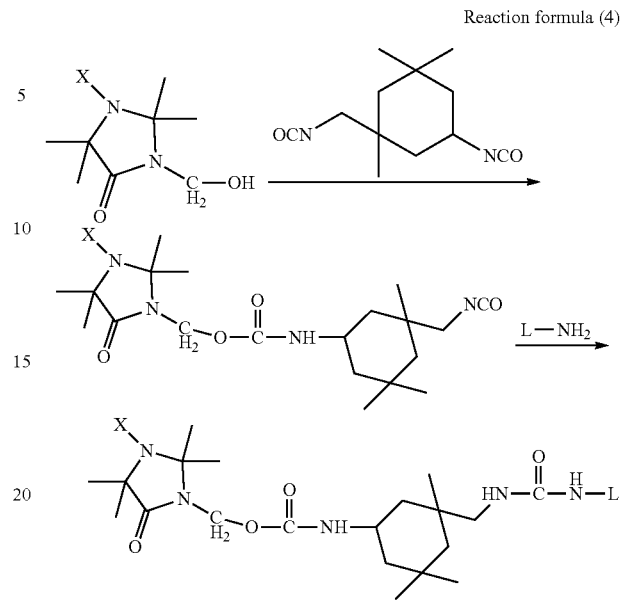

The reaction product of the reaction formula (3) may correspond to the structural formula of L-D-B$_3$, and the third step may be a reaction of a halogen amine compound having —CH$_2$OH with the compound L$_1$' or L$_2$' having an active group Z$^2$ (Z$^2$ may be —NCO group, and may also be —NCS group, —COX group, —COOH group, —SO$_2$X group, —RX group, or —CH(O)CH$_2$ group, where X—Cl, —Br, or —I group). Correspondingly, the group Z in the group D may also be —NH—C(S)—O—CH$_2$—* group, —C(O)—O—CH$_2$—* group, —SO$_2$—O—CH$_2$—* group, —O—CH$_2$—* group, —CH$_2$—* group, —CH(OH)CH$_2$—O—CH$_2$—* group, and the end with * in the group Z may be connected to a side of the halamine group.

Specifically, when the group Z$^2$ is —NCO group, the group Z formed by reacting with —CH$_2$—OH may be —NH—C(O)—O—CH$_2$—* group; when the group Z$^2$ is —NCS group, the group Z formed by the reaction with —CH$_2$—OH group may be —NH—C(S)—O—CH$_2$—* group; when the group Z$^2$ is —COX group or —COOH group, the group Z formed by the reaction with —CH$_2$—OH group may be —C(O)—O—CH$_2$—* group; when the group Z$^2$ is —SO$_2$X group, the group Z formed by the reaction with —CH$_2$—OH group may be —SO$_2$—O—CH$_2$—* group; when the group Z$^2$ is —X, the group Z formed by reacting with —OH group may be —O—CH$_2$-* group; when the group Z$^2$ is —CH(O)CH$_2$ group, the group Z formed by the reaction with —CH$_2$—OH group may be —CH(OH)CH$_2$—O—CH$_2$—* group.

Similarly, the reaction product of the following reaction formula (4) may also correspond to the structural form of L-D-B$_3$.

The starting materials and other chemical reagents used in the following examples may be commercially available. If necessary, purification may be carried out by means known in the art, such as dehydration of a tertiary amine, removal of oxidizing components from tertiary amines, removal of primary and secondary amines from tertiary amines, etc., and these purifications may usually be carried out by means of distillation, splitting, extraction, addition of a reagent, etc.

The following compounds may be important materials used in the preparation of various types of the antibacterial hydrophilic compounds in the examples of the present disclosure:

19.6 g of 4-methyl-benzophenone with a structural formula of (1)

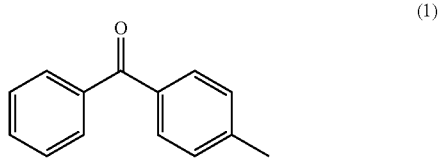

was weighed and added to a 500 mL three-necked flask; 0.5 g of benzoyl peroxide (BPO), 30 g of N-bromosuccinimide (NBS) were added, 200 mL of carbon tetrachloride was added as solvent, the mixture was heated to 85° C. for 24 h, cooled to room temperature, and filtered. The solid obtained was 4-(bromomethyl)-benzophenone (2). The intermediate (2) was dissolved in a mixed solvent of acetone/water, reacted with NaN$_3$ at 60° C. for 3 h, and purified by extraction to obtain an intermediate (3), whose chemical name was 4-azidomethylbenzophenone. If the intermediate (3) was reacted with CS$_2$ in triphenylphosphine (PPh$_3$) and dichloroethane (DCM), the intermediate (4) was obtained, i.e., 4-benzoylbenzyl isothiocyanate. When the intermediate (3) was hydrolyzed in triphenylphosphine, the primary amino group-containing intermediate (5) was obtained, that was, 4-aminomethylbenzophenone. The intermediate (4) was also obtained by reacting the intermediate (5) with SCl$_2$ in THF. The intermediate (5) was controlled by the reaction with CH$_3$I to obtain a benzophenone (6) containing a tertiary amine. The reaction of each step was shown as follows:

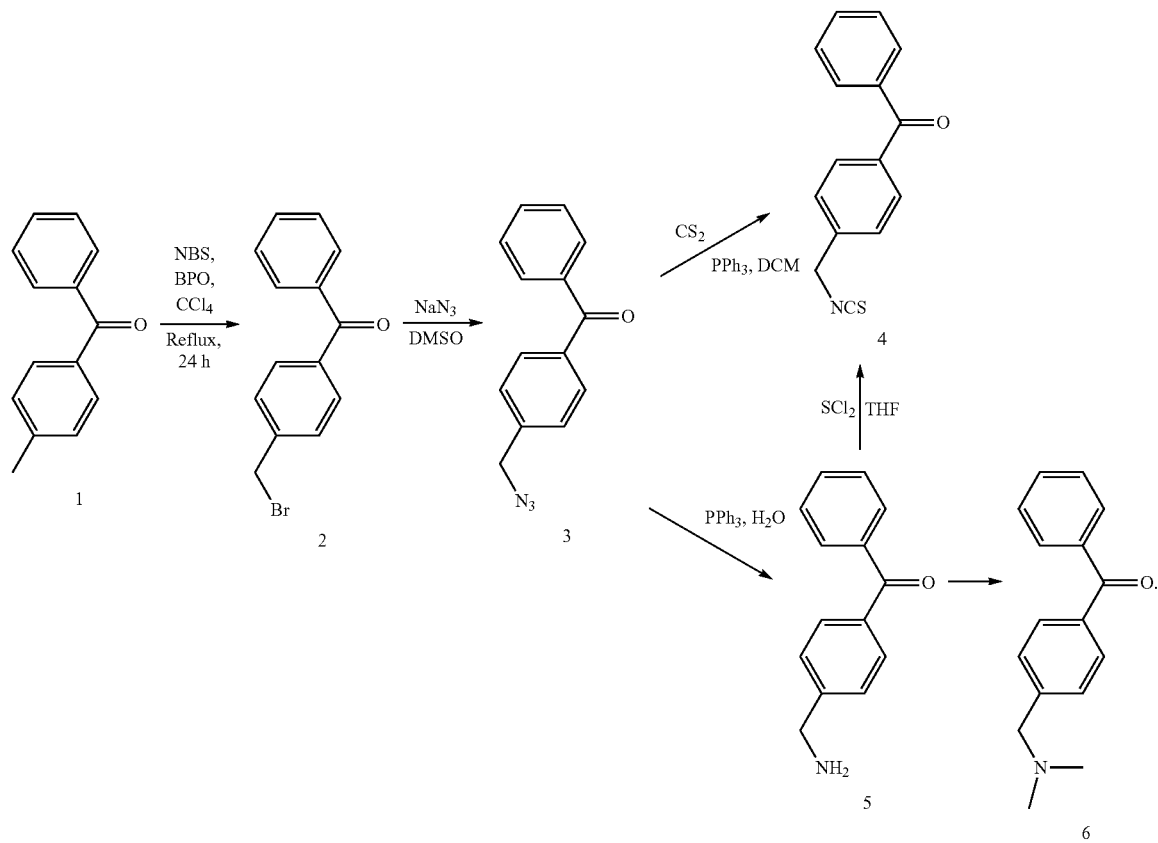

Similarly, 26.8 g of 4,4'-bis(N,N-dimethyl)benzophenone was weighed and its structural formula was

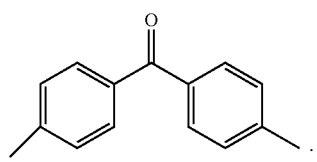

(7)

It was added to a 500 mL three-necked flask, and 0.5 g of benzoyl peroxide (BPO) and 30 g of N-bromosuccinimide (NBS) were added. 200 mL of carbon tetrachloride was added as a solvent, and the mixture was heated to 85° C. for 24 hours, cooled to room temperature, and filtered to obtain a solid of 4-di(bromomethyl)-benzophenone (8). (8) was reacted with $NaN_3$ in DMSO solvent at 80° C. for 6 h, and purified by extraction to obtain an intermediate (9). The intermediate (9) was reacted with $CS_2$ in triphenylphosphine ($PPh_3$) and dichloroethane (DCM) to obtain a benzophenone (10) containing a diisothiocyanate. If the intermediate (9) was hydrolyzed in triphenylphosphine, a benzophenone (11) containing a bisamino group was obtained. The intermediate (10) was also obtained by reacting (11) with $SCl_2$ in THF. The intermediate (11) was reacted with formaldehyde/ $NaBH_4$ to obtain a benzophenone (12) containing a di-tertiary amino group. The reaction of each step was shown as follows:

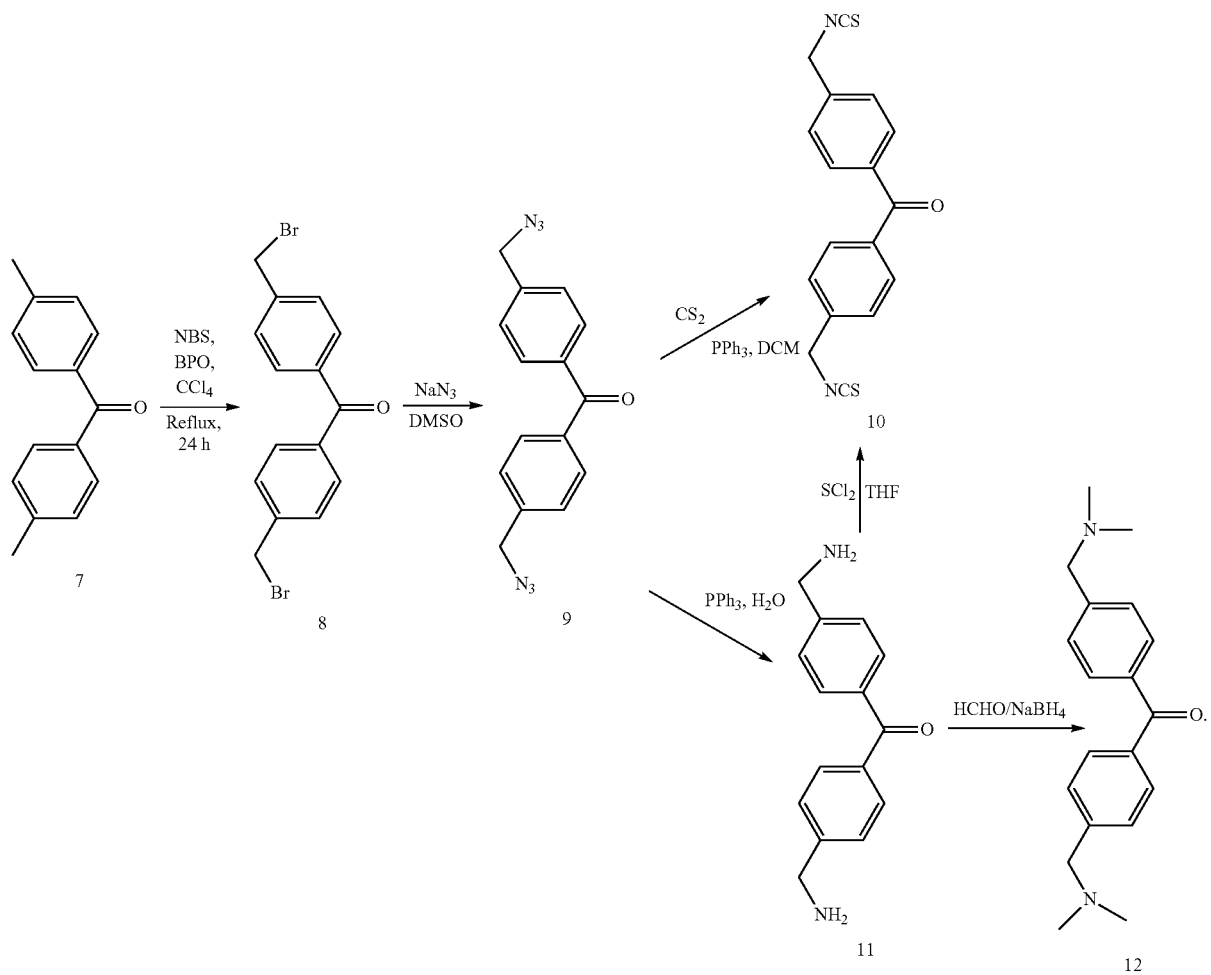

Example 1

26.8 g (0.1 mol) of 4,4'-bis(N,N-dimethylamino)benzophenone was weighed and its structural formula may be

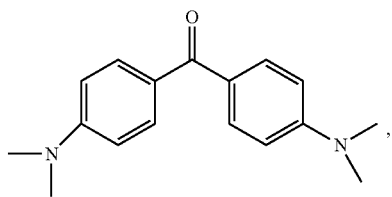

which was added to a round bottom flask with mechanical stirring. 24.4 g (0.2 mol) of propane sultone (referred to as 1,3-PS, structural formula is

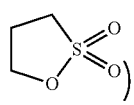

dissolved in 200 mL of anhydrous THF was added dropwise at 50° C. After the completion of the dropwise addition, the reaction was continued for 1 hour to obtain a precipitate, which was purified by centrifugation several times to obtain 50.2 g of a zwitterionic antibacterial compound containing a xylene ketone group represented by the following formula, which had a light hydrogen abstraction activity. The reaction formula was as follows:

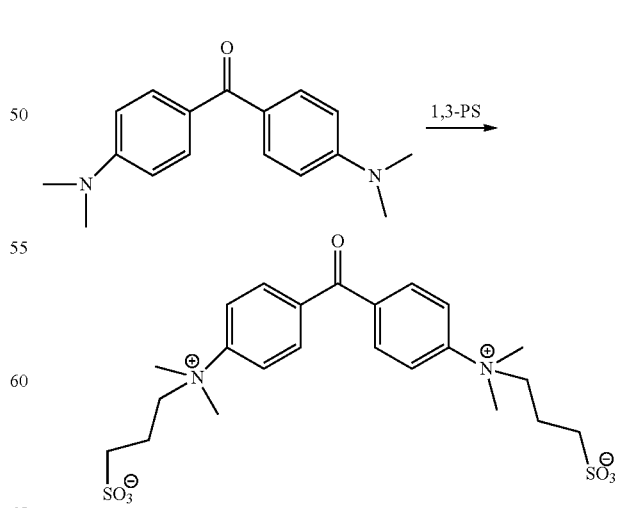

The nuclear magnetic data of the antibacterial hydrophilic compound obtained in this example was as follows: δ (ppm)

7.86 (d, 2H), 7.79 (d, 2H), 7.74 (d, 2H), 7.58 (t, 2H), 3.73 (m, 12H), 3.40 (s, 4H), 3.0 (m, 4H), 2.24 (t, 2H). $^{13}$C-NMR (D$_2$O, 600 MHz). δ (ppm) [195.7, 150.2, 139.6, 133.3, 133.1, 131.4, 130.4, 120.9, 67.2, 52.1, 49.6, 46, 20.7].

The antibacterial hydrophilic compound obtained in the present example may be modified to provide a durable antibacterial, hydrophilic, and antifouling function after modifying the chemical fiber fabric such as polyester.

Example 1 used a compound L having a tertiary amine group to react with a sultone. Similar sultones may also be ethane sultone, butane sultone, 2,4-butane sultone

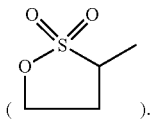

( ).

A similar cyclic lactone may also be cyclic phosphate (e.g., 2-ethoxy-2-oxo-1,3,2-dioxaphosphane

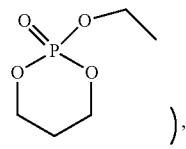

), carboxylic lactone (e.g., β-propiolactone

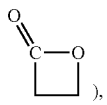

), or the like to give a zwitterionic antibacterial compound (see Examples 2-4), or the lactone may also be substituted with a halosulfonate or a halocarboxylate for reacting with a tertiary amine L to obtain a zwitterionic compound (see Examples 5-6).

Further, a similar tertiary amine group-containing compound L may include (6)

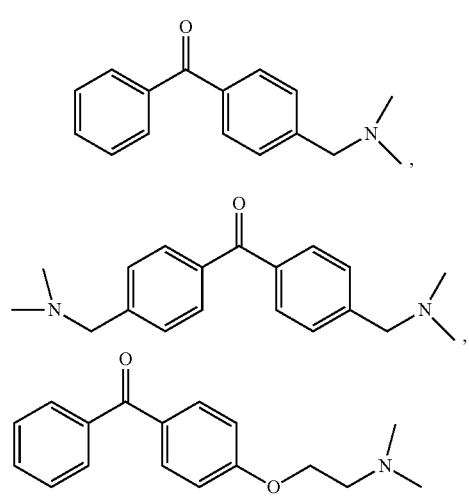

(12)

(the raw material in Examples 2),

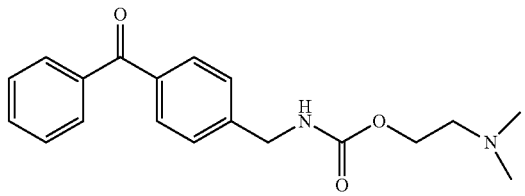 [SMILES: CN(C)CCOC(=O)NCc1ccc(C(=O)c2ccccc2)cc1]

(the raw material in Example 5),

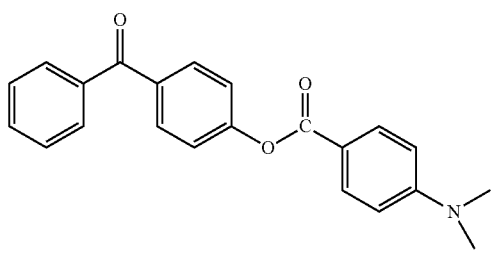 [SMILES: CN(C)c1ccc(C(=O)Oc2ccc(C(=O)c3ccccc3)cc2)cc1]

(the raw materials in Examples 4 and 13),

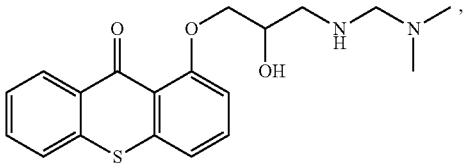 [SMILES: CN(C)CNCC(O)COc1cccc2sc3ccccc3c(=O)c12]

or the like. Correspondingly, in the finally obtained zwitterionic antibacterial compounds of the L-D-D1 type, the group D may be —CH$_2$— group, —O—CH$_2$—CH$_2$— group, —CH$_2$—NH—COO—CH$_2$—CH$_2$— group, —O—CO-Ph group, —O—CH$_2$—CH(OH)—CH$_2$—NH—CH$_2$— group, etc.

Example 2

0.2 mol of the compound 4-[2-(dimethylamino)ethoxyxylene (7) was weighed and added to a round bottom flask with mechanical stirring. 0.2 mol of 1,4-butane sultone (1,4-BS) dissolved in 400 mL of anhydrous THF was added dropwise at 40° C. After the completion of the dropwise addition, the reaction was continued for 12 hours to obtain a precipitate, which was purified by centrifugation several times to obtain 78.5 g of the zwitterionic antibacterial compound shown below, and its chemical reaction formula was as follows:

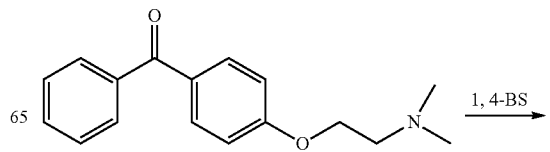

-continued

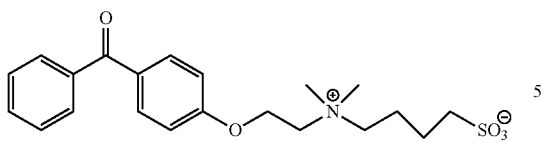

Example 3

0.2 mol of compound (6) was weighed and added to a round bottom flask with mechanical stirring. 0.2 mol of cyclic phosphate-2-ethoxy-2-oxo-1,3,2-dioxaphospholane (referred to as EOP) dissolved in 400 mL of anhydrous THF was added dropwise at 75° C. After the completion of the dropwise addition, the reaction was continued for 12 hours to obtain a precipitate, which was purified by centrifugation several times to obtain 61.6 g of the zwitterionic antibacterial compound shown below, and its chemical reaction formula was as follows:

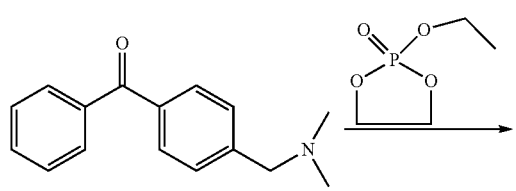

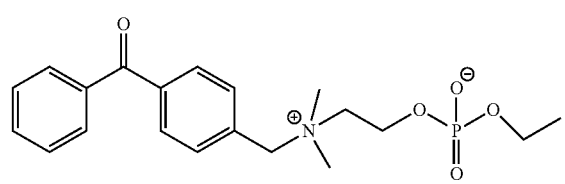

Although THF is used as the organic solvent in some embodiments, acetonitrile, DMF, DMSO, anhydrous butanone, anhydrous acetone, cyclohexanone, toluene, ethyl acetate, n-propyl acetate, n-butyl acetate, acetonitrile, 1,4-epoxycyclohexane, N-methylpyrrolidone, pyridine, N,N-dimethylformamide or a mixture of two or more solvents may also be used.

In addition, for the compound (6) with tertiary amine groups reacting with propane sultone

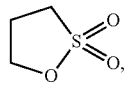

cyclic phosphate (e.g., 2-ethoxy-2-oxo-1,3,2-dioxaphosphane

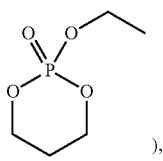

), carboxylic lactone (e.g. β-propiolactone

and etc. are similar, the stirring and reacting may be carried out at 20 to 80° C. (preferably 30 to 60° C.) for 1 to 24 hours (preferably 6 to 12 hours) using anhydrous THF, acetone, or the like as a solvent. The separation of the final product may also be carried out in different ways for different product forms. If it is an oil, it may be extracted and purified by using a polar aprotic organic solvent (such as DMSO), or by distillation of the solution of the product in an organic solvent; if it is a precipitate, it may be centrifuged or filtered. Further, the reaction with the linear compound E of the general formula $X(CH_2)_wCOO^-M_t^+$, $X(CH_2)_wSO_3^-M_t^+$ may be similar to the above, as described in the following embodiments 5 and 6.

Example 4

34.6 g of 4-N,N-xylenecarboxylic acid-4'-benzoylphenyl ester was dissolved in acetone solvent. Then, 8.0 g of β-propiolactone dissolved in acetone was added, mixed uniformly, reacted at 30° C. for 8 h, and purified by centrifugation several times to obtain 36.5 g of a white precipitated zwitterionic antibacterial compound, and the reaction formula was as follows:

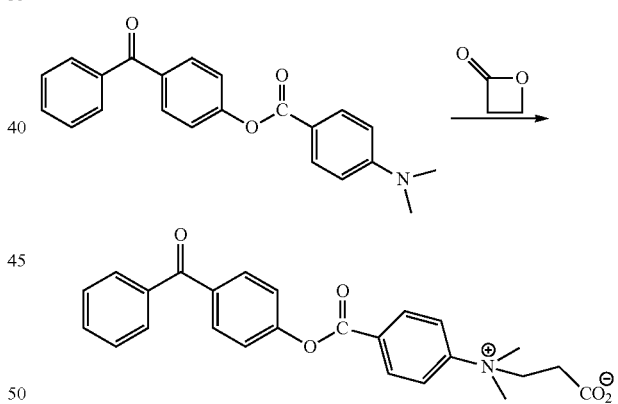

Example 5

0.2 mol of the compounds shown below (2-(dimethylamino)ethyl 4-benzoylbenzylcarbamate) was weighed, and added to a round bottom flask with mechanical stirring. 0.2 mol of sodium chloroacetate ClCH2COONa dissolved in 400 mL of anhydrous THF was added dropwise at 40° C. After the completion of the dropwise addition, the reaction was continued for 8 hours to obtain a precipitate, which was purified by centrifugation several times to obtain 72.1 g of a white solid, that was, a zwitterionic antibacterial compound was obtained, and the chemical reaction formula was as follows:

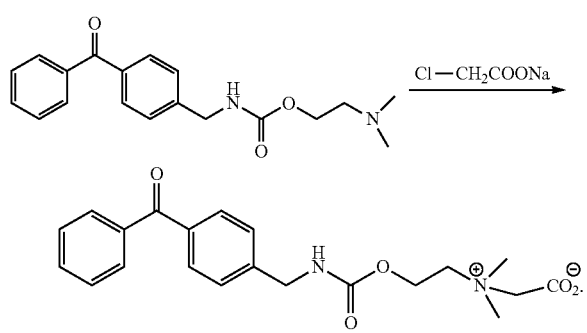

In the reaction, functions of sodium chloroacetate ClCH2COONa may include causing the chlorine atom to leave to form a quaternary ammonium group by a nucleophilic attack of the tertiary amine N atom. The quaternary ammonium group and a carboxyl group constitute a zwitterionic antibacterial compound. Similarly, other halogens (Br atom, I atom, etc.) or other sodium carboxylates that are easily substituted by group (OTs, OMs, OTf, etc.) may also be sodium bromoacetate, sodium iodoacetate, sodium 2-chloropropionate, sodium 3-chloropropionate, sodium 2-bromopropionate, sodium 3-bromopropionate, sodium 2-iodopropionate, sodium 3-iodopropionate, a halogenated carboxylic acid with a longer carbon chain, or the like.

Example 6

0.2 mol of compound (6) was weighed and added to a round bottom flask with mechanical stirring. 0.2 mol of sodium 2-bromoethanesulfonate BrCH2CH2SO3Na dissolved in 400 mL of anhydrous THF was added dropwise at 20° C. After the completion of the dropwise addition, the reaction was continued for 6 hours to obtain a white precipitate, which was purified by centrifugation several times to obtain 70.1 g of an amphoteric ion-based antibacterial compound. The reaction formula was as follows:

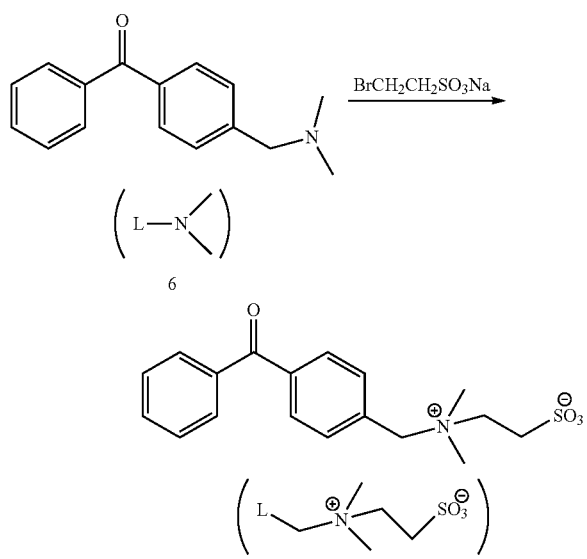

The nuclear magnetic data of the antibacterial hydrophilic compound obtained in some embodiments was as follows:
$^1$H NMR (CD$_3$Cl, 600 MHz, TMS), δ (ppm) 7.86 (d, 2H), 7.79 (d, 2H), 7.74 (d, 2H), 7.58 (t, 1H), 7.46 (t, 2H), 3.73 (s, 6H), 3.40 (m, 2H), 3.0 (m, 2H). $^{13}$C-NMR (CD$_3$Cl, 600 MHz). δ(ppm) [195.7, 150.2, 139.6, 133.3, 133.1, 131.4, 130.4, 128.5, 120.9, 67.2, 52.4, 49.6, 46.0].

Similarly, a halosulfonate which is reacted with a compound L having a tertiary amino group, in addition to sodium 2-bromoethanesulfonate, may also be sodium 2-chloroethanesulfonate, sodium 2-iodoethanesulfonate, sodium 2-chloropropanesulfonate, sodium 2-bromopropanesulfonate, sodium 2-iodopropane sulfonate, sodium 2-p-phenylsulfonylpropane sulfonate, or the like.

Example 7

25.5 g of compound (4) was added to a round bottom flask with mechanical stirring. After adding 0.2 mL of catalyst dibutyltin dilaurate (DBTDL), 11.0 g (0.16 mol) of 4-hydroxymethylpyridine was slowly added dropwise with a dropping funnel under stirring at 30° C. The reaction was continued for 1 h after the completion of the dropwise addition, and further stirred at this temperature for 12 h. Then 12.2 g of propane sultone (1,3-PS) dissolved in 200 mL of anhydrous THF was added dropwise. After the completion of the dropwise addition, the reaction was continued for 1 hour to obtain a crude product, which was purified by centrifugation several times to obtain 42.0 g of the antibacterial hydrophilic compound as shown in the following formula. The chemical reaction formula was as follows:

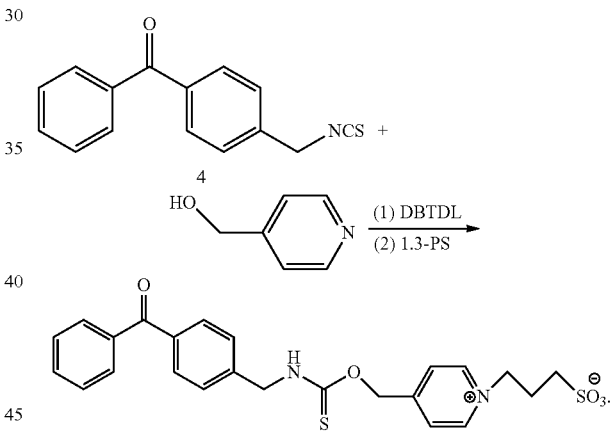

In Example 7, the compound L with —NCS group may be first reacted with a tertiary amine having a hydroxyl group, and then reacted with propane lactone to obtain a zwitterionic antibacterial compound. Similarly, the compound L with —NCS group may be reacted with a pyridine type compound having —NH$_2$ group or —SH group (Example 8), and the compound L with —NCO group may be reacted with a pyridine type compound having —OH group, —NH$_2$ group, or —SH group, also synthesized by the same reaction principle, and then reacted with a sultone to obtain a zwitterionic antibacterial compound. Similar sultones may also include ethane sultone, butane sultone, 2,4-butane sultone

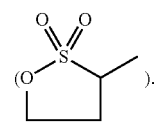

Similar cyclic lactones may also include cyclic phosphates (for example,

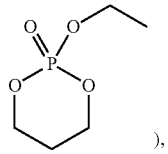

), carboxylic lactones (for example, β-propiolactone

), or the like to obtain a zwitterionic antibacterial compounds. Alternatively, a halogenated sulfonate $X(CH_2)_w SO_3^- M_t^+$ or a halogenated carboxylate $X(CH_2)_w COO^- M_t^+$ may be used in place of the lactone to react with the pyridine-type compound obtained in the first step to obtain the zwitterionic antibacterial compound. The zwitterionic antibacterial compounds may also be prepared directly by the reaction between compounds with other active groups (Examples 9, 10).

Similarly, the quaternary ammonium salt type of the antibacterial compound may be obtained by reacting a compound having —NCS group or —NCO group with a compound having —OH group, —SH group, or the like to obtain a compound having a tertiary amino group. Further, a reaction of a tertiary amino group-containing compound with a halogenated compound may be carried out to obtain a quaternary ammonium salt type of antibacterial compound (Example 11). It may be also possible to directly adopt the reaction principle of a tertiary amine compound and a halogenated compound to obtain a quaternary ammonium salt type of antibacterial compound (Examples 12-17), and may also directly prepare a zwitterionic antibacterial compound by using a reaction between other active groups (Examples 18-19).

Example 8

25.5 g of the compound (4) was added to a round bottom flask with mechanical stirring, and 12.2 g of 2,6-dimethyl-4-aminopyridine was slowly added dropwise with a dropping funnel at 30° C. under stirring. After the completion of the dropwise addition, the reaction was continued for 6 hours, and then 12.2 g of propane sultone (1,3-PS) dissolved in 200 mL of anhydrous THF was added dropwise. After the completion of the dropwise addition, the reaction was continued for 4 hours to obtain a crude product, which was purified by centrifugation several times to obtain 42.3 g of the zwitterionic antibacterial compound as described in the following formula. The chemical reaction formula was as follows:

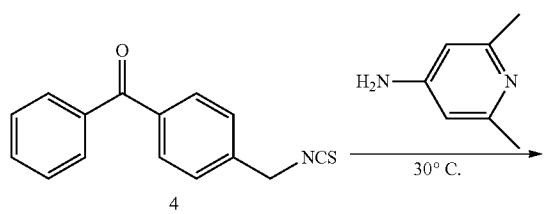

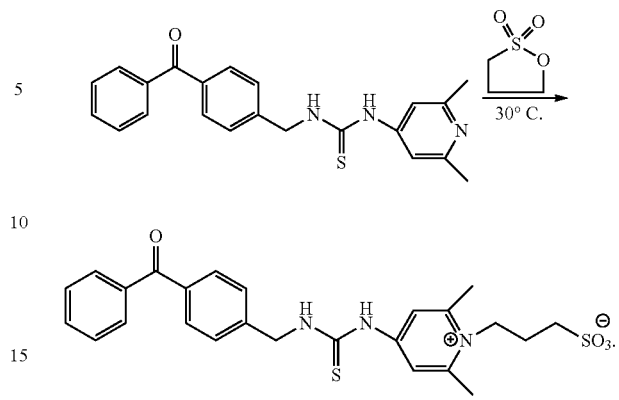

Example 9

28.5 g of 1,4-bis(2,3-epoxy)propoxythiazepine, and 18.6 g of a zwitterionic compound (3-[2-(Aminoethyl)-dimethylamine]propane sulfonate, or amine ethylsulfonic acid type betaine) having a terminal amino group were added to 200 mL of tetrahydrofuran. The ring-opening reaction was carried out at room temperature for 1 h, filtered and washed several times with THF to obtain 55.0 g of the zwitterionic antibacterial compound. The reaction formula was as follows:

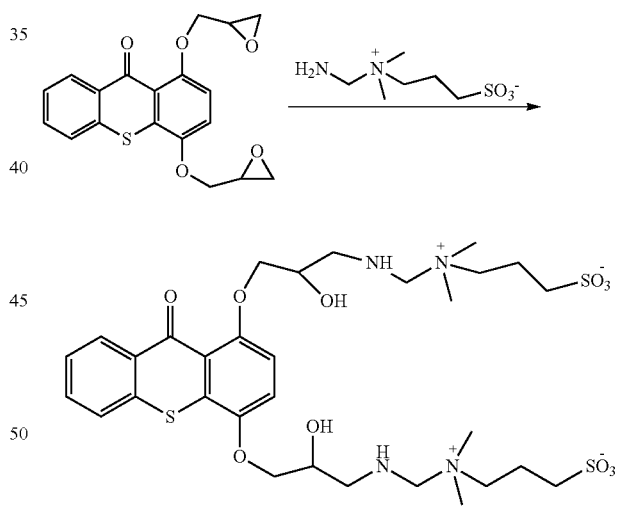

Example 10

19.7 g of 4-aminobenzophenone and 40.0 g of isocyanate-containing zwitterionic compound were weighed (the synthetic method referred to the following application: PCT/CN2015/090059), and added to a 500 ml three-necked flask. 200 ml of dimethyl sulfoxide was added. The reaction was carried out for 5 h at room temperature, and the resultant mixture was centrifuged to obtain 56.2 g of a white antibacterial compound. The reaction formula was as follows:

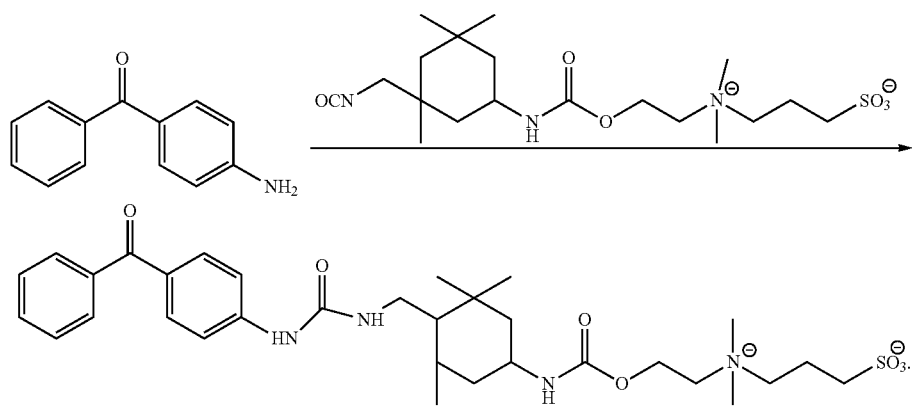

After modifying the chemical fiber fabric such as polyester, the zwitterionic antibacterial hydrophilic compound shown in the embodiments 1-10 may impart the fabric a durable hydrophilic, antibacterial function, and antistatic function, in the case of maintaining its mechanical properties and color. Bacteria may be less likely to adhere to the fabrics, and an anti-fouling effect may be achieved.

Example 11

22.5 of 4-isocyanatobenzophenone was added to a round bottom flask with mechanical stirring. After adding 0.2 mL of catalyst dibutyltin dilaurate (DBTDL), 7.2 g of dimethylethanolamine was slowly added dropwise with a dropping funnel under stirring at 30° C. After the dropwise addition was completed, the temperature was kept constant and the reaction was stirred for 12 hours. Then, 19.3 g of bromooctane (Br—$C_8H_{17}$) dissolved in 300 mL of anhydrous ethyl acetate was added dropwise. After completion of the dropwise addition, the reaction was continued for 1 hour to obtain a crude product which was extracted and purified three times with ethyl acetate to obtain 26.7 g of an antibacterial compound (yellow-yellow viscous liquid) of the following formula, the chemical reaction formula of which was as follows:

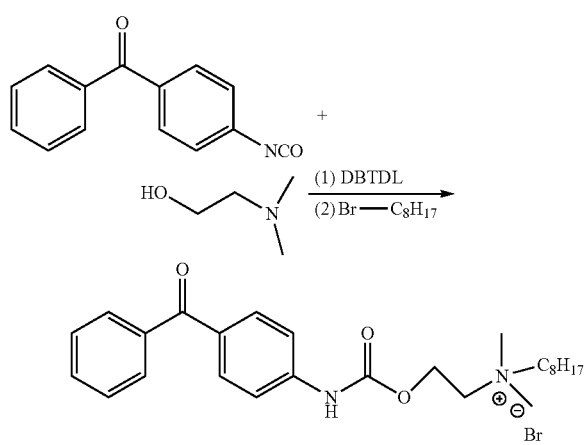

Example 12

26.8 g (0.1 mol) of 4,4'-bis(N,N-dimethylamino)benzophenone was weighed and added to a round bottom flask with mechanical stirring. 50 g of bromododecane (Br—C12H25) dissolved in 400 mL of toluene was added dropwise at 50° C. After the completion of the dropwise addition, the reaction was continued for 1 hour to obtain a precipitate, which was purified by centrifugation several times to obtain 66.5 g of a quaternary ammonium salt type antibacterial compound. And the reaction formula was as follows:

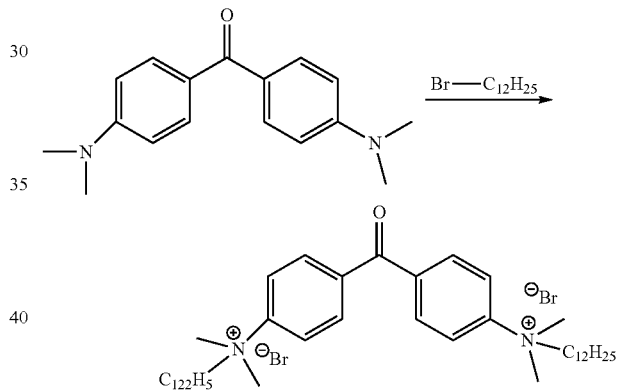

The nuclear magnetic data of the antibacterial hydrophilic compound prepared in this example wa as follows: $^1$H NMR (CD$_3$Cl, 600 MHz, TMS), δ (ppm) 7.86 (d, 2H), 7.79 (d, 2H), 7.74 (d, 2H), 7.58 (t, 2H), 3.73 (s, 12H), 3.54 (m, 4H), 1.30 (m, 8H), 1.22 (m, 32H), 0.83 (t, 6H). $^{13}$C-NMR (CD$_3$Cl, 600 MHz). δ (ppm) [195.7, 139.6, 150.6, 133.3, 133.1, 131.4, 130.4, 130.1, 120.9, 68.0, 54.2, 31.8, 29.6, 29.3, 29.2, 26.3, 22.8, 22.6, 14.0].

Example 13

34.6 g (0.1 mol) of 4-N,N-xylenecarboxylic acid-4'-benzoylphenyl ester (11) was weighed and added to a round bottom flask with mechanical stirring. 26.5 g of bromododecane (Br—$C_{12}H_{25}$) dissolved in 400 mL of toluene was added dropwise at 50° C. After the completion of the dropwise addition, the reaction was continued for 1 hour to obtain a precipitate, which was purified by centrifugation several times to obtain 52.0 g of a quaternary ammonium salt type of antibacterial compound. And the reaction formula was as follows:

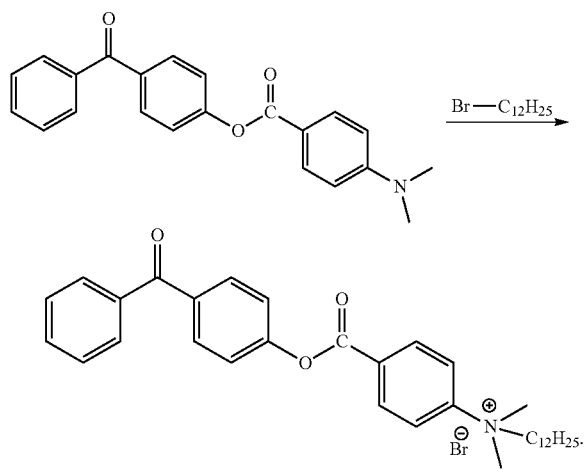

Example 14

27.5 g of compound (2), 4-(bromomethyl)-benzophenone and 21.3 g of dodecyl dimethylamine were weighed. 200 mL of tetrahydrofuran was used as a solvent. The reaction was refluxed for 24 hours, and cooled to room temperature to obtain a crude product. Dichloromethane/methanol (20:1) was used as a developing solvent. The column was purified by a silica gel column, and then distilled through a rotary evaporator to obtain 35.2 g of a pale yellow oil. That was, the quaternary ammonium salt type of antibacterial compound, the reaction formula of which was as follows:

The nuclear magnetic data of the antibacterial hydrophilic compound obtained in this example was as follows: $^1$H NMR (CD$_3$Cl, 600 MHz, TMS), δ (ppm) 7.85 (d, 2H), 7.79 (d, 2H), 7.74 (d, 2H), 7.58 (t, 1H), 7.46 (t, 2H), 5.25 (s, 2H), 3.54 (m, 2H), 3.33 (s, 6H), 1.23 (m, 4H), 1.20 (m, 16H), 0.83 (t, 3H). $^{13}$C-NMR (CD$_3$Cl, 600 MHz). δ (ppm) [195.6, 139.5, 136.5, 133.3, 133.0, 131.3, 130.3, 130.0, 128.4, 66.5, 63.9, 49.7, 31.8, 29.5, 29.3, 29.28, 29.20, 29.16, 26.2, 22.8, 22.6, 14.0].

Example 15

36.8 g of 4,4'-bis(bromomethyl)benzophenone (8) and 22.5 g of N,N-dimethylguanamine were added to a 250 ml three-necked flask, and 100 ml of ethyl acetate solvent was added. The reaction was refluxed for 24 hours, and cooled to room temperature to obtain a crude product which was purified by chloroform/methanol, and then evaporated to dryness to obtain 48.5 g of quaternary ammonium salt type of antibacterial compound. The reaction formula was as follows:

Example 16

2-methylindole (22.3 g), benzoyl peroxide (1.2 g), and N-bromosuccinimide (NBS, 18.0 g) were dissolved in carbon tetrachloride (CCl$_4$, 200 ml). After heating to 85° C. and reacting for 24 hours, the reaction was cooled to room temperature. The solid was filtered and washed with CCl$_4$ three times to obtain 28.5 g of a white solid, that was, 2-(bromomethyl)-oxime.

2-(Bromomethyl)-indole (28.5 g) reacted with N,N-dimethyldecylamine (18.5 g) under reflux for 24 hours. The reaction was cooled to room temperature to obtain a crude product. Dichloromethane/methanol (20:1) was used as a developing solvent. The column was purified by a silica gel column, and then distilled by a rotary evaporator to obtain 26.6 g of a pale yellow oil, that was, the quaternary ammonium salt type of antibacterial compound, the reaction formula of which was as follows:

Example 17

2,4'-bis(dimethylamino)benzil (29.6 g) and N,N-dimethyl-n-octylamine (16.0 g) were weighed and added to a 500 ml three-necked flask. And dimethyl sulfoxide solvent 200 ml was added. The reaction was refluxed for 24 hours, cooled to room temperature, and washed repeatedly with petroleum ether/dimethyl sulfoxide several times to obtain 38.3 g of an oily antibacterial compound. The chemical reaction formula was as follows:

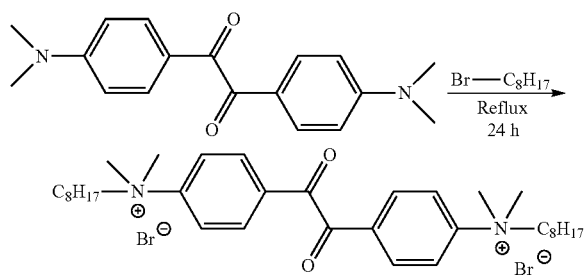

Example 18

23.2 g of 2-amino-4'-chlorobenzophenone and 40.7 g of an isocyanate-containing quaternary ammonium salt compound (the synthetic method referred to the following application: PCT/CN2015/090059) were weighed and added to a 500 ml three-necked flask. 200 ml of dimethyl sulfoxide was added. After reacting for 5 h at room temperature, the reaction was repeatedly extracted by petroleum ether/dimethyl sulfoxide to obtain 58.2 g of an oily antibacterial compound. The chemical reaction formula was as follows:

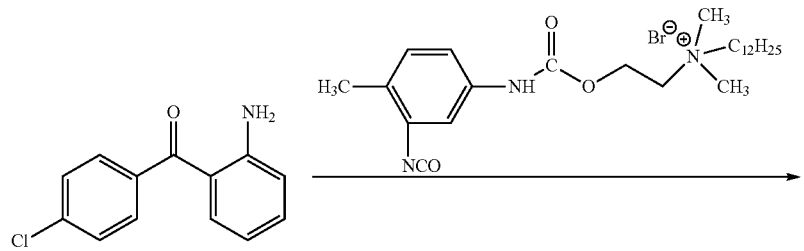

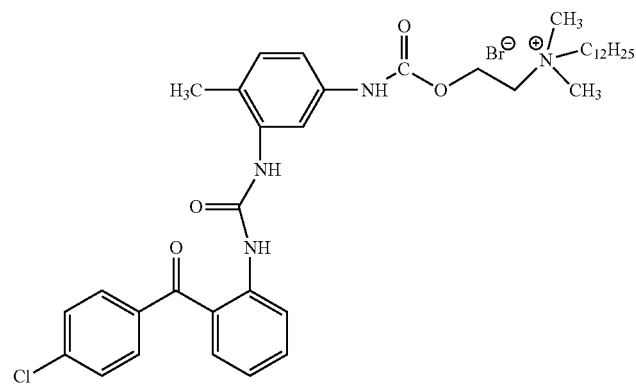

Example 19

35.7 g of the compound (3) and 12.0 g of 1-dimethylamine-2-propyne were added to 100 ml of water as a solvent, and a small amount of copper sulfate (catalyst) and sodium ascorbate (additive) were added. The reaction was carried out at 60° C. for 2 hours with stirring to obtain 38.6 g of an intermediate product (12). 31.6 g of the intermediate product (12) and 21.0 g of Br—C8H17 were placed in a 500 ml three-necked flask, and ethyl acetate (200 ml) was added. After refluxing for 24 hours, the reaction was extracted and purified by chloroform/methanol, and then evaporated to dryness to yield 46.5 g of reactive quaternary ammonium salt of antibacterial compound by a rotary evaporator. The reaction formula was as follows:

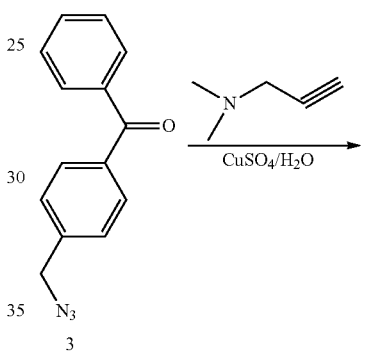

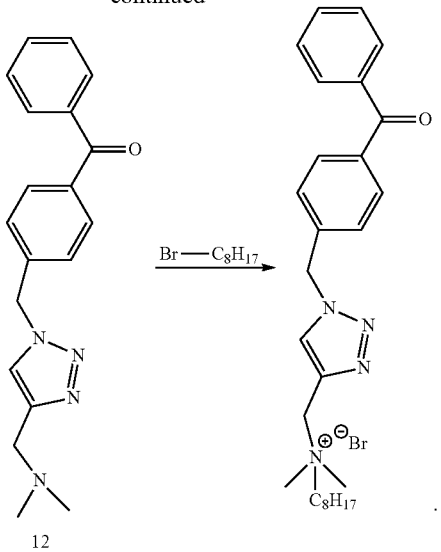

The quaternary ammonium salt type of antibacterial hydrophilic compound shown in Examples 11-19 may be modified and finished on a chemical fiber fabric such as polyester (PET). In the case of maintaining the mechanical properties and color of PET, the anti-static and easy-staining function may be imparted to the woven fabric in addition to the durable antibacterial, anti-mildew, and smashing functions.

Example 20

25.5 g of the compound (4) having an NCS group was dissolved in 100 ml of ethyl acetate (solvent). The mixture was added to a 500 ml round bottom flask with mechanical stirring. A small amount of phase transfer aid tetrabutylammonium bromide (TBAB) was added, and 0.29.7 g of poly hexamethylene biguanide hydrochloride (PHMG-NH2, dissolved in 100 ml of aqueous solution) was slowly added dropwise with a dropping funnel at 20° C. under stirring. And the reaction was continued for 2 h after the addition was completed to obtain an oily crude product. The mixture was purified by extraction with petroleum ether/N,N-acetamide for several times, and then dried by a rotary evaporator to obtain 48.6 g of an antibacterial compound of the biguanide type as shown in the following formula. The chemical reaction formula was as follows:

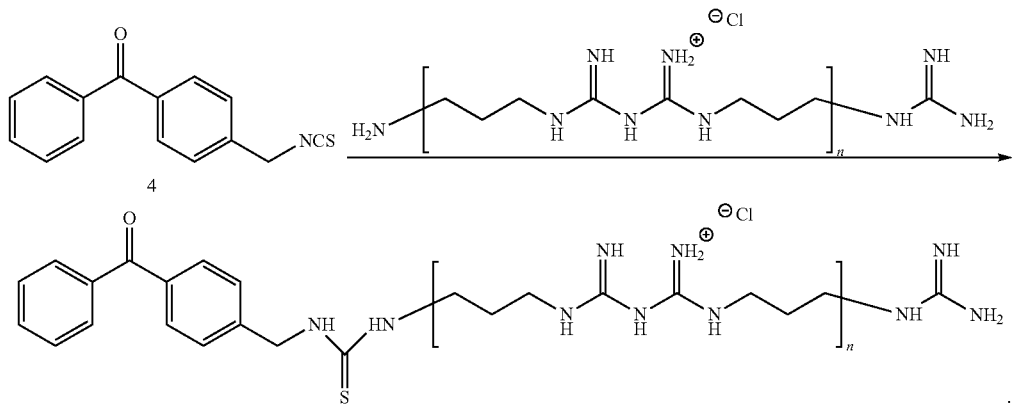

The biguanide antibacterial compound in the present example may be obtained by reacting —$NH_2$ group on the biguanidine compounds with a compound L' having an active group reactive with an amino group. These active groups may be —X, —NCO group, —COOH group,

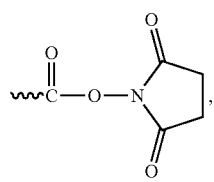

—COX group (Example 21), —$SO_2$X group, —CHO group (Example 22), or —CH(O)$CH_2$ group in addition to —NCS group, where X may be —Cl group, —Br group, or —I group.

Example 21

2-(Bromomethyl)-indole (28.5 g) was dissolved in 50 mL of DMSO, and NaCN (g, dissolved in 50 mL of DMSO) was added under rapid stirring. After reacting for 5 h at room temperature, 50 mL of purified water was added. Then, the mixture was extracted three times with ethyl acetate, and the organic phase was washed several times with brine, dried over anhydrous $Na_2SO_4$, and filtered and evaporated to obtain 2-(cyanomethyl)-indole. The obtained 2-(cyanomethyl)-indole was added to 50% $H_2SO_4$ (50 ml), refluxed for 1.5 h, cooled to room temperature, and the organic layer was washed several times with brine. 2-(cyanomethyl)-indole was then dried over anhydrous anhydrous $Na_2SO_4$ and concentrated in vacuo. The obtained 2-(carboxymethyl)-hydrazine was reacted with a substance such as thionyl chloride at room temperature for 1 hour, and then reacted in the presence of a solvent of benzene at 35° C. for 6 hours to obtain 2-(formyl chloride)-hydrazine.

The same amount of 2-(formyl chloride)-hydrazine and polyhexamethylene biguanide were reacted in a mixed solvent of DMSO/H2O for 0.5 h at room temperature in the presence of 10% NaOH. After extraction by DMSO/water extraction for 3 times, the bismuth-based antibacterial compound was obtained. The reaction formula was as follows:

Example 22

2-Methylthiazepine (24.0 g), benzoyl peroxide (1.2 g), and N-bromosuccinimide (NBS, 18.0 g) were dissolved in carbon tetrachloride ($CCl_4$, 200 ml) and heated to 85° C. After reacting for 24 hours, the mixture was cooled to room temperature, and the solid was filtered and washed 3 times with $CCl_4$ to obtain 30.2 g of white solid, that was, 2-(bromomethyl)-thiazolidine.

Using a molecular sieve containing palladium chloride (MCM-41-S—$PdCl_2$) as a catalyst, CO (1 atm) as an atmosphere, and DMF as a solvent (150 ml), the 2-(bromomethyl)-thiaindole was reacted with $HCO_2Na$ (10.2 g) at 100° C. for 6 h, washed several times with pure water, and dried under vacuum to obtain 28.5 g of 2-(formylmethyl)-thiazolidine.

The obtained 2-(formylmethyl)-thiaindole was reacted with an amount of the same material of polyhexamethylene biguanide in a DMF solvent for 30 minutes to obtain a novel biguanide antibacterial compound. The reaction formula was as follows:

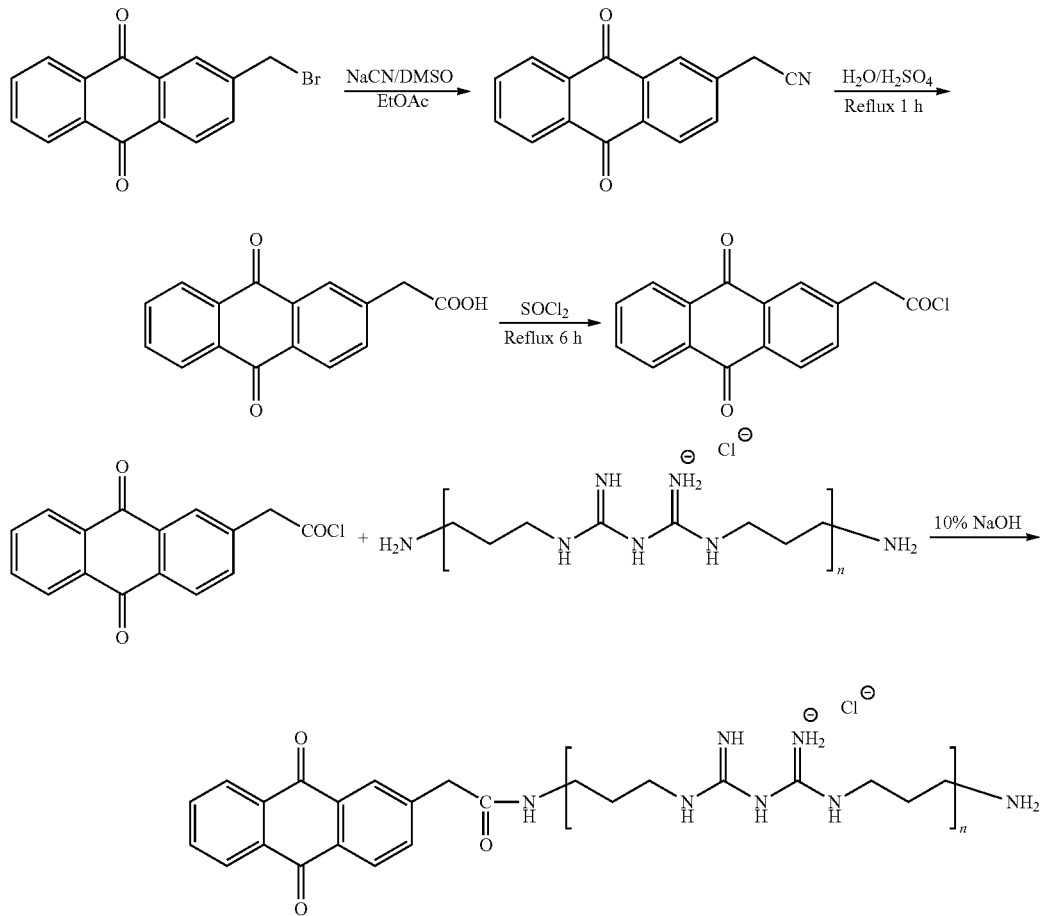

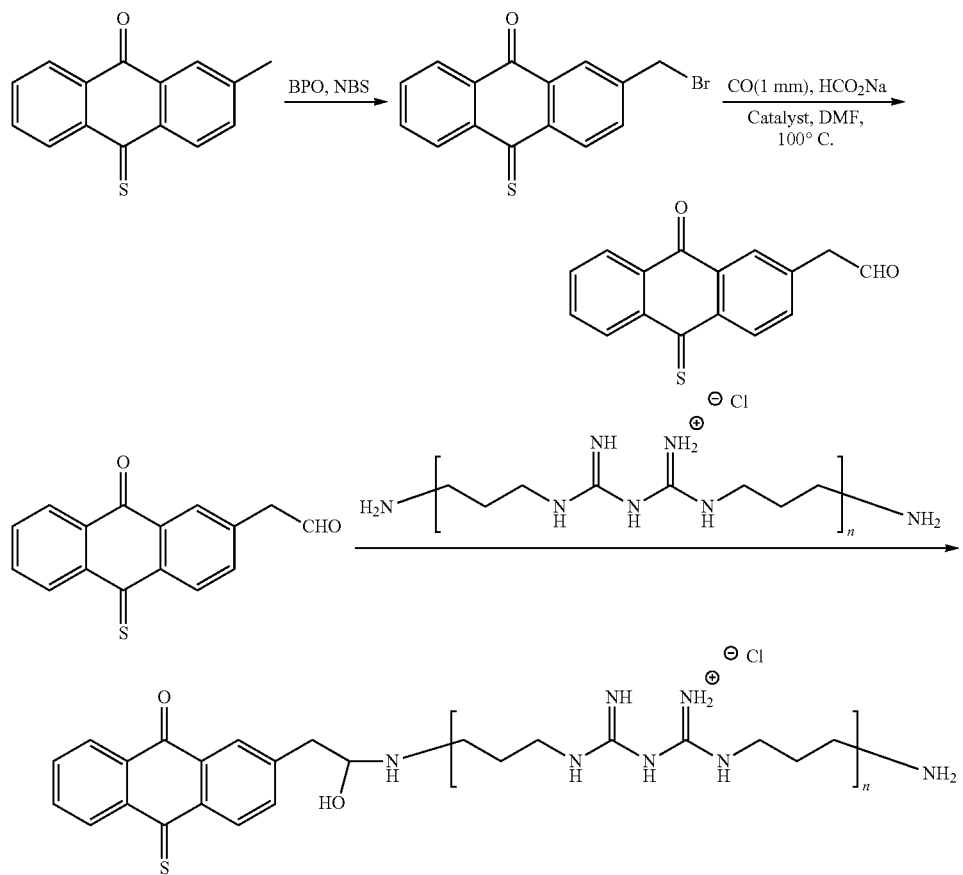

Similarly, polyhexamethylene biguanide was also reacted with 1-(2,3-epoxy)propoxythiazepine to obtain a biguanide antibacterial compound, as follows:

28.5 g of 1-(2,3-epoxy)propoxythiazide and 18.6 g of polyhexamethylene biguanide with terminal amino group were weighed and added into 200 mL of dimethyl sulfoxide. The ring-opening reaction was carried out at room temperature for 1 h. After filtration and washing several times with THF, 55.0 g of the reactive polyhexamethylene biguanide hydrochloride was obtained. The reaction formula was as follows:

The embodiments 20-22 may be all prepared by the biguanide type antibacterial compound. This kind of antibacterial compound may impart the durable antibacterial, anti-mildew, and drastic functions of the fabric while maintaining the mechanical properties and color of PET after modifying the chemical fiber fabric such as PET.

Example 23

25.5 g of the compound containing —NCS (4) may be dissolved in 150 ml of ethyl acetate solvent, and added to a 500 ml round bottom flask with mechanical stirring. A small amount of phase transfer aid tetrabutylammonium fluoride

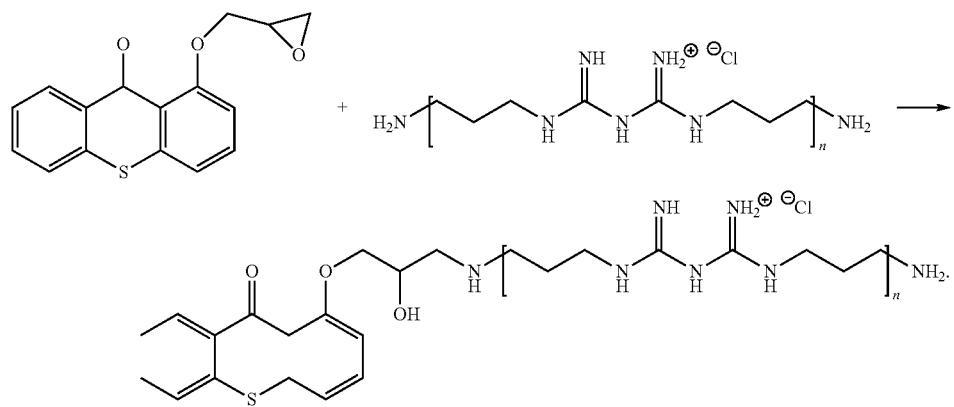

(TBAF) was added thereto, and 46.2 g of PEI (PEI dissolved in 150 ml of ethanol, and the number average molecular weight of PEI of 7000) was slowly added dropwise with a dropping funnel at 20° C. under stirring. After the completion of the dropwise addition, the reaction was continued for 2 hours to obtain an oily crude product which was purified by extraction and purification several times, and then dried by a rotary evaporator to obtain 58.9 g of an antibacterial compound as shown in the following formula. The chemical reaction formula was as follows:

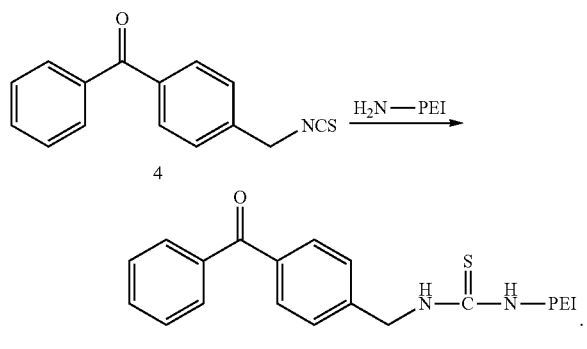

Example 24

25.5 g of the compound (4) containing —NCS may be dissolved in 150 ml of ethyl acetate solvent, and then added to a 500 ml round bottom flask with mechanical stirring. A small amount of phase transfer aid tetrabutylammonium bromide (TBAB) as added, and 6.5 g of chitosan (CS—NH$_2$, a number average molecular weight of 5,000, dissolved in 1% of 150 ml of aqueous acetic acid) was slowly added dropwise with a dropping funnel at 20° C. under stirring. After the completion of the dropwise addition, the reaction was continued for 2 hours to obtain a crude product which was extracted and purified by diethyl ether/acetic acid aqueous solution for several times, and then dried by a rotary evaporator to obtain 15.6 g of the antibacterial hydrophilic compound of the following formula. The chemical reaction formula was as follows:

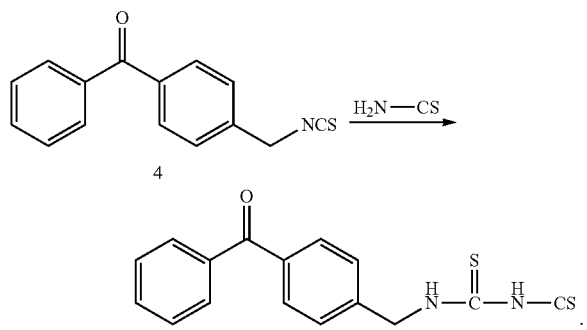

Example 25

3.2 g of chitosan in 10 g of methanesulfonic acid was weighed and stirred until completely dissolved. And then 0.25 g of 4-isocyanatobenzophenone dissolved in 20 ml of dimethyl sulfoxide was slowly added. 2 drops of dibutyltin dilaurate was added as a catalyst. The reaction was stirred at a constant temperature at 70° C. for 10 h to obtain a brown suspension. Then, 20 mL of 2 M aqueous NaOH solution was added for deamination protection, and dialysis was carried out in deionized water for 48 hours using a dialysis bag having a molecular weight cut off of 3000. After lyophilized for 48 hours, a brown powder was obtained, thereby obtaining an antibacterial compound as shown below. And its chemical reaction formula was as follows:

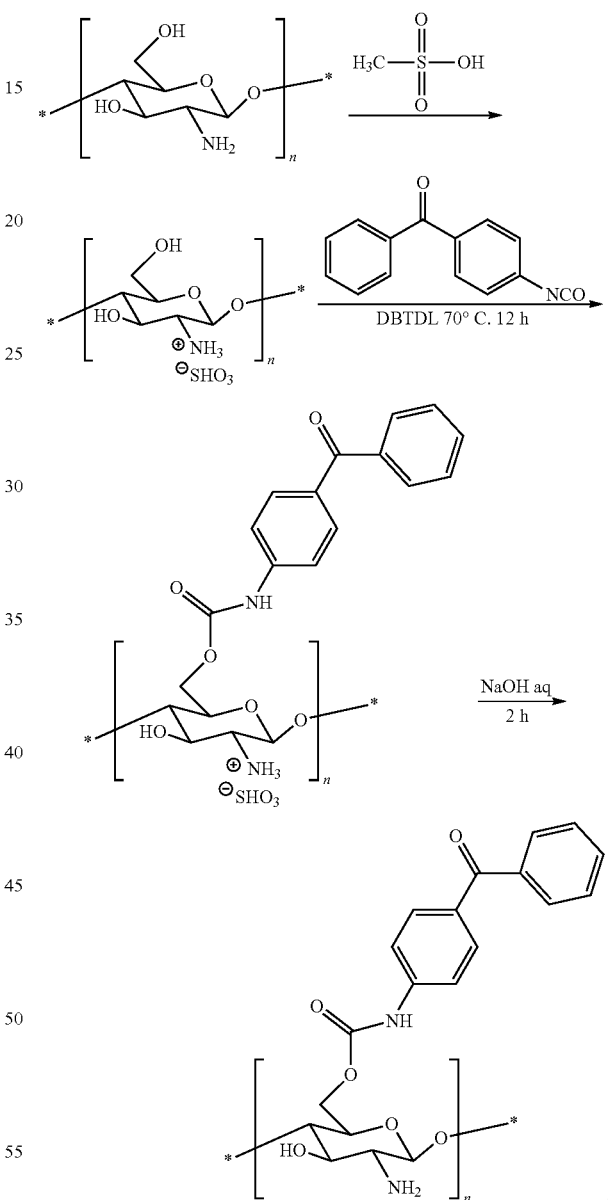

The antibacterial hydrophilic compounds prepared in the above Examples 23-25 may be all polyamino type. This type of antibacterial compound, after modifying the material containing C—H groups, may impart antistatic properties to the material surface in addition to the antibacterial, anti-mildew, repellent, and hydrophilicity of the material surface. If this type of compound is used in textile processing, it may contribute to the dyeing of anionic dyes.

Example 26

The reaction of formaldehyde with 5,5-dimethylhydantoin according to the method of the literature [JApplPolymSci, 2003, 89(9): 2418-2425] obtained 3-hydroxymethyl-2,2,5,5-tetramethylimidazolidine-4-one (MTMIO). Then, by oxidation treatment of hypochlorite, a chloromethyl group-containing chloramine compound (20) was obtained, that was, 1-chloro-3-hydroxymethyl-2,2,5,5-tetramethylimidazolidine-4-one. 20.7 g of the hydroxychloroamine-containing compound (20) and 22.5 g of 4-isocyanato-benzophenone were placed in a 500 ml three-necked flask, 200 ml of a butanone solvent was added, and a small amount of a stannous octoate catalyst was added. The reaction was continued at 50° C. for 2 hours, and then purified by ethanol/chloroform recrystallization several times to obtain 39.2 g of a halogen amine type of antibacterial compound. The reaction principle was as follows:

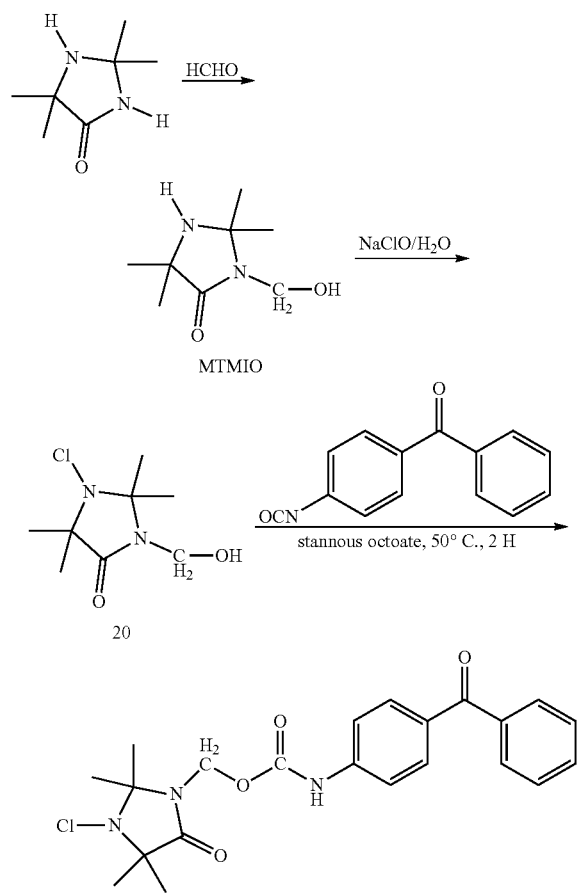

The reaction of some embodiments may refer to the preparation reaction formula (3) of the foregoing halogen amine type of antibacterial compound, and the reaction product thereof may correspond to the structural form of the aforementioned L-D-B$_3$.

Example 27

27.5 g (0.1 mol) of 4-(bromomethyl)benzophenone (2) and 12.8 g of 5,5-dimethylhydantoin (0.1 mol) were weighed and added to a 500 mL three-necked flask containing 200 mL of DMF. The reaction was carried out at 95° C. for 10 hours. The solvent was distilled off under reduced pressure, and then oxidized in a 1% aqueous sodium hypochlorite solution at room temperature for 10 minutes to obtain 29.6 g of the following dimethyl ketone-containing antibacterial compound, the reaction formula of which was shown below:

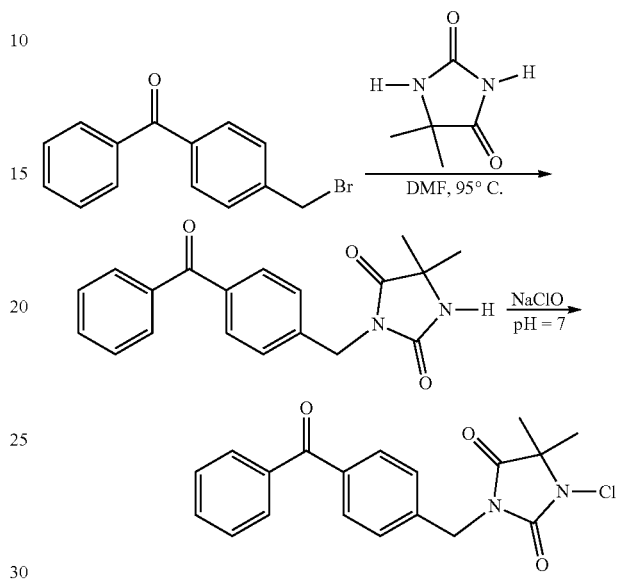

The reaction of some embodiments may correspond to the preparation reaction formula (2) of the former halogen amine type of antibacterial compound, and the reaction product thereof may correspond to the structural form of the aforementioned L-D-B$_2$.

Example 28

3-epoxypropyl-5,5-dimethylhydan was obtained by the reaction of 5,5-dimethylhydantoin with epichlorohydrin (Reference: Ind. Eng. Chem. Res. 2007, 46, 6425-6429). 3-Epoxypropyl-5,5-dimethylhydantoin (21.9 g) was weighed and placed in a 500 ml three-necked flask, and oxidatively activated in a 0.1% aqueous solution of sodium hypochlorite for 20 minutes. Then 4-aminomethylxyl ketone (21.1 g, dissolved in 200 ml of DMF solvent) was added. After reacting for 2 h at room temperature, 41.2 g of a halogen amine antibacterial compound was obtained. And the reaction formula was as follows:

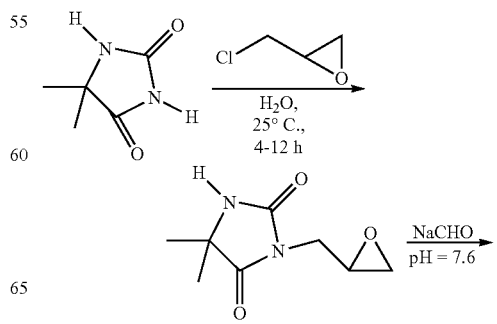

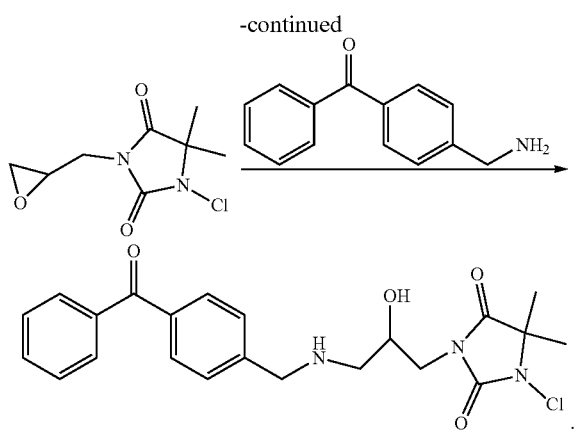

The reaction of some embodiments may refer to the preparation reaction formula (1) of the foregoing halogen amine type of antibacterial compound, and the reaction product thereof may correspond to the structural form of L-D-B$_2$.

Example 29

20.7 g of a hydroxychloroamine-containing compound (20) and 22.5 g of isophorone diisocyanate (IPDI) were placed in a 500 ml three-necked flask. 200 ml of a methyl ethyl ketone solvent was added, and a small amount of stannous octoate catalyst was added. The reaction was continued at 50° C. for 4 hours, then 4-aminomethylbenzophenone (19.75 g) was added. The reaction was continued for 2 h at room temperature, and repeatedly extracted and extracted several times with petroleum ether/dimethyl sulfoxide to obtain a halogen amine antibacterial compound 52.6 g. The reaction formula was as follows:

The reaction of some embodiments may refer to the preparation reaction formula (4) of the foregoing halogen amine type of antibacterial compound, and the reaction product thereof may correspond to the structural form of the aforementioned L-D-B$_3$, where D is

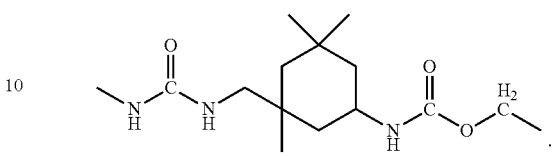

After modifying and finishing the chemical fiber fabric such as polyester, while maintaining its mechanical properties basically unchanged, the antibacterial compound shown in Examples 26-29 may impart durable antibacterial and antifungal functions to the fabric. In the process of killing harmful microorganisms, the antibacterial antibacterial compound may lose the antibacterial activity by converting the N—X bond in the molecule into the N—H bond. However, after oxidation by the oxidant, the N—H bond may be oxidized to N—X and its strong antibacterial activity may be restored.

Example 30

The quaternary ammonium salt type of antibacterial compound obtained in Example 12 was dissolved in water to prepare a 1% finishing liquid (i.e., an exemplary modification agent). After impregnating the polyester (PET) textile with the finishing liquid, irradiation in ultraviolet light (wavelength: 254 nm) for 1 minute, washing and drying the treated PET textile, a textile with durable antibacterial, anti-mildew, anti-static, and hydrophilic functions was obtained. The schematic diagram of the reaction principle was as follows:

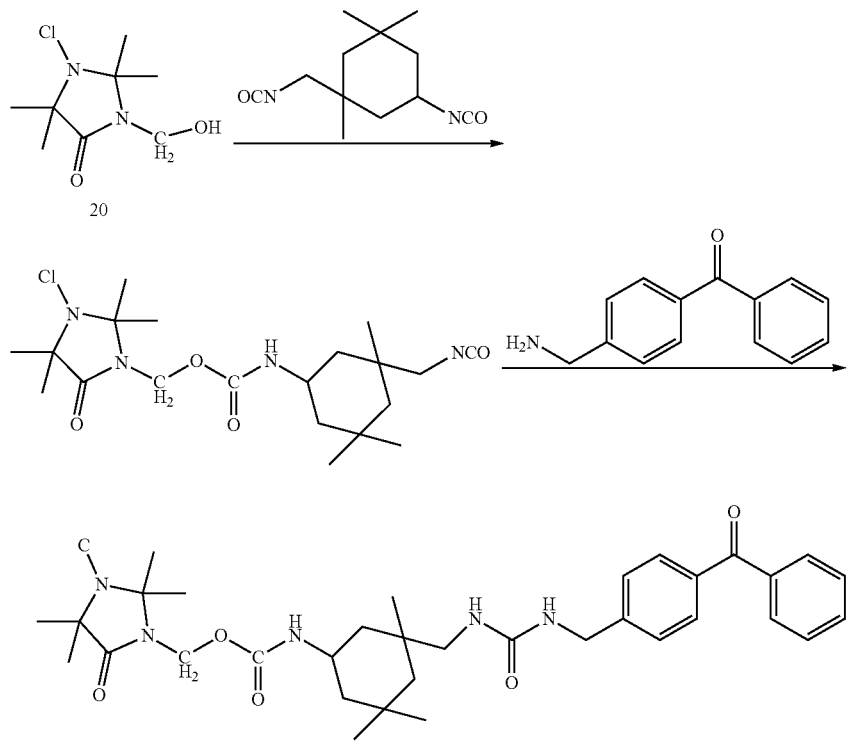

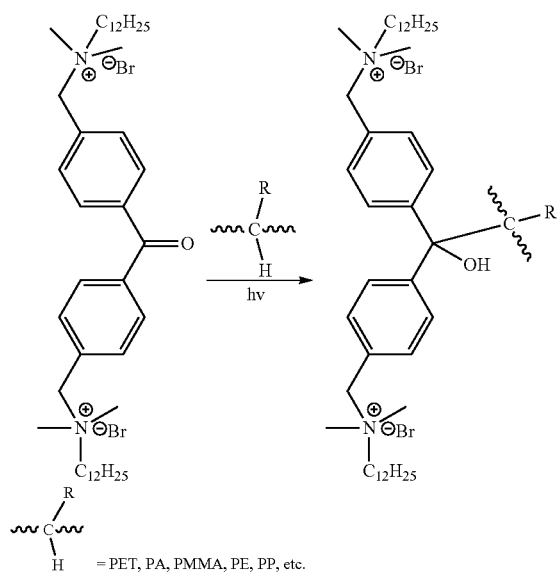

= PET, PA, PMMA, PE, PP, etc.

Similarly, the antibacterial hydrophilic compounds obtained in Examples 1-30 may be subjected to a function of a similar finishing process for synthesizing textiles, nonwoven fabrics, chemical fibers, films, etc., to obtain a durable antibacterial and antifungal product. It may be especially suitable for the following C—H group fabrics: chemical fiber fabrics such as modified polyester, nylon (PA), spandex (PU), vinylon (polyvinyl acetal), PE (polyethylene), PP (polypropylene, polypropylene), polymethyl methacrylate (PMMA), PP nonwoven fabric, etc. These fabrics may be modified by these antibacterial compounds to impart durable antibacterial, anti-mildew, repellent, and hydrophilic functions while maintaining their mechanical properties and color.

The antibacterial hydrophilic compounds obtained in Examples 1-29 may be formulated into a finishing liquid having a mass concentration of 0.1-10% using water as a solvent, and the PET cloth may be impregnated and modified by the finishing liquid. After irradiation for 1 minute at ultraviolet light (wavelength: 254 nm), the antibacterial activity against *Escherichia coli* and *Staphylococcus aureus* may be tested by plate counting method, and their hydrophilicity (water contact angle of untreated PET may be 92 degrees) may be tested. The test results are shown in Table 1.

TABLE 1

Analysis of durable antibacterial activity and hydrophilicity of the surface of PET cloth modified by antibacterial compounds

| Sample | Contact angel | Bacterial species | Antibacterial activity Washing one time | Washing 50 times |
|---|---|---|---|---|
| Example 1 | 0 | E. coli | 99.99% | 88.5% |
| | | S. aureas | 99.99% | 92.9% |
| Example 2 | 0 | E. coli | 99.99% | 86.2% |
| | | S. aureas | 99.99% | 89.9% |
| Example 3 | 0 | E. coli | 99.99% | 87.8% |
| | | S. aureas | 99.99% | 90.2% |
| Example 4 | 0 | E. coli | 99.99% | 86.9% |
| | | S. aureas | 99.99% | 80.9% |
| Example 5 | 0 | E. coli | 99.99% | 86.2% |
| | | S. aureas | 99.99% | 90.6% |
| Example 6 | 0 | E. coli | 99.99% | 86.6% |
| | | S. aureas | 99.99% | 89.7% |
| Example 7 | 0 | E. coli | 99.99% | 87.1% |
| | | S. aureas | 99.99% | 91.9% |
| Example 8 | 0 | E. coli | 99.99% | 85.7% |
| | | S. aureas | 99.99% | 89.5% |
| Example 9 | 0 | E. coli | 99.99% | 85.8% |
| | | S. aureas | 99.99% | 88.6% |
| Example 10 | 0 | E. coli | 99.99% | 86.1% |
| | | S. aureas | 99.99% | 89.9% |
| Example 11 | 0 | E. coli | 99.99% | 92.8% |
| | | S. aureas | 99.99% | 99.9% |
| Example 12 | 0 | E. coli | 99.99% | 96.9% |
| | | S. aureas | 99.99% | 99.9% |
| Example 13 | 0 | E. coli | 99.99% | 91.7% |
| | | S. aureas | 99.99% | 96.9% |
| Example 14 | 0 | E. coli | 99.99% | 91.7% |
| | | S. aureas | 99.99% | 96.9% |
| Example 15 | 0 | E. coli | 99.99% | 96.8% |
| | | S. aureas | 99.99% | 99.9% |
| Example 16 | 0 | E. coli | 99.99% | 91.7% |
| | | S. aureas | 99.99% | 98.5% |
| Example 17 | 0 | E. coli | 99.99% | 90.8% |
| | | S. aureas | 99.99% | 97.6% |
| Example 18 | 0 | E. coli | 99.99% | 95.8% |
| | | S. aureas | 99.99% | 99.9% |
| Example 19 | 0 | E. coli | 99.99% | 92.8% |
| | | S. aureas | 99.99% | 99.6% |
| Example 20 | 0 | E. coli | 99.99% | 94.9% |
| | | S. aureas | 99.99% | 99.8% |
| Example 21 | 0 | E. coli | 99.99% | 96.9% |
| | | S. aureas | 99.99% | 99.5% |
| Example 22 | 0 | E. coli | 99.99% | 95.9% |
| | | S. aureas | 99.99% | 99.6% |
| Example 23 | 0 | E. coli | 99.99% | 90.8% |
| | | S. aureas | 99.99% | 97.9% |
| Example 24 | 0 | E. coli | 99.99% | 91.8% |
| | | S. aureas | 99.99% | 99.9% |
| Example 25 | 0 | E. coli | 99.99% | 93.8% |
| | | S. aureas | 99.99% | 96.9% |
| Example 26 | 45 | E. coli | 99.99% | 97.9% |
| | | S. aureas | 99.99% | 99.9% |
| Example 27 | 50 | E. coli | 99.99% | 94.9% |
| | | S. aureas | 99.99% | 99.8% |
| Example 28 | 40 | E. coli | 99.99% | 95.1% |
| | | S. aureas | 99.99% | 99.9% |
| Example 29 | 50 | E. coli | 99.99% | 95.1% |
| | | S. aureas | 99.99% | 99.8% |
| Example 30 | 30 | E. coli | 99.99% | 97.1% |
| | | S. aureas | 99.99% | 99.9% |

FIG. 1 is a group of photographs illustrating an antibacterial and antifungal effect of PET cloth treated or untreated by an antibacterial hydrophilic compound according to Example 11 of the present disclosure. The first row (A1-A6) of photographs correspond to untreated PET cloth, and the second row (B1-B6) of photographs correspond to modified PET cloth. The validated microorganisms used from left to right (1-6) are *E. coli, S. aureas, A. niger, A. baumannii, S. epidermidis,* and *P. aeruginosa.* FIG. 2 is a group of photographs illustrating a mite-killing effect of PET cloth treated or untreated by an antibacterial hydrophilic compound according to Example 11 of the present disclosure, where section (a) is a photograph of untreated PET cloth, and section (b) is a photograph of treated PET cloth.

Figure 2:
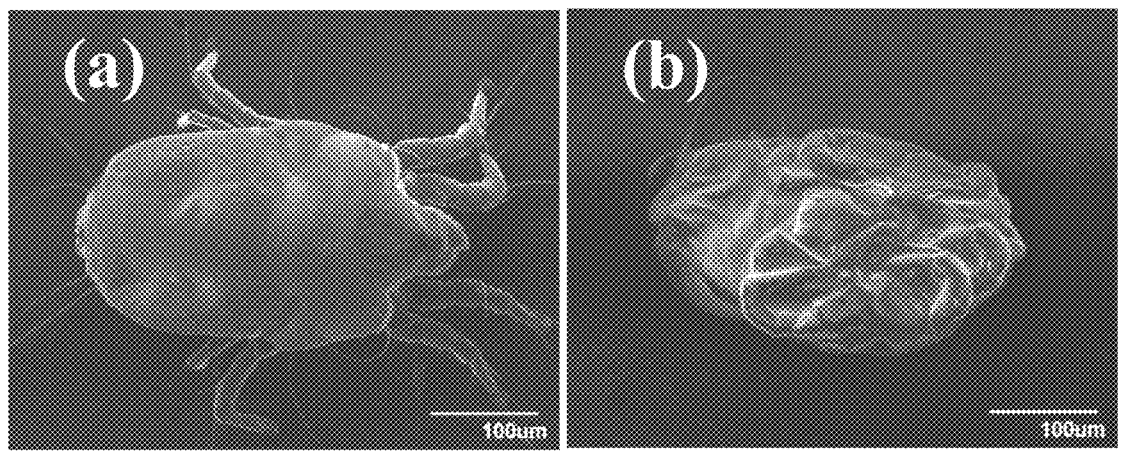
FIG. 2 is a group of photographs illustrating a mite-killing effect of PET cloth treated or untreated by an antibacterial hydrophilic compound according to Example 11 of the present disclosure, where section (a) is a photograph of untreated PET cloth, and section (b) is a photograph of treated PET cloth.

It may be apparent from FIGS. 1-2 that the PET cloth treated with the antibacterial hydrophilic compound provided by the present disclosure is effective in killing common bacteria, fungi, and mites.

Figure 3:
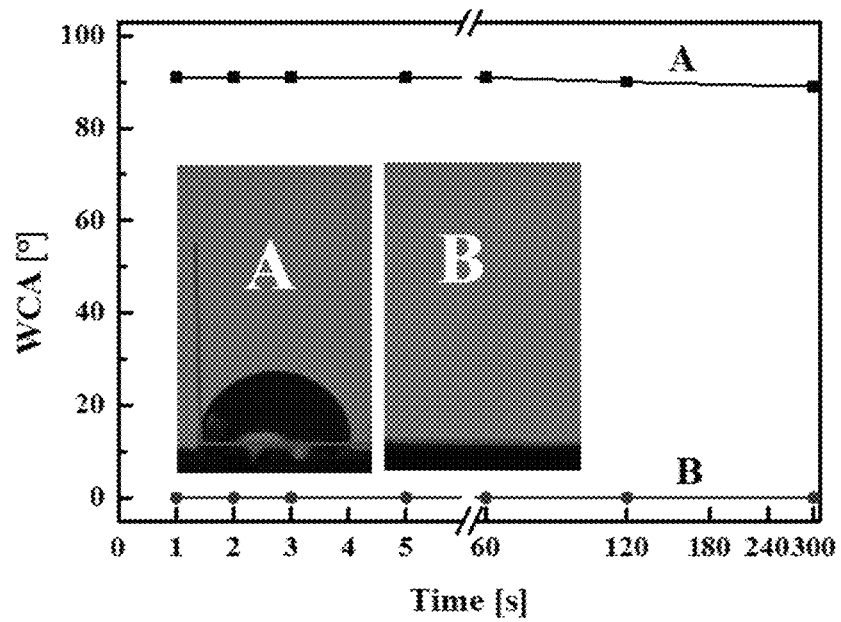
FIG. 3 illustrates a change in a contact angle of PET cloth treated or untreated by an antibacterial hydrophilic compound according to Example 13 of the present disclosure, where section (A) is a photograph of untreated PET cloth, and section (B) is a photograph of treated PET cloth.

FIG. 3 illustrates a change in a contact angle of PET cloth treated or untreated by an antibacterial hydrophilic compound according to Example 13 of the present disclosure, where section (A) is a photograph of untreated PET cloth, and section (B) is a photograph of treated PET clot. As seen from FIG. 3, the water contact angle of the PET cloth without being treated with the antibacterial hydrophilic compound was 92 degrees, and the water contact angle of the treated PET cloth was 0°, which indicates that the hydrophilicity of the PET cloth treated by the antibacterial hydrophilic compound of the present disclosure is greatly improved.

Figure 4:
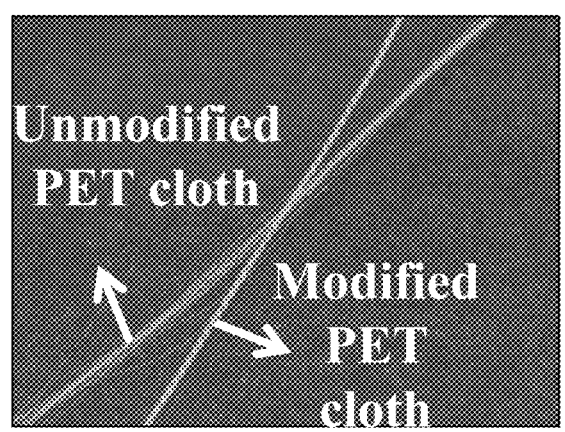
FIG. 4 illustrates a fiber morphology of PET cloth treated or untreated by an antibacterial hydrophilic compound according to Example 13 of the present disclosure.

FIG. 4 illustrates a fiber morphology of PET cloth treated or untreated by an antibacterial hydrophilic compound according to Example 13 of the present disclosure. It may be seen from FIG. 4 that the PET cloth modified by the antibacterial hydrophilic compound of Example 13 had stronger interaction force between fibers, and the fibers are more closely entangled with each other.

Figure 5:
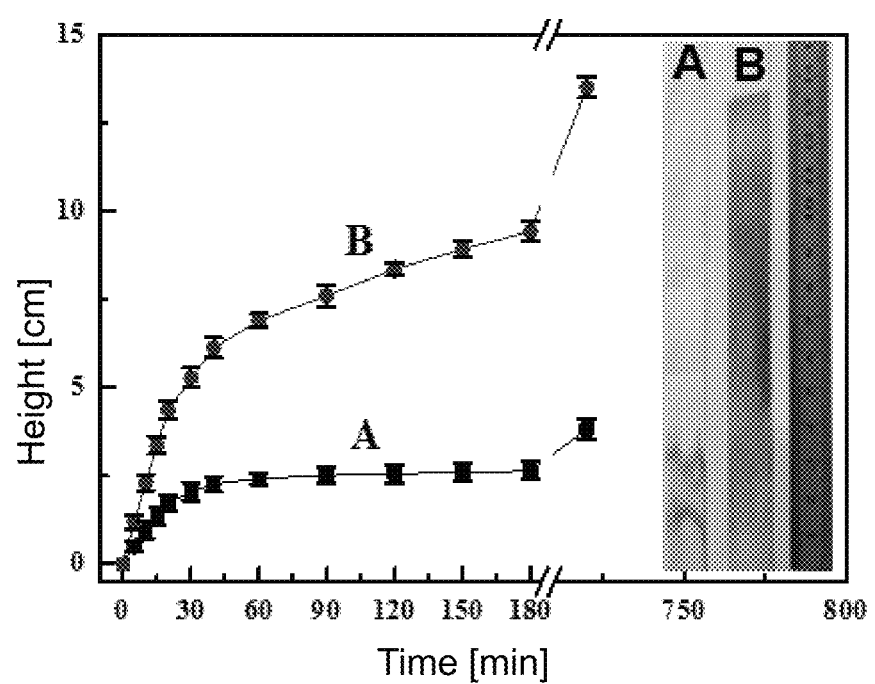
FIG. 5 is a diagram illustrating hydrophilicity of PET cloth treated with an antibacterial hydrophilic compound according to Example 1 of the present disclosure.

FIG. 5 is a diagram illustrating hydrophilicity of PET cloth treated with an antibacterial hydrophilic compound according to Example 1 of the present disclosure. As seen from FIG. 5, the PET cloth (B) modified by the antibacterial hydrophilic compound of Example 1 had a core height significantly greater than that of the unmodified PET (A), which shows that after the modification of the antibacterial hydrophilic compound of Example 1, the hydrophilicity of the PET cloth is greatly improved.

Figure 6:
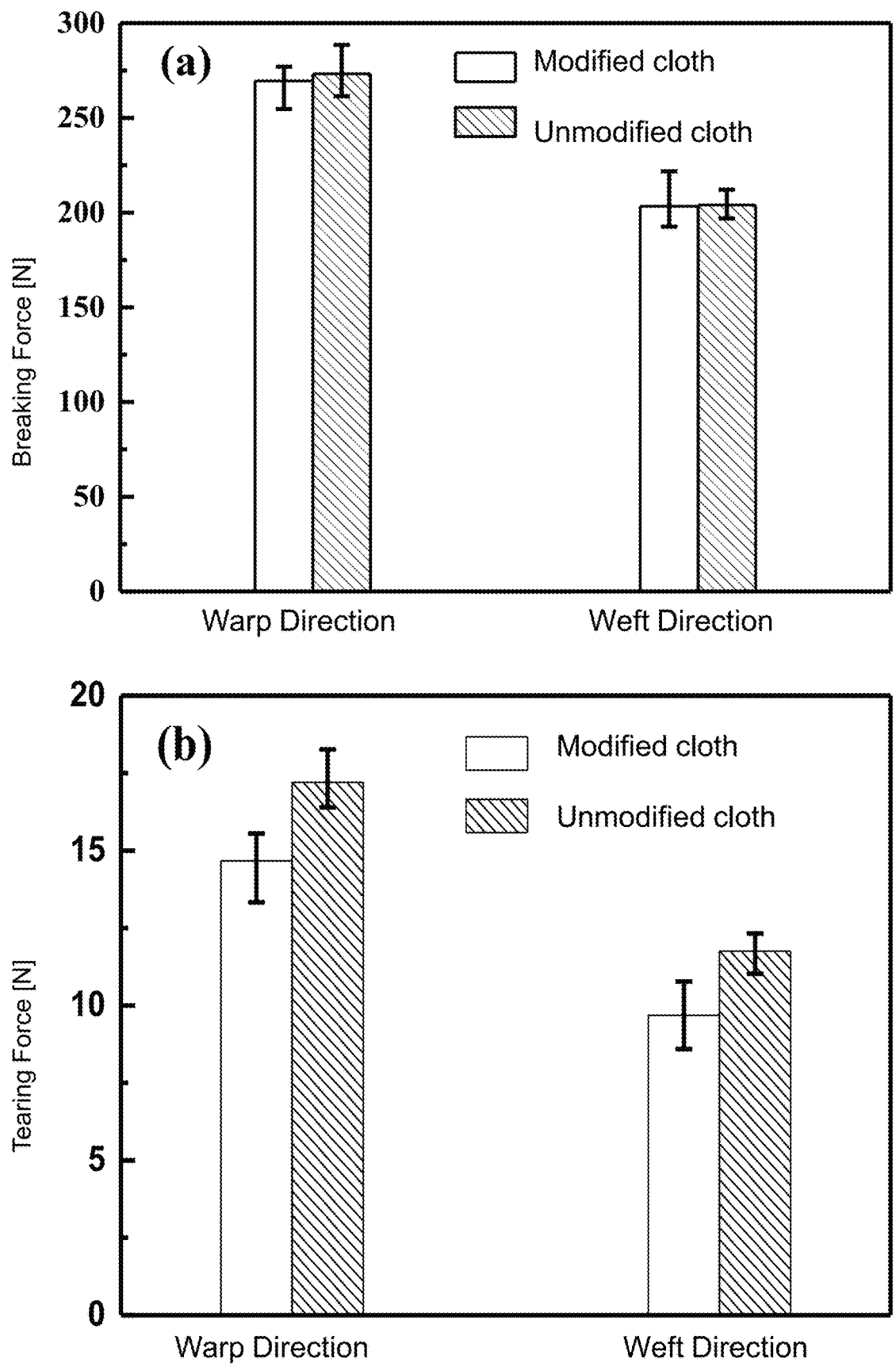
FIG. 6 illustrates mechanical properties of unmodified PET cloth and PET cloth modified by an antibacterial hydrophilic compound prepared according to Example 9 of the present disclosure, where section (a) illustrates the breaking force in warp and weft directions, and section (b) illustrates the tearing strength in the warp and weft directions.

FIG. 6 illustrates mechanical properties of unmodified PET cloth and PET cloth modified by an antibacterial hydrophilic compound prepared according to Example 9 of the present disclosure, where section (a) illustrates the breaking force in warp and weft directions, and section (b) illustrates the tearing strength in the warp and weft directions. The results of FIG. 6 show that the antibacterial hydrophilic compound substantially does not reduce the breaking force of the fabrics after modification of the PET fabric containing the C—H group. Moreover, the tearing force of the modified PET cloth in the warp direction (17% increase) and the weft direction (21% increase) may be greatly improved. Similarly, the antibacterial hydrophilic compounds provided by other embodiments of the present disclosure may also have similar functions, and the effects are not shown here.

The antibacterial hydrophilic compounds are provided in the embodiments in the present disclosure, which are firmly bonded to the material surface by a photo-induced rection of hydrogen abstraction groups (carbonyl group linked between two benzene rings) of the group L with the material surface having the C—H groups. Imparting durable antibacterial activity and hydrophilicity to the material can modify the material.

When the material is a synthetic fiber (such as polyester PET, nylon, spandex, polypropylene, vinylon, etc.), since the antibacterial hydrophilic compound is covalently bonded to the fabric surface, it is less likely to be washed off during the washing process of the fabric, giving the fabric durable and effective antibacterial, anti-mould properties and hydrophilicity. The wearing comfort of the fabric may be improved, and the breaking force and elongation at break of the fabric may be uneffected, thus the mechanical properties of materials that have good mechanical properties may not be negatively affected (and the mechanical properties of materials may even be improved). Further, the antibacterial hydrophilic compound may be applied to the field of textiles, but may be applied to fields such as paint, medicine, food packaging, etc., but is not limited thereto. For example, it is possible to achieve a combination of chemical bonds by photoactive hydrogen abstraction group and most materials such as plastics and rubber having a C—H group to obtain a stable antibacterial plastic, antibacterial rubber, and antibacterial coating. Alternatively, the antibacterial hydrophilic compound may also be chemically bonded with medical infusion tubes and medical packaging material surfaces to prepare antibacterial medical products, or chemically combined with food packaging or food preservation material surface to prepare antibacterial packaging materials.

The above embodiments may be merely illustrative of the present disclosure, and the descriptions thereof may be more specific and detailed, but not limited to the scope of the present disclosure. It should be noted that there are a number of variations and modifications that may be made to the present disclosure without departing from the principles of the present disclosure. Therefore, the scope of protection of the present disclosure shall be subject to the appended claims.

We claim:

1. An antibacterial hydrophilic compound, wherein a general structural formula of the antibacterial hydrophilic compound is represented by L-D-Q, wherein
at least one end of the group L is connected to the group Q through the linking group D;
an end of the group Q with "～～～" is connected to the linking group D;
the group L has a structure represented by the following formulas ($L_1$), ($L_2$), ($L_3$), ($L_4$), or ($L_5$);
the group D is a single-bond, or a divalent $C_{1-18}$ hydrocarbyl group that is unsubstituted or substituted, wherein the divalent $C_{1-18}$ hydrocarbyl group includes or does not include a linking group including heteroatom(s), the heteroatom(s) being at least one of O, S, N, Si, Se, or P atoms;
the group Q is selected from a biguanide compound residue represented by a formula ($C_1$), a group represented by the following formula ($D_2$), and halamine group represented by the following formulas ($B_1$), ($B_2$), ($B_3$), or ($B_4$),

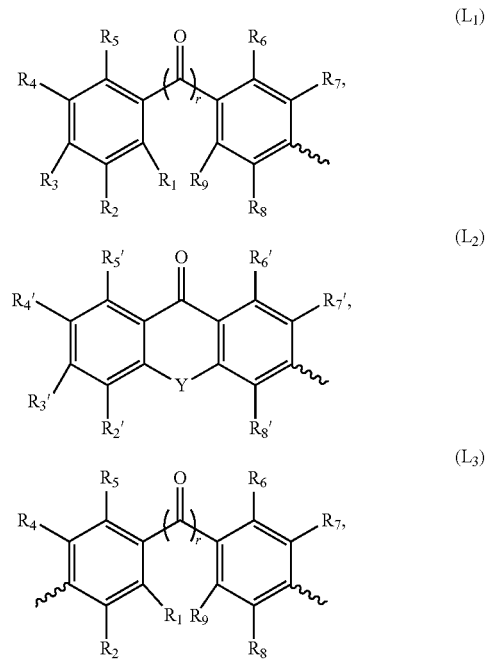

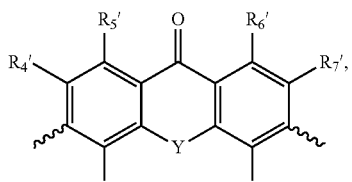
(L4)

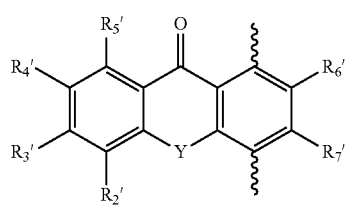
(L5)

wherein
r is 1 or 2;
Y is one of a single bond, oxygen atom, sulfur atom, silicon atom, selenium atom, —C(O)— group, —SO$_2$— group, —NH— group, and a C$_{1-3}$ alkylene group; R$_1$-R$_9$ and R$_2'$-R$_8'$ are independently selected from hydrogen atom, halogen atom, monovalent polar group, and monovalent C$_{1-18}$ hydrocarbyl groups that are substituted or unsubstituted;

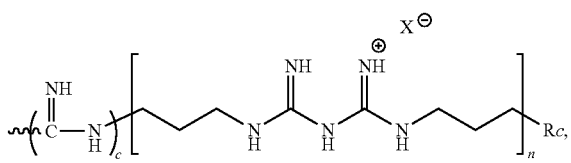
(C1)

wherein
c is an integer from 0 to 2, n is a positive integer from 1 to 100, R$_c$ is selected from a monovalent C$_{1-18}$ hydrocarbyl group that is unsubstituted or substituted, wherein the monovalent C$_{1-18}$ hydrocarbyl group includes or does not include a linking group including heteroatom, the heteroatom being N atom, and X is selected from halogen atom;

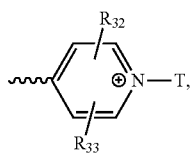
(D2)

wherein
T is R$_{13}$ or —R$_{23}$-A$^\ominus$, R$_{13}$ is independently selected from monovalent C$_{1-18}$ hydrocarbyl groups that are unsubstituted or substituted, and R$_{23}$ is selected from divalent C$_{1-18}$ hydrocarbyl groups that are unsubstituted or substituted; R$_{32}$-R$_{33}$ are independently selected from hydrogen atom, halogen atom, monovalent polar group, and monovalent C$_{1-18}$ hydrocarbyl groups that are substituted or unsubstituted; A is selected from —COO, —SO$_3$ and —OPO$_2$OR$_e$, and R$_e$ is a monovalent C$_{1-6}$ alkyl, cycloalkyl, or aryl group, wherein R$_e$ is unsubstituted or substituted;

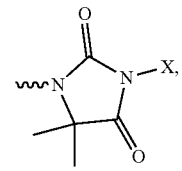
(B1)

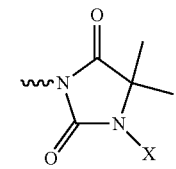
(B2)

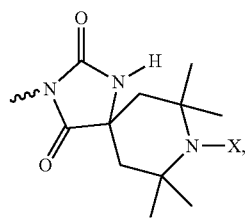
(B3)

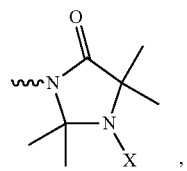
(B4)

wherein
X is selected from halogen atom.

2. The antibacterial hydrophilic compound of claim 1, wherein Y is oxygen atom, sulfur atom, or —C(O)—.

3. The antibacterial hydrophilic compound of claim 1, wherein when the group Q is the biguanide compound residue represented by the formula (C$_1$), the linking group D is a divalent C$_{1-18}$ hydrocarbyl group that is unsubstituted or substituted and includes a linking group including heteroatom(s).

4. The antibacterial hydrophilic compound of claim 3, wherein when the group Q is the biguanide compound residue represented by the formula (C$_1$), the linking group D has the following group Z, wherein the group Z is —NH—* group, —NH—C(S)—NH—* group, —NH—C(O)—NH—* group, —NH—C(O)—* group, —CO—NH—* group, —SO$_2$—NH—* group, —CH(OH)—NH—* group, or —CH(OH)CH$_2$—NH—* group, and an end of the group Z with "*" is connected to the side of group Q.

5. The antibacterial hydrophilic compound of claim 1, wherein in the formula (D$_2$), R$_{23}$ is selected from an alkylene group having 1-18 carbon atoms; R$_{32}$-R$_{33}$ are independently selected from hydrogen atom, halogen atom, —CN, —SCN, —NO$_2$, —NO, and monovalent unsubstituted or substituted C$_{1-7}$ alkyl, cycloalkyl, or aryl.

6. The antibacterial hydrophilic compound of claim 1, wherein when the group Q is a structure represented by the formula (D$_2$), the linking group D has the following group Z, wherein the group Z is —NH—C(O)—NH—*, —NH—C(S)—NH—*, —NH—C(S)—O—*, or —NHCOO*-, and an end of the group Z with "*" is connected to a side of group Q.

7. The antibacterial hydrophilic compound of claim 6, wherein when the group Q is a structure represented by the formula ($D_2$), and when T is —$R_{23}$-$A^{\ominus}$, the antibacterial hydrophilic compound is prepared by the following method:

(1) reacting the compound $L_1'$ or $L_2'$ represented by the following structural formulas with pyridine having the general formula (I) to obtain a mixture,

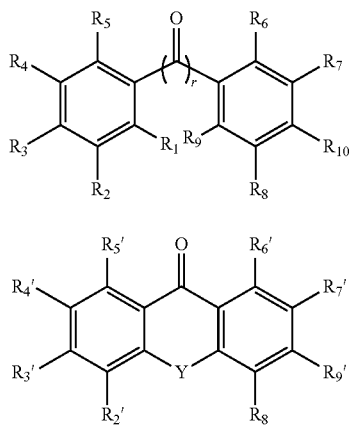

wherein r is 1 or 2; Y is one of a single bond, oxygen atom, sulfur atom, silicon atom, selenium atom, —C(O)—, —$SO_2$—, —NH—, and a $C_{1-3}$ alkylene group; $R_1$-$R_{10}$ and $R_2'$-$R_9'$ are independently selected from hydrogen atom, halogen atom, monovalent polar groups, and monovalent $C_{1-18}$ hydrocarbyl group that is unsubstituted or substituted, and at least one of $R_1$-$R_{10}$ or $R_2'$-$R_9'$ has —NCO or —NCS;

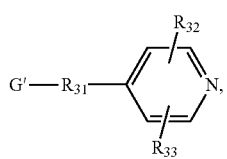

wherein

G' is selected from —OH, $NH_2$, or —SH, and $R_{31}$ is selected from divalent $C_{1-18}$ hydrocarbyl groups that are unsubstituted or substituted, and $R_{32}$-$R_{33}$ are independently selected from hydrogen atom, halogen atom, monovalent polar groups, and monovalent $C_{1-18}$ hydrocarbyl groups that are unsubstituted or substituted;

(2) reacting the mixture with the compound E to obtain a zwitterionic type of the antibacterial hydrophilic compound:

the compound E is selected from sultone, carboxylic acid lactone, $X(CH_2)_w COO^- M_r^+$, $X(CH_2)_w SO_3^- M_r^+$, and cyclic phosphate, wherein X is selected from Br, Cl, and I, w is an integer no less than 1, $M_r^+$ is selected from $Li^+$, $Na^+$, $K^+$, $NH_4^+$, $Ag^+$, $\frac{1}{2}Mg^{2+}$, and $\frac{1}{2}Ca^{2+}$, cyclic phosphate has a structure represented by the following formula:

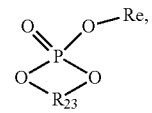

wherein Re is unsubstituted or substituted monovalent $C_{1-6}$ alkyl, cycloalkyl, or aryl, and $R_{23}$ is selected from divalent $C_{1-18}$ hydrocarbyl groups that are unsubstituted or substituted.

8. The antibacterial hydrophilic compound of claim 7, wherein the structural formula of carboxylic acid lactone is

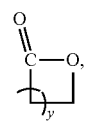

and y is an integer from 1 to 6; the structural formula of sultone is

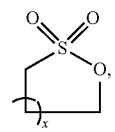

and x is an integer from 1 to 6.

9. The antibacterial hydrophilic compound of claim 1, wherein when the group Q is a halamine group represented by the formula ($B_1$), ($B_2$), ($B_3$) or ($B_4$), the linking group D is an alkylene group having 1 to 10 carbon atoms.

10. The antibacterial hydrophilic compound of claim 1, wherein when the group Q is a halamine group represented by the formula ($B_1$), ($B_2$), ($B_3$) or ($B_4$), the linking group D has the following group Z, wherein the group Z is —NH—C(O)—O—$CH_2$—*, —NH—$CH_2$—CH(OH)—$(CH_2)_q$—*, —S—$CH_2$—CH(OH)—$(CH_2)_q$—*, or —O—$CH_2$—CH(OH)—$(CH_2)_q$—*, wherein q is an integer from 1 to 6, and an end of the group Z with "*" is connected to one side of the group Q.

11. The antibacterial hydrophilic compound of claim 1, wherein when the group Q is a halamine group represented by the formula ($B_1$), ($B_2$), ($B_3$) or ($B_4$), the linking group D has the following group Z, wherein the group Z is —NH—C(S)—O—$CH_2$—*, —C(O)—O—$CH_2$—*, —$SO_2$—O—$CH_2$—*, —O—$CH_2$—*, or —CH(OH)$CH_2$—O—$CH_2$—*, and an end with "*" is on the side of the halamine group.

12. A processing method for a surface of a material, comprising the following operations:
providing a modification agent including an antibacterial hydrophilic compound;
spraying or brushing the modification agent on a surface of a material containing C—H groups and treating the surface with ultraviolet light to cause the antibacterial hydrophilic compound to covalently bind the surface to obtain a processed material, wherein
a general structural formula of the antibacterial hydrophilic compound is represented by L-D-Q, wherein
at least one end of the group L is connected to the group Q through the linking group D;
an end of the group Q with "〰" is connected to the linking group D;

the group L has a structure represented by the following formulas (L₁), (L₂), (L₃), (L₄), or (L₅);

the group D is a single-bond, or a divalent $C_{1-18}$ hydrocarbyl group that is unsubstituted or substituted, wherein the divalent $C_{1-18}$ hydrocarbyl group includes or does not include a linking group including heteroatom(s), the heteroatom(s) being at least one of O, S, N, Si, Se, or P atoms;

the group Q is selected from a biguanide compound residue represented by a formula (C₁), a group represented by the following formula (D₂), and halamine group represented by the following formulas (B₁), (B₂), (B₃), or (B₄),

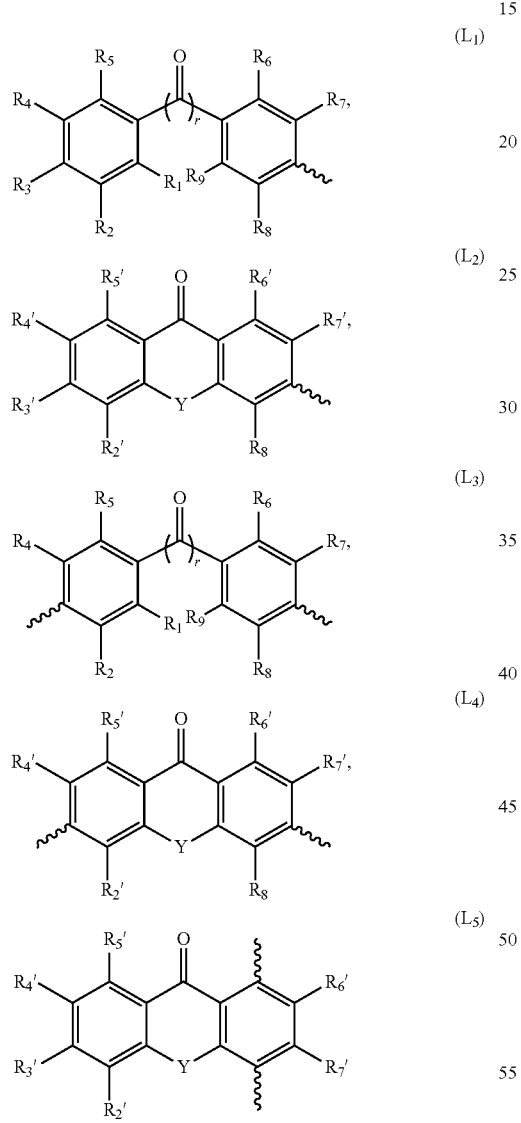

wherein
r is 1 or 2; Y is one of a single bond, oxygen atom, sulfur atom, silicon atom, selenium atom, —C(O)— group, —SO₂— group, —NH— group, and $C_{1-3}$ alkylene groups; $R_1$-$R_9$ and $R_2'$-$R_8'$ are independently selected from hydrogen atom, halogen atom, monovalent polar group, and monovalent $C_{1-18}$ hydrocarbyl groups that are substituted or unsubstituted;

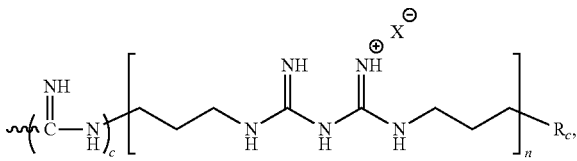

wherein
c is an integer from 0 to 2, n is a positive integer from 1 to 100, $R_c$ is selected from a monovalent $C_{1-18}$ hydrocarbyl group that is unsubstituted or substituted, wherein the monovalent $C_{1-18}$ hydrocarbyl group includes or does not include a linking group including heteroatom, the heteroatom being N atom, and X is selected from halogen atom;

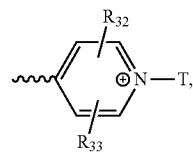

wherein
T is $R_{13}$ or —$R_{23}$-$A^⊖$, $R_{13}$ is independently selected from monovalent $C_{1-18}$ hydrocarbyl groups that are unsubstituted or substituted, and $R_{23}$ is selected from divalent $C_{1-18}$ hydrocarbyl groups that are unsubstituted or substituted; $R_{32}$-$R_{33}$ are independently selected from hydrogen atom, halogen atom, monovalent polar group, and monovalent $C_{1-18}$ hydrocarbyl groups that are substituted or unsubstituted; A is selected from —COO, —SO₃ and —OPO₂OR$_e$, and $R_e$ is a monovalent $C_{1-6}$ alkyl, cycloalkyl, or aryl group, wherein $R_e$ is unsubstituted or substituted;

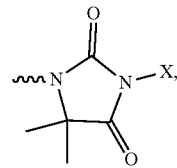

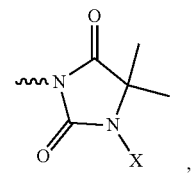

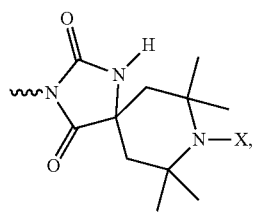

-continued

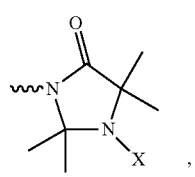

(B₄)

wherein X is selected from halogen atom.

13. The processing method of claim 12, wherein the material containing C—H groups includes one or more of synthetic fibers, rubbers, plastics, polymer coatings.

14. A modified material, wherein the modified material includes a surface covalently bonded with an antibacterial hydrophilic compound, the modified material having an antibacterial function, wherein
- a general structural formula of the antibacterial hydrophilic compound is represented by L-D-Q, wherein
  - at least one end of the group L is connected to the group Q through the linking group D;
  - an end of the group Q with "〰" is connected to the linking group D;
  - the group L has a structure represented by the following formulas ($L_1$), ($L_2$), ($L_3$), ($L_4$), or ($L_5$);
  - the group D is a single-bond, or a divalent $C_{1-18}$ hydrocarbyl group that is unsubstituted or substituted, wherein the divalent $C_{1-18}$ hydrocarbyl group includes or does not include a linking group including heteroatom(s), the heteroatom(s) being at least one of O, S, N, Si, Se, or P atoms;
  - the group Q is selected from a biguanide compound residue represented by a formula ($C_1$), a group represented by the following formula ($D_2$), and halamine group represented by the following formulas ($B_1$), ($B_2$), ($B_3$), or ($B_4$),

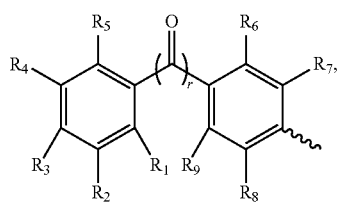

($L_1$)

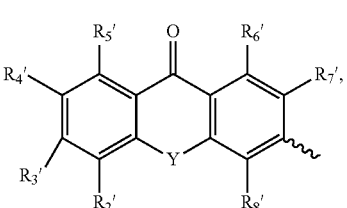

($L_2$)

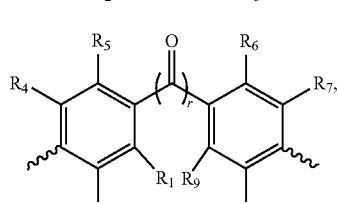

($L_3$)

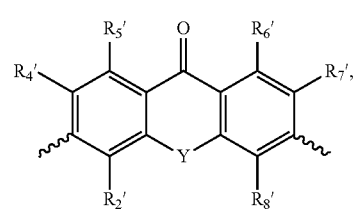

($L_4$)

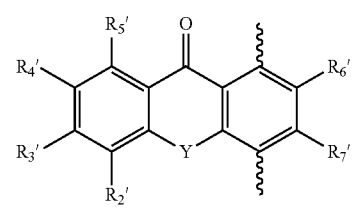

($L_5$)

wherein
r is 1 or 2; Y is one of a single bond, oxygen atom, sulfur atom, silicon atom, selenium atom, —C(O)— group, —SO₂— group, —NH— group, and $C_{1-3}$ alkylene groups; $R_1$-$R_9$ and $R_2'$-$R_8'$ are independently selected from hydrogen atom, halogen atom, monovalent polar group, and monovalent $C_{1-18}$ hydrocarbyl groups that are substituted or unsubstituted;

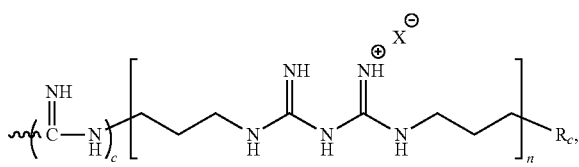

($C_1$)

wherein
c is an integer from 0 to 2, n is a positive integer from 1 to 100, $R_c$ is selected from a monovalent $C_{1-18}$ hydrocarbyl group that is unsubstituted or substituted, wherein the monovalent $C_{1-18}$ hydrocarbyl group includes or does not include a linking group including heteroatom, the heteroatom being N atom, and X is selected from halogen atom;

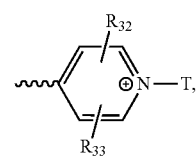

($D_2$)

wherein
T is $R_{13}$ or —$R_{23}$-A⊖, $R_{13}$ is independently selected from monovalent $C_{1-18}$ hydrocarbyl groups that are unsubstituted or substituted, and $R_{23}$ is selected from divalent $C_{1-18}$ hydrocarbyl groups that are unsubstituted or substituted; $R_{32}$-$R_{33}$ are independently selected from hydrogen atom, halogen atom, monovalent polar group, and monovalent $C_{1-18}$ hydrocarbyl groups that are substituted or unsubstituted; A is selected from —COO, —SO$_3$ and —OPO$_2$OR$_e$, and R$_e$ is a monovalent C$_{1-6}$ alkyl, cycloalkyl, or aryl group, wherein R$_e$ is unsubstituted or substituted;
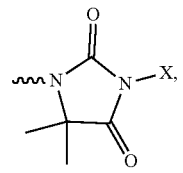 (B$_1$)
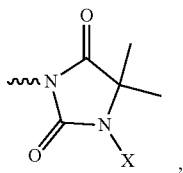 (B$_2$)
-continued
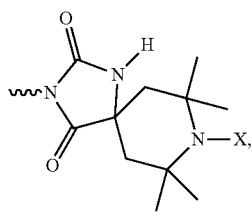 (B$_3$)
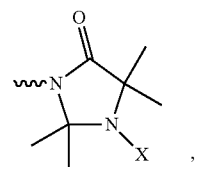 (B$_4$)
wherein X is selected from halogen atom.
15. The processing method of claim 13, wherein the synthetic fibers are polyesters, polypropylene, acrylics, nylons, vinylon, and spandex.
* * * * *